US012774486B2

(12) United States Patent
Walczak et al.

(10) Patent No.: US 12,774,486 B2
(45) Date of Patent: Oct. 27, 2026

(54) NUCLEI BARCODING AND CAPTURE IN SINGLE CELLS

(71) Applicant: CELLULAR RESEARCH, INC., Menlo Park, CA (US)

(72) Inventors: Elisabeth Marie Walczak, Menlo Park, CA (US); Eleen Shum, Menlo Park, CA (US); Christina Chang, Menlo Park, CA (US); Christina Fan, Menlo Park, CA (US)

(73) Assignee: AUGUSTA SPINCO CORPORATION, Franklin Lakes, NJ (US)

( * ) Notice: Subject to any disclaimer, the term of this patent is extended or adjusted under 35 U.S.C. 154(b) by 644 days.

(21) Appl. No.: 16/525,054

(22) Filed: Jul. 29, 2019

(65) Prior Publication Data

US 2020/0040379 A1 Feb. 6, 2020

Related U.S. Application Data

(60) Provisional application No. 62/714,222, filed on Aug. 3, 2018.

(51) Int. Cl.
*C12Q 1/6806* (2018.01)
*C12Q 1/6813* (2018.01)

(52) U.S. Cl.
CPC ......... *C12Q 1/6806* (2013.01); *C12Q 1/6813* (2013.01)

(58) Field of Classification Search
None
See application file for complete search history.

(56) References Cited

U.S. PATENT DOCUMENTS 4,499,183 A * 2/1985 Sujansky ......... G01N 33/56966 436/805
4,510,244 A 4/1985 Parks et al.
4,725,536 A 2/1988 Fritsch et al.
4,803,155 A 2/1989 Petersen et al.
4,939,082 A * 7/1990 Naujoks ............... G01N 33/573 530/808
5,124,246 A 6/1992 Urdea et al.
5,137,809 A 8/1992 Luken et al.
5,149,625 A 9/1992 Church et al.
5,200,314 A 4/1993 Urdea
5,308,990 A 5/1994 Takahashi et al.
5,424,186 A 6/1995 Fodor et al.
5,424,413 A 6/1995 Hogan et al.
5,445,934 A 8/1995 Fodor et al.
5,470,570 A 11/1995 Taylor et al.
5,604,097 A 2/1997 Brenner
5,635,352 A 6/1997 Urdea et al.
5,635,400 A 6/1997 Brenner
5,648,245 A 7/1997 Fire et al.
5,654,413 A 8/1997 Brenner
5,656,731 A 8/1997 Urdea
5,658,737 A 8/1997 Nelson et al.
5,714,330 A 2/1998 Brenner et al.
5,744,305 A 4/1998 Fodor et al.
5,759,778 A 6/1998 Li et al.
5,763,175 A 6/1998 Brenner
5,800,992 A 9/1998 Fodor et al.
5,807,674 A 9/1998 Tyagi
5,830,712 A 11/1998 Rampersad et al.
5,846,719 A 12/1998 Brenner et al.
5,854,033 A 12/1998 Lizardi
5,866,366 A 2/1999 Kallender
5,871,928 A 2/1999 Fodor et al.
5,925,525 A 7/1999 Fodor et al.
5,935,793 A 8/1999 Wong
5,945,293 A * 8/1999 Siiman ................ G01N 33/548 435/7.1
5,962,271 A 10/1999 Chenchik et al.
5,962,272 A 10/1999 Chenchik et al.
5,968,740 A 10/1999 Fodor et al.
5,981,176 A 11/1999 Wallace
5,981,179 A 11/1999 Lorinez et al.
6,013,445 A 1/2000 Albrecht et al.
6,040,138 A 3/2000 Lockhart et al.
6,046,005 A 4/2000 Ju et al.
6,060,596 A 5/2000 Lerner et al.
6,064,755 A 5/2000 Some
(Continued)

FOREIGN PATENT DOCUMENTS

CA 2474509 2/2003
CA 2961210 A1 3/2016
(Continued)

OTHER PUBLICATIONS

Kausch et al., Organelle Isolation by Magnetic Immunoabsorption, Feb. 1999, BioTechniques, 26, 336-343 (Year: 1999).*
Zhang et al., Immunoaffinity Purification of Plasma Membrane with Secondary Antibody Superparamagnetic Beads, 2006, Journal of Proteome, vol. 6, 34-43 (Year: 2006).*
Monneron, One-step Isolation and Characterization of Nuclear Membranes, 1974 Electron Microscopy and Composition of Biological Membranes and Envelops, vol. 268, pp. 101-108 (Year: 1974).*
(Continued)

*Primary Examiner* — Bradley L. Sisson
(74) *Attorney, Agent, or Firm* — Dickinson Wright PLLC

(57) ABSTRACT

Disclosed herein include methods, compositions, and kits suitable for use in performing single nuclei capture and barcoding in a single step. In some embodiments, the method comprises isolating nuclei using a nuclei-isolation composition. The nuclei-isolation composition can comprise a nuclei-binding reagent capable of specifically binding to one or more components of a nucleus. The method can include barcoding targets in the nuclei using barcodes to generate barcoded targets for sequencing analysis.

8 Claims, 16 Drawing Sheets

(56) References Cited

U.S. PATENT DOCUMENTS 6,090,592 A 7/2000 Adams et al.
6,114,149 A 9/2000 Fry et al.
6,117,631 A 9/2000 Nilsen
6,117,635 A 9/2000 Nazarendo
6,117,986 A 9/2000 Nardone
6,124,092 A 9/2000 O'Neill et al.
6,138,077 A 10/2000 Brenner
6,140,489 A 10/2000 Brenner
6,172,214 B1 1/2001 Brenner
6,197,506 B1 3/2001 Fodor et al.
6,197,554 B1 3/2001 Lin et al.
6,214,558 B1 4/2001 Shuber et al.
6,235,433 B1 5/2001 Wolber et al.
6,235,475 B1 5/2001 Brenner et al.
6,235,483 B1 5/2001 Wolber et al.
6,265,157 B1 7/2001 Prockop et al.
6,265,163 B1 7/2001 Albrecht et al.
6,268,152 B1 7/2001 Fodor et al.
6,284,460 B1 9/2001 Fodor et al.
6,284,485 B1 9/2001 Boyle et al.
6,296,855 B1 * 10/2001 Hemmen ............... C12Q 1/689 424/234.1
6,300,093 B1 * 10/2001 Kindsvogel .............. C12N 9/16 435/254.11
6,309,822 B1 10/2001 Fodor et al.
6,309,823 B1 10/2001 Cronin et al.
6,326,148 B1 12/2001 Pauletti et al.
6,355,431 B1 3/2002 Chee et al.
6,355,432 B1 3/2002 Fodor et al.
6,358,508 B1 3/2002 Ni
6,361,947 B1 3/2002 Dong
6,372,813 B1 4/2002 Johnson et al.
6,395,491 B1 5/2002 Fodor et al.
6,406,848 B1 6/2002 Bridgham et al.
6,436,675 B1 8/2002 Welch et al.
6,440,667 B1 8/2002 Fodor et al.
6,440,706 B1 8/2002 Vogelstein et al.
6,444,661 B1 * 9/2002 Barton .................. C07F 15/008 514/288
6,451,536 B1 9/2002 Fodor et al.
6,458,530 B1 10/2002 Morris et al.
6,468,744 B1 10/2002 Cronin et al.
6,480,791 B1 11/2002 Strathmann
6,489,114 B2 12/2002 Laayoun et al.
6,489,116 B2 12/2002 Wagner
6,492,121 B2 12/2002 Kurane et al.
6,500,620 B2 12/2002 Yu et al.
6,512,105 B1 1/2003 Hogan et al.
6,514,699 B1 2/2003 O'Neill et al.
6,531,283 B1 3/2003 Kingsmore et al.
6,544,739 B1 4/2003 Fodor et al.
6,551,784 B2 4/2003 Fodor et al.
6,576,424 B2 6/2003 Fodor et al.
6,600,996 B2 7/2003 Webster et al.
6,629,040 B1 9/2003 Goodlett et al.
6,653,077 B1 11/2003 Brenner
6,753,147 B2 6/2004 Vogelstein et al.
6,787,308 B2 9/2004 Balasubramanian et al.
6,808,906 B2 10/2004 Shen et al.
6,849,404 B2 2/2005 Park et al.
6,852,488 B2 2/2005 Fodor et al.
6,858,412 B2 2/2005 Willis et al.
6,881,448 B1 4/2005 Hattori
6,890,741 B2 5/2005 Fan et al.
6,946,251 B2 9/2005 Kurn
6,955,901 B2 10/2005 Schouten
6,974,669 B2 12/2005 Mirkin et al.
7,022,479 B2 4/2006 Wagner
7,034,145 B2 4/2006 Shen et al.
7,155,050 B1 12/2006 Sloge
7,294,466 B2 11/2007 McMillan
7,323,309 B2 1/2008 Mirkin et al.
7,387,887 B2 6/2008 Wittwer et al.
7,393,665 B2 7/2008 Brenner
7,407,757 B2 8/2008 Brenner
7,424,368 B2 9/2008 Huang et al.
7,432,055 B2 10/2008 Pemov et al.
7,470,515 B2 12/2008 Rashtchian et al.
7,473,767 B2 1/2009 Dimitrov
7,476,786 B2 1/2009 Chan et al.
7,537,897 B2 5/2009 Brenner et al.
7,544,473 B2 6/2009 Brenner
7,635,566 B2 12/2009 Brenner
7,638,612 B2 12/2009 Rashtchian et al.
7,718,403 B2 5/2010 Kamberov et al.
7,771,946 B2 8/2010 Kurn
7,822,555 B2 10/2010 Huang et al.
7,824,856 B2 11/2010 Monforte
7,824,889 B2 11/2010 Vogelstein et al.
7,915,015 B2 3/2011 Vogelstein et al.
7,985,546 B2 7/2011 Church et al.
8,071,311 B2 12/2011 Kurn
8,110,351 B2 2/2012 Bosnes
8,114,681 B2 2/2012 Martin et al.
8,148,068 B2 4/2012 Brenner
8,168,385 B2 5/2012 Brenner
8,206,913 B1 6/2012 Kamberov et al.
8,241,850 B2 8/2012 Brenner
8,298,767 B2 10/2012 Brenner et al.
8,309,306 B2 11/2012 Nolan et al.
8,318,433 B2 11/2012 Brenner
8,367,051 B2 2/2013 Matyjaszewski et al.
8,420,324 B2 4/2013 Rashtchian et al.
8,445,205 B2 5/2013 Brenner
8,470,996 B2 6/2013 Brenner
8,476,018 B2 7/2013 Brenner
8,481,292 B2 7/2013 Casbon et al.
8,535,889 B2 9/2013 Larson et al.
8,563,274 B2 10/2013 Brenner et al.
8,603,749 B2 12/2013 Gillevet et al.
8,679,756 B1 3/2014 Brenner et al.
8,685,678 B2 4/2014 Casbon et al.
8,685,753 B2 4/2014 Martin et al.
8,691,509 B2 4/2014 May
8,715,967 B2 5/2014 Casbon et al.
8,722,368 B2 5/2014 Casbon et al.
8,728,766 B2 5/2014 Casbon et al.
8,741,606 B2 6/2014 Casbon et al.
8,835,110 B2 9/2014 Wang et al.
8,835,358 B2 9/2014 Fodor et al.
8,841,071 B2 9/2014 Link
8,856,410 B2 10/2014 Park
8,865,470 B2 10/2014 Yan et al.
9,005,935 B2 4/2015 Belyaev
9,040,256 B2 5/2015 Grunenwald et al.
9,080,211 B2 7/2015 Grunenwald et al.
9,085,801 B2 7/2015 Grunenwald et al.
9,115,396 B2 8/2015 Grunenwald et al.
9,150,852 B2 10/2015 Samuels et al.
9,181,582 B2 11/2015 Kurn
9,181,591 B2 11/2015 Robins et al.
9,188,586 B2 11/2015 Fan et al.
9,228,229 B2 1/2016 Olson et al.
9,262,376 B2 2/2016 Tsuto
9,290,808 B2 3/2016 Fodor et al.
9,290,809 B2 3/2016 Fodor et al.
9,297,047 B2 3/2016 Furchak et al.
9,315,857 B2 4/2016 Fu et al.
9,371,598 B2 6/2016 Chee
9,567,645 B2 2/2017 Fan et al.
9,567,646 B2 2/2017 Fan et al.
9,582,877 B2 2/2017 Fu et al.
9,593,365 B2 3/2017 Frisen et al.
9,598,736 B2 3/2017 Fan et al.
9,637,799 B2 5/2017 Fan et al.
9,644,204 B2 5/2017 Hindson et al.
9,677,131 B2 6/2017 Fredriksson et al.
9,689,024 B2 6/2017 Hindson et al.
9,695,468 B2 7/2017 Hindson et al.
9,708,659 B2 7/2017 Fodor et al.
9,727,810 B2 8/2017 Fodor et al.
9,787,810 B1 10/2017 Chiang
9,816,137 B2 11/2017 Fodor et al.
9,845,502 B2 12/2017 Fodor et al.

(56) References Cited

U.S. PATENT DOCUMENTS 9,850,515 B2 12/2017 McCoy et al.
9,856,530 B2 1/2018 Hindson et al.
9,868,979 B2 1/2018 Chee et al.
9,879,313 B2 1/2018 Chee et al.
9,905,005 B2 2/2018 Fu et al.
9,938,523 B2 4/2018 LaBaer
9,938,524 B2 4/2018 Fernandez et al.
9,939,443 B2 4/2018 Spetzler et al.
9,951,386 B2 4/2018 Hindson et al.
9,957,549 B2 5/2018 Armour et al.
9,988,660 B2 6/2018 Rashtchian et al.
10,002,316 B2 6/2018 Fodor et al.
10,011,872 B1 7/2018 Belgrader et al.
10,017,761 B2 7/2018 Weissman et al.
10,023,910 B2 7/2018 Drmanac et al.
10,030,267 B2 7/2018 Hindson et al.
10,041,116 B2 8/2018 Hindson et al.
10,047,394 B2 8/2018 Fodor et al.
10,059,989 B2 8/2018 Giresi et al.
10,059,991 B2 8/2018 Fodor et al.
10,131,958 B1 11/2018 Fan et al.
10,138,518 B2 11/2018 Chun
10,150,995 B1 12/2018 Giresi et al.
10,151,003 B2 12/2018 Fan et al.
10,155,942 B2 12/2018 Kurihara
10,184,122 B2 1/2019 Grunenwald et al.
10,202,641 B2 2/2019 Shum
10,202,646 B2 2/2019 Fodor et al.
10,208,343 B2 2/2019 Hindson et al.
10,208,356 B1 2/2019 Fan et al.
10,227,648 B2 3/2019 Hindson et al.
10,240,196 B2 3/2019 Arezi et al.
10,246,703 B2 4/2019 Church et al.
10,253,364 B2 4/2019 Hindson et al.
10,253,375 B1 4/2019 Fan et al.
10,266,874 B2 4/2019 Weissleder et al.
10,273,541 B2 4/2019 Hindson et al.
10,288,608 B2 5/2019 Kozlov et al.
10,294,511 B2 5/2019 Sanches-Kuiper et al.
10,301,677 B2 5/2019 Shum et al.
10,308,982 B2 6/2019 Chee
10,323,278 B2 6/2019 Belgrader et al.
10,337,061 B2 7/2019 Hindson et al.
10,337,062 B2 7/2019 Giresi et al.
10,338,066 B2 7/2019 Fan et al.
10,344,329 B2 7/2019 Hindson et al.
10,392,661 B2 8/2019 Fodor et al.
10,400,235 B2 9/2019 Belhocine et al.
10,450,607 B2 10/2019 Hindson et al.
10,550,429 B2 2/2020 Harada et al.
10,619,186 B2 4/2020 Betts et al.
10,619,203 B2 4/2020 Fodor et al.
10,619,207 B2 4/2020 Giresi et al.
RE47,983 E 5/2020 Gao et al.
10,669,570 B2 6/2020 Chang et al.
10,676,779 B2 6/2020 Chang et al.
10,689,643 B2 6/2020 Jelinek et al.
10,725,027 B2 7/2020 Bell et al.
10,738,357 B2 8/2020 Giresi et al.
10,844,372 B2 11/2020 Belhocine et al.
10,889,859 B2 1/2021 Giresi et al.
10,894,980 B2 1/2021 Chen et al.
10,907,205 B2 2/2021 Lebofsky et al.
10,914,729 B2 2/2021 Check et al.
10,927,370 B2 2/2021 Belhocine et al.
10,927,419 B2 2/2021 Fan et al.
10,934,636 B2 3/2021 Bock et al.
10,941,396 B2 3/2021 Fu et al.
10,954,570 B2 3/2021 Fan et al.
10,975,371 B2 4/2021 Salathia
11,074,991 B2 7/2021 Zheng
11,092,607 B2 8/2021 Gaublomme et al.
11,118,175 B2 9/2021 Grunenwald et al.
11,155,810 B2 10/2021 Belhocine et al.
11,198,866 B2 12/2021 Belhocine et al.
11,306,307 B2 4/2022 Jelinek et al.
11,319,583 B2 5/2022 Shum et al.
11,365,409 B2 6/2022 Shum et al.
11,390,914 B2 7/2022 Fu et al.
11,460,468 B2 10/2022 Fan et al.
11,467,157 B2 10/2022 Fan et al.
11,525,157 B2 12/2022 Shum
11,535,882 B2 12/2022 Fu et al.
11,618,929 B2 4/2023 Fan et al.
11,634,708 B2 4/2023 Fu et al.
11,661,625 B2 5/2023 Jensen et al.
11,702,706 B2 7/2023 Fan et al.
11,773,436 B2 10/2023 Chang et al.
11,773,441 B2 10/2023 Fan et al.
11,782,059 B2 10/2023 Fan et al.
11,932,849 B2 3/2024 Shum
11,932,901 B2 3/2024 Song et al.
11,939,622 B2 3/2024 Song
11,970,737 B2 4/2024 Fodor
11,993,814 B2 5/2024 Fodor
12,060,607 B2 8/2024 Fodor
12,071,617 B2 8/2024 Shum
12,084,712 B2 9/2024 Chang
12,392,771 B2 8/2025 Song
2001/0024784 A1 9/2001 Wagner
2001/0036632 A1 11/2001 Yu et al.
2002/0019005 A1 2/2002 Kamb
2002/0051986 A1 5/2002 Baez et al.
2002/0065609 A1 5/2002 Ashby
2002/0072058 A1 6/2002 Voelker et al.
2002/0094116 A1 7/2002 Forst et al.
2002/0102584 A1 8/2002 Hester
2002/0106666 A1 8/2002 Hayashizaki
2002/0132241 A1 9/2002 Fan et al.
2002/0168665 A1 11/2002 Okawa
2002/0172953 A1 11/2002 Mirkin et al.
2002/0187480 A1 12/2002 Brandon
2002/0192687 A1 12/2002 Mirkin et al.
2003/0003490 A1 1/2003 Fan et al.
2003/0013091 A1 1/2003 Dimitrov
2003/0032049 A1 2/2003 Wagner
2003/0049616 A1 3/2003 Brenner et al.
2003/0077611 A1 4/2003 Slepnev
2003/0082818 A1 5/2003 Bahnson et al.
2003/0087242 A1 5/2003 Mirkin et al.
2003/0092624 A1* 5/2003 Wang ....................... C12N 9/96
800/278
2003/0104436 A1 6/2003 Morris et al.
2003/0124568 A1* 7/2003 Spielvogel ........... C07K 14/705
435/7.1
2003/0143740 A1 7/2003 Wooddell
2003/0165935 A1 9/2003 Vann et al.
2003/0175908 A1 9/2003 Linnarsson
2003/0186251 A1 10/2003 Dunn et al.
2003/0207296 A1 11/2003 Park et al.
2003/0207300 A1 11/2003 Matray et al.
2004/0047769 A1 3/2004 Tanaami
2004/0091864 A1 5/2004 French et al.
2004/0096368 A1 5/2004 Davis et al.
2004/0096892 A1 5/2004 Wang et al.
2004/0121342 A1 6/2004 Mckeown
2004/0142344 A1 7/2004 Bazan et al.
2004/0146901 A1 7/2004 Morris et al.
2004/0147435 A1 7/2004 Hawiger et al.
2004/0157243 A1 8/2004 Huang et al.
2004/0180361 A1 9/2004 Dahl et al.
2004/0209298 A1 10/2004 Kamberov et al.
2004/0224325 A1 11/2004 Knapp et al.
2004/0259118 A1 12/2004 Macevicz
2005/0019776 A1 1/2005 Callow et al.
2005/0032110 A1 2/2005 Shen et al.
2005/0037397 A1 2/2005 Mirkin
2005/0048500 A1 3/2005 Lawton
2005/0053952 A1 3/2005 Hong et al.
2005/0105077 A1 5/2005 Padmanabhan et al.
2005/0130173 A1 6/2005 Leamon et al.
2005/0170373 A1 8/2005 Monforte
2005/0175993 A1 8/2005 Wei
2005/0196760 A1 9/2005 Pemov et al.

(56) References Cited

U.S. PATENT DOCUMENTS

2005/0214825 A1 9/2005 Stuelpnagel
2005/0250146 A1 11/2005 McMillan
2005/0250147 A1 11/2005 Macevicz
2005/0266417 A1 12/2005 Barany
2006/0002824 A1 1/2006 Chang et al.
2006/0035258 A1 2/2006 Tadakamalla et al.
2006/0040297 A1 2/2006 Leamon et al.
2006/0041385 A1 2/2006 Bauer
2006/0057634 A1 3/2006 Rye
2006/0073506 A1 4/2006 Christians et al.
2006/0211030 A1 9/2006 Brenner
2006/0257902 A1 11/2006 Mendoza et al.
2006/0263709 A1 11/2006 Matsumura et al.
2006/0263789 A1 11/2006 Kincaid
2006/0280352 A1 12/2006 Muschler et al.
2006/0281092 A1 12/2006 Wille et al.
2006/0286570 A1 12/2006 Rowlen et al.
2006/0294606 A1 12/2006 Moisyadi
2007/0020640 A1 1/2007 Mccloskey et al.
2007/0031829 A1 2/2007 Yasuno et al.
2007/0042400 A1 2/2007 Choi et al.
2007/0042419 A1 2/2007 Barany et al.
2007/0065823 A1 3/2007 Dressman et al.
2007/0065844 A1 3/2007 Golub et al.
2007/0105090 A1 5/2007 Cassidy et al.
2007/0117121 A1 5/2007 Hutchison et al.
2007/0117134 A1 5/2007 Kou
2007/0117177 A1 5/2007 Luo et al.
2007/0133856 A1 6/2007 Dutta-Choudhury
2007/0166741 A1 7/2007 Heil et al.
2007/0172873 A1 7/2007 Brenner et al.
2007/0178478 A1 8/2007 Dhallan et al.
2007/0202523 A1 8/2007 Becker et al.
2007/0281317 A1 12/2007 Becker et al.
2008/0038727 A1 2/2008 Spier
2008/0038735 A1* 2/2008 Sepp .................... C07K 16/241 435/325
2008/0064042 A1 3/2008 Bazan et al.
2008/0070303 A1 3/2008 West et al.
2008/0119736 A1 5/2008 Dentinger
2008/0161365 A1 7/2008 Booth
2008/0194414 A1 8/2008 Albert et al.
2008/0261204 A1 10/2008 Lexow
2008/0268508 A1 10/2008 Sowlay
2008/0269068 A1 10/2008 Church et al.
2008/0274458 A1 11/2008 Latham et al.
2008/0293164 A1 11/2008 Gaylord et al.
2008/0299609 A1 12/2008 Kwon et al.
2008/0318802 A1 12/2008 Brenner
2009/0011943 A1* 1/2009 Drmanac ............... C12N 15/66 506/4
2009/0053669 A1 2/2009 Liu et al.
2009/0053698 A1 2/2009 Hayashida
2009/0061513 A1 3/2009 Andersson Svahn et al.
2009/0105959 A1 4/2009 Braverman et al.
2009/0131269 A1 5/2009 Martin et al.
2009/0137407 A1 5/2009 Church et al.
2009/0163366 A1 6/2009 Nickerson
2009/0208936 A1 8/2009 Tan et al.
2009/0220385 A1 9/2009 Brown et al.
2009/0226891 A2 9/2009 Nova et al.
2009/0252414 A1 10/2009 Suzuki
2009/0253586 A1 10/2009 Nelson et al.
2009/0283676 A1 11/2009 Skoglund
2009/0290151 A1 11/2009 Agrawal et al.
2009/0298709 A1 12/2009 Ma
2009/0311694 A1 12/2009 Gallagher et al.
2010/0035246 A1* 2/2010 Lushi .................. C12Q 1/6879 435/29
2010/0069250 A1 3/2010 White, III
2010/0075436 A1 3/2010 Urdea
2010/0105049 A1 4/2010 Ehrich et al.
2010/0105112 A1 4/2010 Holtze et al.
2010/0105886 A1 4/2010 Woudenberg et al.
2010/0120098 A1 5/2010 Grunenwald et al.
2010/0120630 A1 5/2010 Huang et al.
2010/0136544 A1 6/2010 Agresti et al.
2010/0136702 A1 6/2010 Bazan et al.
2010/0151471 A1 6/2010 Faham et al.
2010/0159533 A1 6/2010 Lipson et al.
2010/0167313 A1* 7/2010 Essig ................ C07K 16/4241 530/387.2
2010/0167354 A1 7/2010 Kurn
2010/0184076 A1 7/2010 Lawton
2010/0255471 A1 10/2010 Clarke
2010/0267028 A1 10/2010 Pasche
2010/0291666 A1 11/2010 Collier et al.
2010/0297644 A1 11/2010 Kokoris
2010/0298152 A1* 11/2010 Brown ................ C12N 15/115 506/4
2010/0300895 A1 12/2010 Nobile et al.
2010/0304445 A1 12/2010 Szybalski
2010/0323348 A1 12/2010 Hamady et al.
2010/0330574 A1 12/2010 Whitman
2011/0038507 A1 2/2011 Hager
2011/0059436 A1 3/2011 Hardin et al.
2011/0059556 A1 3/2011 Strey
2011/0070584 A1 3/2011 Wohlgemuth et al.
2011/0072889 A1 3/2011 Albitar et al.
2011/0145937 A1 6/2011 MacDonald
2011/0160078 A1 6/2011 Fodor et al.
2011/0171749 A1* 7/2011 Alocilja .................. B82Y 5/00 536/23.1
2011/0201507 A1 8/2011 Rava et al.
2011/0230358 A1 9/2011 Rava
2011/0244455 A1 10/2011 Larson et al.
2011/0245111 A1 10/2011 Chee
2011/0256549 A1 10/2011 Gaylord et al.
2011/0257031 A1 10/2011 Bodeau
2011/0263457 A1 10/2011 Krutzik et al.
2011/0294689 A1 12/2011 Namsaraev
2011/0312511 A1 12/2011 Winquist et al.
2011/0319289 A1 12/2011 Libutti
2012/0004132 A1 1/2012 Zhang et al.
2012/0010091 A1 1/2012 Linnarson
2012/0014977 A1 1/2012 Furihata et al.
2012/0028828 A1 2/2012 Gaylord et al.
2012/0034221 A1 2/2012 Bonvini
2012/0034607 A1 2/2012 Rothberg et al.
2012/0040843 A1 2/2012 Ducree et al.
2012/0045844 A1 2/2012 Rothberg et al.
2012/0058520 A1 3/2012 Hayashida
2012/0058902 A1 3/2012 Livingston et al.
2012/0065081 A1 3/2012 Chee
2012/0065082 A1 3/2012 Kuypers
2012/0071331 A1 3/2012 Casbon
2012/0087862 A1 4/2012 Hood et al.
2012/0142018 A1 6/2012 Jiang
2012/0149603 A1 6/2012 Cooney et al.
2012/0156675 A1 6/2012 Lueerssen et al.
2012/0163681 A1 6/2012 Lohse
2012/0165219 A1 6/2012 Van Der Zaag et al.
2012/0173159 A1 7/2012 Davey et al.
2012/0190020 A1 7/2012 Oliphant et al.
2012/0202293 A1 8/2012 Martin et al.
2012/0220022 A1 8/2012 Ehrlich et al.
2012/0220494 A1 8/2012 Samuels et al.
2012/0231972 A1 9/2012 Golyshin et al.
2012/0252012 A1 10/2012 Armougom et al.
2012/0252986 A1 10/2012 Liu et al.
2012/0253689 A1 10/2012 Rogan
2012/0316074 A1 12/2012 Saxonov
2012/0322681 A1 12/2012 Kung et al.
2013/0005585 A1 1/2013 Anderson et al.
2013/0022977 A1 1/2013 Lapidus et al.
2013/0045994 A1 2/2013 Shinozuka et al.
2013/0116130 A1 5/2013 Fu et al.
2013/0137094 A1 5/2013 Espina et al.
2013/0190193 A1 7/2013 Bazan et al.
2013/0190206 A1 7/2013 Leonard
2013/0203047 A1 8/2013 Casbon et al.
2013/0210643 A1 8/2013 Casbon et al.
2013/0210659 A1 8/2013 Watson et al.
2013/0224743 A1 8/2013 Casbon et al.

(56) References Cited

U.S. PATENT DOCUMENTS

| | | | |
|---|---|---|---|
| 2013/0225418 | A1 | 8/2013 | Watson |
| 2013/0225623 | A1 | 8/2013 | Buxbaum et al. |
| 2013/0237458 | A1 | 9/2013 | Casbon et al. |
| 2013/0267424 | A1 | 10/2013 | Casbon et al. |
| 2013/0274117 | A1 | 10/2013 | Church |
| 2013/0303461 | A1 | 11/2013 | Lafrate et al. |
| 2013/0323732 | A1 | 12/2013 | Anderson et al. |
| 2013/0338038 | A1* | 12/2013 | DuBridge ............ C12Q 1/6883 506/10 |
| 2014/0004569 | A1 | 1/2014 | Lambowitz et al. |
| 2014/0057799 | A1 | 2/2014 | Johnson et al. |
| 2014/0066318 | A1 | 3/2014 | Frisen et al. |
| 2014/0093916 | A1 | 4/2014 | Belyaev |
| 2014/0100122 | A1 | 4/2014 | Rearick |
| 2014/0147860 | A1 | 5/2014 | Kaduchak et al. |
| 2014/0155274 | A1 | 6/2014 | Xie et al. |
| 2014/0155295 | A1 | 6/2014 | Hindson et al. |
| 2014/0178438 | A1 | 6/2014 | Sahin et al. |
| 2014/0194324 | A1 | 7/2014 | Gormley et al. |
| 2014/0206079 | A1 | 7/2014 | Malinoski et al. |
| 2014/0206547 | A1 | 7/2014 | Wang |
| 2014/0216128 | A1 | 8/2014 | Trotter et al. |
| 2014/0227684 | A1 | 8/2014 | Hindson et al. |
| 2014/0227705 | A1 | 8/2014 | Vogelstein et al. |
| 2014/0228239 | A1 | 8/2014 | McCoy et al. |
| 2014/0228255 | A1 | 8/2014 | Hindson et al. |
| 2014/0235506 | A1 | 8/2014 | Hindson et al. |
| 2014/0243242 | A1 | 8/2014 | Nicol et al. |
| 2014/0244742 | A1 | 8/2014 | Yu et al. |
| 2014/0256568 | A1 | 9/2014 | Link |
| 2014/0256918 | A1 | 9/2014 | Chu |
| 2014/0272952 | A1 | 9/2014 | May et al. |
| 2014/0274811 | A1 | 9/2014 | Arnold |
| 2014/0287963 | A1 | 9/2014 | Hindson et al. |
| 2014/0303005 | A1 | 10/2014 | Samuels et al. |
| 2014/0309945 | A1 | 10/2014 | Park et al. |
| 2014/0315211 | A1 | 10/2014 | Sugino et al. |
| 2014/0322716 | A1 | 10/2014 | Robins |
| 2014/0323330 | A1 | 10/2014 | Bergo |
| 2014/0357500 | A1 | 12/2014 | Vigneault et al. |
| 2014/0378322 | A1 | 12/2014 | Hindson et al. |
| 2014/0378345 | A1 | 12/2014 | Hindson et al. |
| 2014/0378349 | A1 | 12/2014 | Hindson et al. |
| 2014/0378350 | A1 | 12/2014 | Hindson et al. |
| 2015/0005185 | A1 | 1/2015 | Fodor et al. |
| 2015/0005199 | A1 | 1/2015 | Hindson et al. |
| 2015/0005200 | A1 | 1/2015 | Hindson et al. |
| 2015/0011396 | A1 | 1/2015 | Schroeder et al. |
| 2015/0017654 | A1 | 1/2015 | Gorfinkel et al. |
| 2015/0066385 | A1 | 3/2015 | Schnall-Levin et al. |
| 2015/0072867 | A1 | 3/2015 | Soldatov et al. |
| 2015/0072873 | A1 | 3/2015 | Heinz et al. |
| 2015/0080266 | A1 | 3/2015 | Volkmuth et al. |
| 2015/0087535 | A1 | 3/2015 | Patel |
| 2015/0099661 | A1 | 4/2015 | Fodor et al. |
| 2015/0099673 | A1 | 4/2015 | Fodor et al. |
| 2015/0111256 | A1 | 4/2015 | Church et al. |
| 2015/0118680 | A1 | 4/2015 | Fodor et al. |
| 2015/0119255 | A1 | 4/2015 | Fodor et al. |
| 2015/0119256 | A1 | 4/2015 | Fodor et al. |
| 2015/0119257 | A1 | 4/2015 | Fodor et al. |
| 2015/0119258 | A1 | 4/2015 | Fodor et al. |
| 2015/0119290 | A1 | 4/2015 | Fodor et al. |
| 2015/0133319 | A1 | 5/2015 | Fu et al. |
| 2015/0141292 | A1 | 5/2015 | Fodor et al. |
| 2015/0148685 | A1 | 5/2015 | Baym |
| 2015/0152409 | A1 | 6/2015 | Seitz et al. |
| 2015/0203897 | A1 | 7/2015 | Robons et al. |
| 2015/0204862 | A1 | 7/2015 | Fan et al. |
| 2015/0211050 | A1 | 7/2015 | Iafrate et al. |
| 2015/0218620 | A1 | 8/2015 | Behlke et al. |
| 2015/0225777 | A1 | 8/2015 | Hindson et al. |
| 2015/0225778 | A1 | 8/2015 | Hindson et al. |
| 2015/0247182 | A1 | 9/2015 | Faham et al. |
| 2015/0253237 | A1 | 9/2015 | Castellarnau et al. |
| 2015/0259734 | A1 | 9/2015 | Asbury et al. |
| 2015/0275295 | A1 | 10/2015 | Wang et al. |
| 2015/0298091 | A1 | 10/2015 | Weitz |
| 2015/0299784 | A1 | 10/2015 | Fan et al. |
| 2015/0307874 | A1 | 10/2015 | Jaitin |
| 2015/0329852 | A1 | 11/2015 | Nolan |
| 2015/0337369 | A1 | 11/2015 | Davis et al. |
| 2015/0360193 | A1 | 12/2015 | Fan et al. |
| 2015/0376609 | A1 | 12/2015 | Hindson et al. |
| 2016/0010151 | A1 | 1/2016 | Fan et al. |
| 2016/0017320 | A1 | 1/2016 | Wang et al. |
| 2016/0025735 | A1 | 1/2016 | Gaylord et al. |
| 2016/0026758 | A1 | 1/2016 | Jabara et al. |
| 2016/0053253 | A1 | 2/2016 | Salathia et al. |
| 2016/0055632 | A1 | 2/2016 | Fu et al. |
| 2016/0060621 | A1 | 3/2016 | Agresti et al. |
| 2016/0060682 | A1 | 3/2016 | Pregibon et al. |
| 2016/0068889 | A1 | 3/2016 | Gole et al. |
| 2016/0122751 | A1 | 5/2016 | LaBaer |
| 2016/0122753 | A1 | 5/2016 | Mikkelsen et al. |
| 2016/0138086 | A1 | 5/2016 | Seelig |
| 2016/0138091 | A1 | 5/2016 | Chee et al. |
| 2016/0145677 | A1 | 5/2016 | Chee et al. |
| 2016/0145683 | A1 | 5/2016 | Fan et al. |
| 2016/0153973 | A1 | 6/2016 | Smith |
| 2016/0201125 | A1 | 7/2016 | Samuels et al. |
| 2016/0208322 | A1 | 7/2016 | Anderson et al. |
| 2016/0222378 | A1 | 8/2016 | Fodor et al. |
| 2016/0232291 | A1 | 8/2016 | Kyriazopoulou-Panagiotopoulou et al. |
| 2016/0244742 | A1 | 8/2016 | Linnarsson et al. |
| 2016/0244825 | A1 | 8/2016 | Vigneault et al. |
| 2016/0244828 | A1 | 8/2016 | Mason |
| 2016/0253584 | A1* | 9/2016 | Fodor .................. C12Q 1/6816 235/494 |
| 2016/0257993 | A1 | 9/2016 | Fu et al. |
| 2016/0258012 | A2 | 9/2016 | Fodor et al. |
| 2016/0265027 | A1 | 9/2016 | Sanches-Kuiper et al. |
| 2016/0265069 | A1 | 9/2016 | Fan et al. |
| 2016/0266094 | A1 | 9/2016 | Ankrum et al. |
| 2016/0289669 | A1 | 10/2016 | Fan et al. |
| 2016/0289670 | A1 | 10/2016 | Samuels et al. |
| 2016/0289740 | A1 | 10/2016 | Fu et al. |
| 2016/0298180 | A1 | 10/2016 | Chee |
| 2016/0312276 | A1 | 10/2016 | Fu et al. |
| 2016/0320720 | A1 | 11/2016 | Murata et al. |
| 2016/0326584 | A1 | 11/2016 | Fodor et al. |
| 2016/0340720 | A1 | 11/2016 | Fan et al. |
| 2016/0355879 | A1 | 12/2016 | Kamberov et al. |
| 2016/0362730 | A1 | 12/2016 | Alexander et al. |
| 2016/0369329 | A1 | 12/2016 | Cai |
| 2016/0376583 | A1 | 12/2016 | Fodor et al. |
| 2016/0376648 | A1 | 12/2016 | Fodor et al. |
| 2017/0044525 | A1 | 2/2017 | Kaper et al. |
| 2017/0073730 | A1 | 3/2017 | Betts et al. |
| 2017/0089892 | A1 | 3/2017 | Aghvanyan et al. |
| 2017/0136458 | A1 | 5/2017 | Dunne et al. |
| 2017/0138942 | A1 | 5/2017 | Fan et al. |
| 2017/0154421 | A1 | 6/2017 | Fu et al. |
| 2017/0192013 | A1 | 7/2017 | Agresti et al. |
| 2017/0260584 | A1 | 9/2017 | Zheng et al. |
| 2017/0268981 | A1 | 9/2017 | Diebold |
| 2017/0275669 | A1 | 9/2017 | Weissleder et al. |
| 2017/0314067 | A1 | 11/2017 | Shum et al. |
| 2017/0321251 | A1 | 11/2017 | Nolan |
| 2017/0337459 | A1 | 11/2017 | Fodor et al. |
| 2017/0342405 | A1 | 11/2017 | Fu et al. |
| 2017/0342465 | A1 | 11/2017 | Shum et al. |
| 2017/0342484 | A1 | 11/2017 | Shum et al. |
| 2017/0344866 | A1 | 11/2017 | Fan et al. |
| 2018/0002738 | A1 | 1/2018 | Wang et al. |
| 2018/0002764 | A1 | 1/2018 | Fan et al. |
| 2018/0016632 | A1 | 1/2018 | Penkler |
| 2018/0016634 | A1 | 1/2018 | Hindson et al. |
| 2018/0024139 | A1 | 1/2018 | Peikon et al. |
| 2018/0030504 | A1 | 2/2018 | Nolan et al. |
| 2018/0030522 | A1 | 2/2018 | Kamberov et al. |
| 2018/0037942 | A1 | 2/2018 | Fu et al. |
| 2018/0057873 | A1 | 3/2018 | Zhou et al. |

(56) References Cited

U.S. PATENT DOCUMENTS

2018/0088112 A1 3/2018 Fan et al.
2018/0094312 A1 4/2018 Hindson et al.
2018/0094314 A1 4/2018 Hindson et al.
2018/0094315 A1 4/2018 Hindson et al.
2018/0105808 A1 4/2018 Mikkelsen et al.
2018/0112266 A1 4/2018 Hindson et al.
2018/0119143 A1* 5/2018 Pirozhkova ........ A61K 31/7088
2018/0127743 A1 5/2018 Vigneault et al.
2018/0142292 A1 5/2018 Hindson et al.
2018/0163201 A1 6/2018 Larson
2018/0179590 A1 6/2018 Belgrader et al.
2018/0179591 A1 6/2018 Belgrader et al.
2018/0200710 A1* 7/2018 Spuhler .................. B01L 3/502
2018/0201923 A1 7/2018 LaBaer
2018/0201980 A1 7/2018 Chee et al.
2018/0208975 A1 7/2018 Peterson et al.
2018/0216162 A1 8/2018 Belhocine et al.
2018/0216163 A1 8/2018 Willey
2018/0216174 A1* 8/2018 Shum ................. C12N 15/1093
2018/0230527 A1 8/2018 Fang et al.
2018/0245069 A1 8/2018 Desantis et al.
2018/0251825 A1 9/2018 Stoeckius et al.
2018/0258482 A1 9/2018 Hindson et al.
2018/0258500 A1 9/2018 Fan et al.
2018/0267036 A1 9/2018 Fan et al.
2018/0276332 A1 9/2018 Fan et al.
2018/0282803 A1 10/2018 Belgrader et al.
2018/0291470 A1 10/2018 Fan et al.
2018/0320224 A1 11/2018 Gaublomme et al.
2018/0320241 A1 11/2018 Nolan et al.
2018/0327835 A1 11/2018 Fodor et al.
2018/0327836 A1 11/2018 Fodor et al.
2018/0327838 A1 11/2018 Giresi et al.
2018/0327866 A1 11/2018 Fan et al.
2018/0327867 A1 11/2018 Fan et al.
2018/0340169 A1 11/2018 Bethocine et al.
2018/0340170 A1 11/2018 Belhocine et al.
2018/0340172 A1 11/2018 Belhocine et al.
2018/0346969 A1 12/2018 Chang et al.
2018/0346970 A1 12/2018 Chang et al.
2018/0346979 A1 12/2018 Hindson et al.
2018/0371536 A1 12/2018 Fu et al.
2019/0002971 A1* 1/2019 Koslover ............. C12Q 1/6869
2019/0010552 A1 1/2019 Xu et al.
2019/0025304 A1 1/2019 Vigneault et al.
2019/0032129 A1 1/2019 Hindson et al.
2019/0040464 A1 2/2019 Giresi et al.
2019/0040474 A1 2/2019 Fan et al.
2019/0071656 A1 3/2019 Chang et al.
2019/0083665 A1 3/2019 Garcia-Martinez
2019/0085324 A1 3/2019 Revev et al.
2019/0085412 A1 3/2019 Fan et al.
2019/0093146 A1 3/2019 Nolan
2019/0095578 A1 3/2019 Shum et al.
2019/0100798 A1 4/2019 Fodor et al.
2019/0119726 A1 4/2019 Shum et al.
2019/0136316 A1 5/2019 Hindson et al.
2019/0136317 A1 5/2019 Hindson et al.
2019/0136319 A1 5/2019 Hindson et al.
2019/0145982 A1 5/2019 Chee et al.
2019/0161743 A1 5/2019 Church et al.
2019/0177788 A1 6/2019 Hindson et al.
2019/0177800 A1 6/2019 Boutet et al.
2019/0185936 A1 6/2019 Babiarz
2019/0203270 A1 7/2019 Amit et al.
2019/0203291 A1 7/2019 Hindson et al.
2019/0211395 A1 7/2019 Tsao et al.
2019/0218276 A1 7/2019 Regev et al.
2019/0218607 A1 7/2019 Love et al.
2019/0221287 A1 7/2019 Tsujimoto
2019/0221292 A1 7/2019 Tsujimoto
2019/0256888 A1 8/2019 Weissleder et al.
2019/0256907 A1 8/2019 Ryan et al.
2019/0270983 A1 9/2019 Belhocine et al.
2019/0292592 A1 9/2019 Shum et al.
2019/0338278 A1 11/2019 Shum et al.
2019/0338353 A1 11/2019 Belgrader et al.
2019/0338357 A1 11/2019 Fan et al.
2019/0361017 A1 11/2019 Mallick
2019/0376058 A1 12/2019 Belhocine et al.
2019/0376118 A1 12/2019 Belhocine et al.
2019/0390253 A1 12/2019 Kennedy et al.
2020/0042007 A1 2/2020 Zhang et al.
2020/0058371 A1 2/2020 Chang et al.
2020/0102598 A1 4/2020 Xie et al.
2020/0109437 A1 4/2020 Chang et al.
2020/0115753 A1 4/2020 Shalek et al.
2020/0124601 A1 4/2020 Fan et al.
2020/0149037 A1 5/2020 Shum
2020/0157600 A1 5/2020 Fu et al.
2020/0190564 A1 6/2020 Shum
2020/0216877 A1 7/2020 Betts et al.
2020/0232032 A1 7/2020 Shum et al.
2020/0291454 A1 9/2020 Belhocine et al.
2020/0299764 A1 9/2020 Miller et al.
2020/0332359 A1 10/2020 Giresi et al.
2020/0385782 A1 12/2020 McDermott
2020/0407781 A1 12/2020 Schnall-Levin et al.
2021/0010070 A1 1/2021 Schnall-Levin et al.
2021/0039582 A1 2/2021 Patton et al.
2021/0047635 A1 2/2021 Gloeckner
2021/0047677 A1 2/2021 Jhutty et al.
2021/0054436 A1 2/2021 Lam et al.
2021/0102936 A1 4/2021 Belhocine et al.
2021/0123044 A1 4/2021 Zhang et al.
2021/0132078 A1 5/2021 Peikon et al.
2021/0139970 A1 5/2021 Chang et al.
2021/0164036 A1 6/2021 Lebofsky et al.
2021/0171938 A1 6/2021 Regev
2021/0190770 A1 6/2021 Delaney
2021/0198754 A1 7/2021 Fan et al.
2021/0213413 A1 7/2021 Saligrama et al.
2021/0214770 A1 7/2021 Prosen et al.
2021/0214784 A1 7/2021 Prosen et al.
2021/0222163 A1 7/2021 Wu et al.
2021/0222244 A1 7/2021 Martin et al.
2021/0230582 A1 7/2021 Fu et al.
2021/0230583 A1 7/2021 Lam et al.
2021/0230666 A1 7/2021 Wu et al.
2021/0246492 A1 8/2021 Song et al.
2021/0263019 A1 8/2021 Martin et al.
2021/0269849 A1 9/2021 Giresi
2021/0270818 A1 9/2021 Bell et al.
2021/0285045 A1 9/2021 Giresi et al.
2021/0332354 A1 10/2021 Shah et al.
2021/0355484 A1 11/2021 Jensen et al.
2021/0364502 A1 11/2021 Belhocine et al.
2021/0371909 A1 12/2021 Lazaruk
2021/0371914 A1 12/2021 Stoeckius et al.
2022/0010361 A1 1/2022 Song et al.
2022/0010362 A1 1/2022 Campbell
2022/0033810 A1 2/2022 Song et al.
2022/0154288 A1 5/2022 Mortimer
2022/0162695 A1 5/2022 Sakofsky et al.
2022/0162773 A1 5/2022 Sakofsky et al.
2022/0178909 A1 6/2022 Huang et al.
2022/0214356 A1 7/2022 Henikoff et al.
2022/0219170 A1 7/2022 Khurana et al.
2022/0220549 A1 7/2022 Shum et al.
2022/0228203 A1 7/2022 Henikoff et al.
2022/0259586 A1 8/2022 Belhocine et al.
2022/0267759 A1 8/2022 Sanjana et al.
2022/0333185 A1 10/2022 Fu et al.
2022/0348904 A1 11/2022 Shum et al.
2022/0372554 A1 11/2022 Yang et al.
2023/0083422 A1 3/2023 Fu et al.
2023/0109336 A1 4/2023 Shum et al.
2023/0125113 A1 4/2023 Fan et al.
2023/0193372 A1 6/2023 Shum et al.

FOREIGN PATENT DOCUMENTS

CA 3034924 A1 3/2018
CN 103443338 A 12/2013

(56) References Cited

FOREIGN PATENT DOCUMENTS

| | | | |
|---|---|---|---|
| CN | 104364392 | | 2/2015 |
| CN | 104812915 | | 7/2015 |
| CN | 105705659 | A | 6/2016 |
| CN | 105886500 | A | 8/2016 |
| CN | 105886620 | A | 8/2016 |
| CN | 106460033 | A | 2/2017 |
| CN | 107208158 | A | 9/2017 |
| CN | 107250379 | A | 10/2017 |
| CN | 107580632 | A | 1/2018 |
| CN | 109526228 | A | 3/2019 |
| CN | 109791157 | A | 5/2019 |
| CN | 110382708 | | 10/2019 |
| CN | 110498858 | A | 11/2019 |
| CN | 110719959 | A | 1/2020 |
| CN | 110741092 | A | 1/2020 |
| DE | 102008025656 | | 12/2009 |
| EP | 0799897 | A1 | 10/1997 |
| EP | 1250463 | | 10/2002 |
| EP | 1473080 | | 11/2004 |
| EP | 1647600 | | 4/2006 |
| EP | 1845160 | | 10/2007 |
| EP | 2036989 | | 3/2009 |
| EP | 1379693 | | 5/2009 |
| EP | 2204456 | | 7/2010 |
| EP | 2431465 | | 3/2012 |
| EP | 2203749 | | 8/2012 |
| EP | 2511708 | | 10/2012 |
| EP | 2538220 | | 12/2012 |
| EP | 2623613 | | 8/2013 |
| EP | 2675819 | | 12/2013 |
| EP | 2697391 | | 2/2014 |
| EP | 2702146 | | 3/2014 |
| EP | 1745155 | | 10/2014 |
| EP | 2805769 | | 11/2014 |
| EP | 2820158 | | 1/2015 |
| EP | 2852682 | | 4/2015 |
| EP | 2861760 | | 4/2015 |
| EP | 2556171 | | 9/2015 |
| EP | 2954065 | | 12/2015 |
| EP | 2989215 | | 3/2016 |
| EP | 3013983 | | 5/2016 |
| EP | 3013984 | | 5/2016 |
| EP | 3089822 | | 11/2016 |
| EP | 3137601 | | 3/2017 |
| EP | 3161160 | | 5/2017 |
| EP | 3234602 | | 10/2017 |
| EP | 2970958 | | 12/2017 |
| EP | 3262192 | | 1/2018 |
| EP | 3263715 | | 1/2018 |
| EP | 3286326 | | 2/2018 |
| EP | 3318645 | | 5/2018 |
| EP | 2670863 | B1 | 6/2018 |
| EP | 3341494 | | 7/2018 |
| EP | 3347465 | | 7/2018 |
| EP | 3136103 | | 8/2018 |
| EP | 3256606 | | 8/2018 |
| EP | 3353326 | | 8/2018 |
| EP | 2954102 | | 12/2018 |
| EP | 3428290 | | 1/2019 |
| EP | 3436581 | | 2/2019 |
| EP | 2970957 | | 4/2019 |
| EP | 3465502 | | 4/2019 |
| EP | 3058092 | | 5/2019 |
| EP | 3480321 | | 5/2019 |
| EP | 3516400 | | 7/2019 |
| EP | 3327123 | | 8/2019 |
| EP | 3529357 | | 8/2019 |
| EP | 3587589 | A1 | 1/2020 |
| GB | 2293238 | A | 3/1996 |
| JP | H04108385 | | 4/1992 |
| JP | 2001078768 | A | 3/2001 |
| JP | 2001517460 | | 10/2001 |
| JP | 2002253237 | | 9/2002 |
| JP | 2005233974 | | 9/2005 |
| JP | 2007504831 | | 3/2007 |
| JP | 2008256428 | | 10/2008 |
| JP | 2012506704 | | 3/2012 |
| JP | 2013039275 | | 2/2013 |
| JP | 2015511819 | A | 4/2015 |
| JP | 2015533296 | | 11/2015 |
| JP | 2016533187 | A | 10/2016 |
| JP | 2018501776 | | 1/2018 |
| JP | 2018509896 | A | 4/2018 |
| JP | 2018535652 | A | 12/2018 |
| JP | 2019522268 | | 8/2019 |
| JP | 7413351 | | 1/2024 |
| JP | 7522189 | | 7/2024 |
| WO | WO1989001050 | | 2/1989 |
| WO | WO1996024061 | | 8/1996 |
| WO | WO1997010365 | | 3/1997 |
| WO | WO1999015702 | | 4/1999 |
| WO | WO1999028505 | | 6/1999 |
| WO | WO2000058516 | | 10/2000 |
| WO | WO2001020035 | | 3/2001 |
| WO | WO2001048242 | | 7/2001 |
| WO | WO2001053539 | | 7/2001 |
| WO | WO2002018643 | | 3/2002 |
| WO | WO2002046472 | | 6/2002 |
| WO | WO2002056014 | | 7/2002 |
| WO | WO2002059355 | | 8/2002 |
| WO | WO2002070684 | | 9/2002 |
| WO | WO2002072772 | | 9/2002 |
| WO | WO2002079490 | | 10/2002 |
| WO | WO2002083922 | | 10/2002 |
| WO | WO2002101358 | | 12/2002 |
| WO | WO2003031591 | | 4/2003 |
| WO | WO2003035829 | | 5/2003 |
| WO | WO2004017374 | | 2/2004 |
| WO | WO2004021986 | | 3/2004 |
| WO | WO2004033669 | | 4/2004 |
| WO | WO2004066185 | | 8/2004 |
| WO | WO2004081225 | | 9/2004 |
| WO | WO2005010209 | | 2/2005 |
| WO | WO2005017206 | | 2/2005 |
| WO | WO2005021731 | | 3/2005 |
| WO | WO2005026329 | | 3/2005 |
| WO | WO2005042759 | | 5/2005 |
| WO | WO2005071110 | | 8/2005 |
| WO | WO2005080604 | | 9/2005 |
| WO | WO2005111242 | | 11/2005 |
| WO | WO2005111243 | | 11/2005 |
| WO | WO2006026828 | | 3/2006 |
| WO | WO2006071776 | | 7/2006 |
| WO | WO2006102264 | | 9/2006 |
| WO | WO2006137932 | | 12/2006 |
| WO | WO2007087310 | | 8/2007 |
| WO | WO2007087312 | | 8/2007 |
| WO | WO2007147079 | | 12/2007 |
| WO | WO2008047428 | | 4/2008 |
| WO | WO2008051928 | | 5/2008 |
| WO | WO2008057163 | | 5/2008 |
| WO | WO2008096318 | | 8/2008 |
| WO | WO2008104380 | | 9/2008 |
| WO | WO2008147428 | | 12/2008 |
| WO | WO2008150432 | | 12/2008 |
| WO | WO2009048530 | | 4/2009 |
| WO | WO2009148560 | | 12/2009 |
| WO | WO2009152928 | | 12/2009 |
| WO | WO2010048605 | | 4/2010 |
| WO | WO2010059820 | | 5/2010 |
| WO | WO2010117620 | | 10/2010 |
| WO | WO2010128091 | | 11/2010 |
| WO | WO2010131645 | | 11/2010 |
| WO | WO2011091393 | | 7/2011 |
| WO | WO2011106738 | | 9/2011 |
| WO | WO2011123246 | | 10/2011 |
| WO | WO2011127099 | | 10/2011 |
| WO | WO2011142836 | | 11/2011 |
| WO | WO2011143659 | | 11/2011 |
| WO | WO2011155833 | | 12/2011 |
| WO | WO2011156529 | | 12/2011 |
| WO | WO2012038839 | | 3/2012 |
| WO | WO2012042374 | | 4/2012 |
| WO | WO2012047297 | | 4/2012 |

(56) References Cited

FOREIGN PATENT DOCUMENTS

| | | |
|---|---|---|
| WO | WO2012048341 | 4/2012 |
| WO | WO2012041802 | 5/2012 |
| WO | WO2012083225 | 6/2012 |
| WO | WO2012099896 | 7/2012 |
| WO | WO2012103154 | 8/2012 |
| WO | WO2012106385 | 8/2012 |
| WO | WO2012106546 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014062717 | 4/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014189957 | 11/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2018015365 | 1/2015 |
| WO | WO2015017586 | 2/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015104302 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015188839 | 12/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016073690 | 5/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138490 | 9/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016176091 | 11/2016 |
| WO | WO2016190795 | 12/2016 |
| WO | WO2016191272 | 12/2016 |
| WO | WO2017025594 | 2/2017 |
| WO | WO2017032808 | 3/2017 |
| WO | WO2017040306 | 3/2017 |
| WO | WO2017044574 | 3/2017 |
| WO | WO2017048993 | 3/2017 |
| WO | WO2017053905 | 3/2017 |
| WO | WO2017075265 | 5/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017156336 | 9/2017 |
| WO | WO2017164936 | 9/2017 |
| WO | WO2017171985 | 10/2017 |
| WO | WO2017173328 | 10/2017 |
| WO | WO2017204940 | 11/2017 |
| WO | WO2017205691 | 11/2017 |
| WO | WO2018013724 | 1/2018 |
| WO | WO2018017949 | 1/2018 |
| WO | WO2018018008 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018119452 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018152129 | 8/2018 |
| WO | WO2018165366 | 9/2018 |
| WO | WO2018174827 | 9/2018 |
| WO | WO2018217862 | 11/2018 |
| WO | WO2018217912 | 11/2018 |
| WO | WO2018218222 | 11/2018 |
| WO | WO2018218226 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084043 | 5/2019 |
| WO | WO2019084046 | 5/2019 |
| WO | WO2019089959 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |

(56) References Cited

FOREIGN PATENT DOCUMENTS

| | | |
|---|---|---|
| WO | WO2013137737 | 9/2019 |
| WO | WO2019178164 | 9/2019 |
| WO | WO2019210049 | 10/2019 |
| WO | WO2019213237 | 11/2019 |
| WO | WO2019213294 | 11/2019 |
| WO | WO2019218101 | 11/2019 |
| WO | WO2020009665 | 1/2020 |
| WO | WO2020028266 | 2/2020 |
| WO | WO2020033164 | 2/2020 |
| WO | WO2020037065 | 2/2020 |
| WO | WO2020041148 | 2/2020 |
| WO | WO2020046833 | 3/2020 |
| WO | WO2020047005 | 3/2020 |
| WO | WO2020072380 | 4/2020 |
| WO | WO2020097315 | 5/2020 |
| WO | WO2020123384 | 6/2020 |
| WO | WO2020131626 | 6/2020 |
| WO | WO2020131699 | 6/2020 |
| WO | WO2020154247 | 7/2020 |
| WO | WO2020159757 | 8/2020 |
| WO | WO2020167830 | 8/2020 |
| WO | WO2020167920 | 8/2020 |
| WO | WO2020168013 | 8/2020 |
| WO | WO2020247685 | 8/2020 |
| WO | WO2020176788 | 9/2020 |
| WO | WO2020214642 | 10/2020 |
| WO | WO2020219721 | 10/2020 |
| WO | WO2020242377 | 12/2020 |
| WO | WO2020243160 | 12/2020 |
| WO | WO2021011433 | 1/2021 |
| WO | WO2021046232 | 3/2021 |
| WO | WO2021092386 | 5/2021 |
| WO | WO2021102039 | 5/2021 |
| WO | WO2021113353 | 6/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021163611 | 8/2021 |
| WO | WO2021168015 | 8/2021 |
| WO | WO2021168261 | 8/2021 |
| WO | WO20210178199 | 9/2021 |
| WO | WO2021231779 | 11/2021 |
| WO | WO2021247593 | 12/2021 |
| WO | WO2021257795 | 12/2021 |
| WO | WO2021262671 | 12/2021 |
| WO | WO2021262805 | 12/2021 |
| WO | WO2022015667 | 1/2022 |
| WO | WO2022026243 | 2/2022 |
| WO | WO2022026909 | 2/2022 |
| WO | WO2022040453 | 2/2022 |
| WO | WO2022115608 A1 | 2/2022 |
| WO | WO2022115608 A9 | 2/2022 |
| WO | WO2022056309 | 3/2022 |
| WO | WO2022076912 | 4/2022 |
| WO | WO2022094474 | 5/2022 |
| WO | WO2022109339 | 5/2022 |
| WO | WO2022109343 | 5/2022 |
| WO | WO2022132206 | 6/2022 |
| WO | WO2022143221 | 7/2022 |
| WO | WO2022256324 | 12/2022 |
| WO | WO2023034739 | 3/2023 |
| WO | WO2023034789 | 3/2023 |
| WO | WO2023034790 | 3/2023 |
| WO | WO2023034794 | 3/2023 |
| WO | WO2023034872 | 3/2023 |
| WO | WO2023039433 | 3/2023 |
| WO | WO2024097718 | 5/2024 |
| WO | WO2024097719 | 5/2024 |
| WO | WO2024243298 | 11/2024 |

OTHER PUBLICATIONS

Dengl et al., Engineered hapten-binding antibody derivatives for modulation of pharmacokinetic properties of small molecules and targeted payload delivery, 2016, Immunol Rev., 270, 165-177 (Year: 2016).*

Lutz et al., Isolation and analysis of high quality nuclear DNA with reduced organellar DNA for plant genome sequencing and resequencing, 2011, BMC Biotecnology, 11, 1-9 (Year: 2011).*

Goodridge et al., Synthesis of Albumin and Malic Enzyme in Wheat-Germ Lysates and Xenopus laevis Oocytes Programmed with Chicken-Liver Messenger RNA, 1979, Eur. J. Biochem, 96, 1-8 (Year: 1979).*

"List of mammal genera", Wikipedia.com, accessed Apr. 20, 2023. (Year: 2023).*

"Custom Antibody Services", PrecisionAntibody.com, accessed Apr. 16, 2014. (Year: 2014).*

"The Protein Puzzle", Tim Schroder, MaxPlanc Research Mar. 2017, pp. 54-59. (Year: 2017).*

"Murinae", Wikipedia.com, pp. 1-12, accessed Jun. 10, 2024. (Year: 2024).*

"Human genome", Wikipedia.com, accessed Aug. 4, 2021. (Year: 2021).*

Custom Antibody Services, Precision Antibodies, accessed Apr. 16, 2014. (Year: 2014).*

"The complete sequence of a human Y chromosome", Nature, vol. 621, Sep. 14, 2023. (Year: 2023).*

"Monoclonal Antibody Production", Icosagen.com, accessed Apr. 17, 2014. (Year: 2014).*

"Oligonucleotide definition," Merriam-Webster.com; accessed Aug. 23, 2017 (Year: 2017).*

"Oligonucleotide", Wikipedia.com, accessed Feb. 17, 2019 (Year: 2019).*

Advisory Action dated Aug. 25, 2020 in U.S. Appl. No. 15/084,307.

Biosciences Product Catalogue, Dynal® Catalog 1999, Oslo, Norway, 49-51.

Examination Report dated Jul. 6, 2020 in European Patent Application No. 17781265.8.

Examination Report dated Sep. 21, 2020 in European Patent Application No. 18703156.2.

Final Office Action dated Jun. 5, 2020 in U.S. Appl. No. 15/084,307.

Final Office Action dated Aug. 19, 2020 in U.S. Appl. No. 15/875,816.

Final Office Action dated Sep. 14, 2020 in U.S. Appl. No. 16/789,358.

Final Office Action dated Sep. 22, 2020 in U.S. Appl. No. 16/789,311.

Final Office Action dated Sep. 25, 2020 in U.S. Appl. No. 15/055,407.

International Search Report and Written Opinion dated May 18, 2020 in PCT Application No. PCT/US2020/014339.

Kooiker & Xue, "cDNA Library Preparation," Cereal Genomics 2013, 1099, 29-40.

Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.

Non-Final Office Action dated Jun. 8, 2020 in U.S. Appl. No. 15/715,028.

Non-Final Office Action dated Aug. 4, 2020 in U.S. Appl. No. 15/459,977.

Non-Final Office Action dated Aug. 19, 2020 in U.S. Appl. No. 16/374,626.

Non-Final Office Action dated Aug. 25, 2020 in U.S. Appl. No. 14/381,488.

Notice of Allowance dated Sep. 23, 2020 in Korean Patent Application No. 10-2016-7008144.

Notice of Allowance dated Oct. 29, 2020 in U.S. Appl. No. 15/987,851.

Office Action dated Jun. 22, 2020 in Chinese Patent Application No. 201680007351.2.

Office Action dated Jun. 22, 2020 in Chinese Patent Application No. 201680007652.5.

Office Action dated Jun. 23, 2020 in Chinese Patent Application No. 2016800157452.

Office Action dated Jul. 20, 2020 in Japanese Patent Application No. 2018-512152.

(56) References Cited

OTHER PUBLICATIONS

Rhee et al., "Simultaneous detection of mRNA and protein stem cell markers in live cells," BMC Biotechnology 2009, 9(30), 1-10.
Search Report and Written Opinion dated Aug. 26, 2020 in Singapore Patent Application No. 10201806890V.
S.H.Ko, "An 'equalized cDNA library' by the reassociation of short double-stranded cDNAs," Nucleic Acids Res. 1990, 18(19), 5705-5711.
Adey et al., "Rapid, low-input, low-bias construction of shotgun fragment libraries by high-density in vitro transposition," Genome Biology 2010, 11(R19), in 17 pages.
Ahern, "Biochemical, Reagent Kits Offer Scientists Good Return on Investment," The Scientist 1995, 9(15), in 5 pages.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Examination Report dated Dec. 3, 2020 in European Patent Application No. 16719706.0.
Examination Report dated Mar. 25, 2021 in European Patent Application No. 17781265.8.
Examination Report dated Oct. 8, 2021 in European Patent Application No. 18716877.8.
Extended European Search Report dated May 6, 2021 in European Patent Application No. 20207621.2.
Extended European Search Report dated May 28, 2021 in European Patent Application No. 20209777.0.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
FITZGERALD and Grivel, "A Universal Nanoparticle Cell Secretion Capture Assay," Cytometry Part A 2012, 83A(2), 205-211.
GenBank Accession No. NM_000518.5 for *Homo sapiens* hemoglobin subunit beta (HBB), mRNA. 22-Mar. 2021 [online], [retrieved on Apr. 27, 2021], retrieved from the Internet: <URL: www.ncbi.nlm.nih.gov/nuccore/NM_000518.5?report=Genbank (Year: 2021).
Gertz et al., "Transposase mediated construction of RNA-seq libraries," Genome Research 2012, 22, 134-141.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Janeway et al., "Structural variation in immunoglobulin constant regions," Immunology: The Immune System in Health and Disease 1999, 101-103.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, in 1 page.
Mair et al., "A Targeted Multi-omic Analysis Approach Measures Protein Expression and Low- Abundance Transcripts on the Single-Cell Level", Cell Reports 2020, 31(1), 107499, in 20 pages.
New COVID-19 Variants, Centers for Disease Control and Prevention 2021, accessed Jan. 21, 2021, 3 pp.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice of Allowance dated Jun. 10, 2021 in Chinese Patent Application No. 2018800377201.
Notice of Allowance dated Aug. 16, 2021 in Japanese Patent Application No. 2018-512152.
Notice of Allowance dated Sep. 10, 2021 in U.S. Appl. No. 16/535,080.

(56) References Cited

OTHER PUBLICATIONS

Notice of Allowance dated Nov. 16, 2021 in U.S. Appl. No. 16/836,750.
Novus Biologicals, "Fixation and Permeability in ICC IF," Novus Biologicals 2021, 1-3.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794 .
Office Action dated Sep. 14, 2021, in Chinese Patent Application No. 2016800523302.
O'SHEA et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin- Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated May 5, 2021 in U.S. Appl. No. 16/400,886.
Restriction Requirement dated May 28, 2021 in U.S. Appl. No. 16/781,814.
Restriction Requirement dated Jun. 4, 2021 in U.S. Appl. No. 16/551,620.
Restriction Requirement dated Oct. 1, 2021 in U.S. Appl. No. 16/525,054.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Stoeckius et al., "Cell Hashing with barcoded antibodies enables multiplexing and doublet detection for single cell genomics," Genome Biology 2018, 19(224), 1-12.
Summons to Attend Oral Proceedings dated Nov. 16, 2020 in European Patent Application No. 17202409.3.
Takara Bio, "SMARTer Human BCR IgG IgM H/K/L Profiling Kit User Manual," Takara Bio USA Inc. 2019, 1-22.
TotalSeq™-A0251 anti-human Hashtag 1 Antibody, BioLegend ®, Jul. 2018, 1-10.
Trzupek et al., "Discovery of CD80 and CD86 as recent activation markers on regulatory T cells by protein-RNA single-cell analysis", Genome Medicine 2020, 12(1), in 22 pages.
Vestheim et al., "Application of Blocking Oligonucleotides to Improve Signal-to-Noise Ratio in a PCR," Methods in Molecular Biology 2011, 687, 265-274.
Wang et al., "Tagmentation-based whole-genome bisulfite sequencing," Nature Protocols 2013, 8(10), 2022-2032.
Zeberg et al., "The major genetic risk factor for severe COVID-19 is inherited from Neanderthals," Nature 2020, 587(7835), 1-13.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Advisory Action dated Dec. 2, 2019 in U.S. Appl. No. 15/055,407.
Advisory Action dated Nov. 29, 2019 in U.S. Appl. No. 15/084,307.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiDTM System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.

(56) References Cited

OTHER PUBLICATIONS

Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-cell mass cytometry of differential immune and drug responses across a human hematopoietic continuum," Science 2011, 332(6030), 687-696.
BIONUMBERS, "Useful fundamental Nos. in molecular biology," http://bionumbers.hms.harvard.edu/KeyNumbers/aspx, 1-4.
BIOSCRIBE "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "SMART™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Communication of a Notice of Opposition dated Jul. 27, 2016 in European Patent Application No. EP 10762102.1.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in Drosophila," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach, " Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
De Saizieu et al., "Bacterial transcript imaging by hybridization of total RNA to oligonucleotide arrays," Nature Biotechnology 1988, 16, 45-48.

(56) References Cited

OTHER PUBLICATIONS

Decision of Refusal dated Aug. 21, 2017 in Japanese Patent Application No. 2014-558975.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomic's Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomic's Notice of Service for Initial Disclosures served to Opposing Counsel, dated Jun. 7, 2019 in the USDC for the District of Delaware, C.A. 18-1800-RGA, 2 pp.
Defendant 10X Genomic's Request for Oral Argument Under D. Del. LR 7.1.4, dated Apr. 18, 2019 in the USDC for the District of Delaware, C.A. 18-1800-RGA 2 pp.
Defendant 10X Genomic's Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics's Reply Brief in support of its Motion to Dismiss Pursuant to Federal Rule of Civil Procedure 12(b)(6), dated Apr. 12, 2019 in USDC District of Delaware, C.A. No. 18-1800 RGA, 15 pp.
Delley et al., "Combined aptamer and transcriptome sequencing of single cells," bioRxiv 2017, 1-10.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy No. Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Apr. 10, 2017 in European Patent Application No. 14761937.3.
Examination Report dated Apr. 26, 2019 in European Patent Application No. 16710357.1.
Examination Report dated Aug. 2, 2019 in European Patent Application No. 17202409.3.
Examination Report dated Dec. 12, 2018 in European Patent Application No. 16719706.0.
Examination Report dated Dec. 4, 2019 in European Patent Application No. 16719706.0.
Examination Report dated Feb. 19, 2016 in United Kingdom Patent Application No. GB1511591.8.
Examination Report dated Feb. 6, 2019 in European Patent Application No. 13754428.4.
Examination Report dated Jan. 2, 2019 in European Patent Application No. 16757986.1.
Examination Report dated Jan. 27, 2016 in United Kingdom Patent Application No. 1408829.8.
Examination Report dated Jan. 3, 2018 in UK Patent Application No. 1609740.4.
Examination Report dated Jul. 12, 2016 in European Patent Application No. 13755319.4.
Examination Report dated Jul. 20, 2018 in Australian Patent Application No. 2014312208.
Examination Report dated May 12, 2020 in Australian Patent Application No. 2018220004.
Examination Report dated Jul. 24, 2019 in European Patent Application No. 16714081.3.
Examination Report dated Jun. 15, 2016 in United Kingdom Patent Application No. GB1511591.8.
Examination Report dated Jun. 18, 2019 in European Patent Application No. 16710551.9.
Examination Report dated Jun. 8, 2016 in United Kingdom Patent Application No. 1408829.8.
Examination Report dated Mar. 16, 2018 in European Patent Application No. 13754428.4.
Examination Report dated Mar. 18, 2019 in Singapore Patent Application No. 11201405274W.
Examination Report dated Oct. 10, 2017 in European Patent Application No. 14761937.3.
Examination Report dated Oct. 11, 2019 in European Patent Application No. 16757986.1.
Examination Report dated Oct. 24, 2017 in Australian Patent Application No. 2013226081.
Examination Report dated Sep. 26, 2018 in European Patent Application No. 16714081.3.
Examination Report dated Sep. 5, 2018 in European Patent Application No. 16710357.1.
Examination Report dated Feb. 19, 2020 in European Patent Application No. 16710551.9.
Examination Report dated Mar. 18, 2020 in European Patent Application No. 17202409.3.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jul. 17, 2015 in European Patent Application No. 13755319.4.
Extended European Search Report dated Jun. 11, 2018 in European Patent Application No. 16740872.3.
Extended European Search Report dated Mar. 22, 2019 in European Patent Application No. 18195513.9.
Fan et al., "Combinatorial labeling of single cells for gene expression cytometry," SCIENCE 2015, 347(6222), 1258366-1258369.
Fan et al., "Microfluidic digital PCR enables rapid prenatal diagnosis of fetal aneuploidy," Am Obstet Gynecol. 2009, 200, 543e1-543e7.
Fan et al., "Non-invasive Prenatal Measurement of the Fetal Genome," Nature 2012, 487(7407), 320- 324.
Fan et al., "Parallel Genotyping of Human SNPs Using Generic High-density Oligonucleotide Tag Arrays," Genome Research 2000, 10, 853-860.
Fan, "Molecular counting: from noninvasive prenatal diagnostics to whole-genome haplotyping," Doctoral Dissertation, Stanford University 2010, 1-185.
Feldhaus et al., "Oligonucleotide-conjugated beads for transdominant genetic experiments," Nucleic Acids Res. 2000, 28(2), 534-543.

(56) References Cited

OTHER PUBLICATIONS

Final Office Action dated Apr. 11, 2016 for U.S. Appl. No. 14/800,526.
Final Office Action dated Aug. 12, 2016 in U.S. Appl. No. 14/381,488.
Final Office Action dated Apr. 22, 2019 in U.S. Appl. No. 15/987,851.
Final Office Action dated Dec. 4, 2019 in U.S. Appl. No. 15/596,364.
Final Office Action dated Feb. 13, 2017 in U.S. Appl. No. 14/381,488.
Final Office Action dated Feb. 19, 2019 in U.S. Appl. No. 14/381,526.
Final Office Action dated Feb. 4, 2020 in U.S. Appl. No. 15/715,028.
Final Office Action dated Jan. 16, 2020 in U.S. Appl. No. 16/012,584.
Final Office Action dated Jan. 25, 2018 in U.S. Appl. No. 14/381,526.
Final Office Action dated Jan. 29, 2020 in U.S. Appl. No. 14/381,488.
Final Office Action dated Jan. 8, 2020 in U.S. Appl. No. 15/459,977.
Final Office Action dated Jul. 20, 2016 for U.S. Appl. No. 14/281,706.
Final Office Action dated Jul. 20, 2018 in U.S. Appl. No. 15/217,886.
Final Office Action dated Jul. 5, 2018 in U.S. Appl. No. 15/004,618.
Final Office Action dated Mar. 1, 2019 in U.S. Appl. No. 16/012,584.
Final Office Action dated May 10, 2018 in U.S. Appl. No. 14/381,488.
Final Office Action dated May 2, 2019 in U.S. Appl. No. 16/012,635.
Final Office Action dated May 3, 2018 in U.S. Appl. No. 15/046,225.
Final Office Action dated May 3, 2019 in U.S. Appl. No. 15/937,713.
Final Office Action dated May 8, 2017 in U.S. Appl. No. 15/224,460.
Final Office Action dated Nov. 16, 2017 in U.S. Appl. No. 14/381,488.
Final Office Action dated Nov. 16, 2018 in U.S. Appl. No. 15/134,967.
Final Office Action dated Oct. 16, 2017 in U.S. Appl. No. 15/409,355.
Final Office Action dated Oct. 2, 2019 in U.S. Appl. No. 15/084,307.
Final Office Action dated Oct. 6, 2015 in U.S. Appl. No. 14/540,018.
Final Office Action dated Sep. 1, 2015 for U.S. Appl. No. 14/540,029.
Final Office Action dated Sep. 18, 2019 in U.S. Appl. No. 15/055,407.
Final Office Action dated Sep. 24, 2015 for U.S. Appl. No. 14/540,007.
Final Office Action dated Mar. 9, 2020 in U.S. Appl. No. 15/987,851.
Final Office Action dated Apr. 28, 2020 in U.S. Appl. No. 15/134,967.
First Action Interview Office Action Summary dated Jan. 25, 2019 in U.S. Appl. No. 15/987,851.
First Action Interview Pilot Program Pre-Interview Communication dated Oct. 15, 2018 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct mutation analysis by high-throughput sequencing: from germline to low-abundant, somatic variants," Mutat Res. 2012, 729(1-2), 1-15.
Gundry et al., "Direct, genome-wide assessment of DNA mutations in single cells," Nucleic Acids Research 2011, 40(5), 2032-2040.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Aug. 15, 2019 in PCT Application No. PCT/US2018/014385.
International Preliminary Report on Patentability dated Mar. 26, 2019 in PCT Application No. PCT/US2017/053331.
International Search Report and Written Opinion dated Aug. 16, 2013 for PCT Application No. PCT/US2013/027891.
International Search Report and Written Opinion dated Sep. 28, 2016 in PCT Application No. PCT/US2016/028694.
International Search Report and Written Opinion dated Aug. 7, 2017 in PCT Application No. PCT/US2017/034576.
International Search Report and Written Opinion dated Aug. 9, 2016 in PCT Application No. PCT/US2016/019971.

(56) References Cited

OTHER PUBLICATIONS

International Search Report and Written Opinion dated Dec. 19, 2014 in PCT Application No. PCT/US2014/059542.
International Search Report and Written Opinion dated Dec. 4, 2019 in PCT Application No. PCT/US2019/053868.
International Search Report and Written Opinion dated Dec. 5, 2016 in PCT Application No. PCT/US2016/024783.
International Search Report and Written Opinion dated Feb. 3, 2015 in PCT Application No. PCT/US2014/053301.
International Search Report and Written Opinion dated Jan. 27, 2020 in PCT Application No. PCT/US2019/048179.
International Search Report and Written Opinion dated Jan. 31, 2017 in PCT Application No. PCT/US2016/050694.
International Search Report and Written Opinion dated Jul. 16, 2018 in PCT Application No. PCT/US2018/024602.
International Search Report and Written Opinion dated Jun. 14, 2013 in PCT Application No. PCT/US2013/028103.
International Search Report and Written Opinion dated Jun. 17, 2016 in PCT Application No. PCT/US2016/019962.
International Search Report and Written Opinion dated Jun. 24, 2019 in PCT Application No. PCT/US2019/030175.
International Search Report and Written Opinion dated Jun. 6, 2012 in PCT Application No. PCT/US2011/065291.
International Search Report and Written Opinion dated Jun. 9, 2016 in PCT Application No. PCT/US2016/022712.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated May 3, 2016 in PCT Application No. PCT/US2016/018354.
International Search Report and Written Opinion dated May 7, 2012 for PCT Application No. PCT/IB2011/003160.
International Search Report and Written Opinion dated Nov. 27, 2019 in PCT Application No. PCT/US2019/046549.
International Search Report and Written Opinion dated Oct. 16, 2019 in PCT Application No. PCT/US2019/030245.
International Search Report and Written Opinion dated Sep. 27, 2016 in PCT Application No. PCT/US2016/034473.
International Search Report and Written Opinion dated Sep. 8, 2017 in PCT Application No. PCT/US2017/030097.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara et al., "Accurate sampling and deep sequencing of the HIV-1 protease gene using a Primer ID," PNAS 2011, 108(50), 20166-20171.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Application of multi-omics in single cells," Ann Biotechnol. 2018, 2(1007), 1-8.
Kang et al., "Targeted sequencing with enrichment PCR: a novel diagnostic method for the detection of EGFR mutations," Oncotarget 2015, 6(15), 13742-13749.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336- 343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute numbers of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., "VarScan: variant detection in massively parallel sequencing of individual and pooled samples," Bioinformatics 2009, 25(17), 2283-2285.
Kolodziejczyk et al., 'The Technology and Biology of Single-Cell RNA Sequencing, Molecular Cell 2015, 58, 610-620.
Konig et al., iCLIP reveals the function of hnRNAP particles in splicing at individual nucleotide resolution, Nature Structural & Molecular Biology 2010, 17(7), 909-916.
Kotake et al., "A simple nested RT-PCR method for quantitation of the relative amounts of multiple cytokine mRNAs in small tissue samples," Journal of Immunological Methods 1996, 199, 193-203.
Kozlov et al., "A high-complexity, multiplexed solution-phase assay for profiling protease activity on microarrays," Comb Chem High Throughput Screen 2008, 11(1), 24-35.

(56) References Cited

OTHER PUBLICATIONS

Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Highly Multiplexed Subcellular RNA Sequencing in Situ," Science 2014, 343, 1360-1363.
Lee et al., "Large-scale arrays of picolitre chambers for single-cell analysis of large cell populations," Lab Chip 2010, 10, 2952-2958.
Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Letter to Judge Richard G. Andrews Requesting a Rule 16 Conference, dated Apr. 15, 2019 in the USDC for the District of Delaware, C.A. 18-1800 (RGA), 1 pp.
Lin et al., "Self-Assembled Combinatorial Encoding Nanoarrays for Multiplexed Biosensin," Nano Lett. 2007, 7 (2), 507-512.
Liu et al., "Single-cell transcriptome sequencing: recent advances and remaining challenges," F1000Research 2016, 5(F1000 Faculty Rev)(182), 1-9.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," Oct. 2, 2018, 1 p.
Lucito et al., "Representational Oligonucleotide Microarray Analysis: A High-Resolution Method to Detect Genome Copy No. Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Maamar et al., "Noise in Gene Expression Determines Cell Fate in *Bacillus subtilis*," Science 2007, 317, 526-529.
Macaulay et al., "G&T-seq: parallel sequencing of single-cell genomes and transcriptomes," Nature Methods 2015, 1-7.
Macaulay et al., "Single Cell Genomics: Advances and Future Perspectives," PLoS Genetics 2014, 10(1), 1-9.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," Bio Techniques 2008, 45(1), 95-97.
Makrigiorgos et al., "A PCR-Based amplification method retaining quantities difference between two complex genomes," Nature Biotech 2002, 20(9), 936-939.
Marcus et al., 2006, "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
Mccloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Apr. 11, 2016 in U.S. Appl. No. 14/472,363.
Non-Final Office Action dated Apr. 6, 2018 in U.S. Appl. No. 15/603,239.
Non-Final Office Action dated Aug. 17, 2016 for U.S. Appl. No. 14/800,526.
Non-Final Office Action dated Aug. 20, 2019 in U.S. Appl. No. 15/715,028.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Feb. 18, 2015 for U.S. Appl. No. 14/540,007.
Non-Final Office Action dated Feb. 19, 2019 in U.S. Appl. No. 14/381,526.
Non-Final Office Action dated Feb. 26, 2015 for U.S. Appl. No. 14/540,029.
Non-Final Office Action dated Feb. 5, 2020 in U.S. Appl. No. 15/875,816.
Non-Final Office Action dated Jan. 12, 2018 in U.S. Appl. No. 15/217,886.

(56) References Cited

OTHER PUBLICATIONS

Non-Final Office Action dated Jan. 14, 2019 in U.S. Appl. No. 16/219,553.
Non-Final Office Action dated Jan. 17, 2020 in U.S. Appl. No. 15/084,307.
Non-Final Office Action dated Jan. 19, 2017 in U.S. Appl. No. 15/055,445.
Non-Final Office Action dated Jan. 7, 2019 in U.S. Appl. No. 15/055,407.
Non-Final Office Action dated Jan. 9, 2018 in U.S. Appl. No. 15/217,896.
Non-Final Office Action dated Jul. 25, 2018 in U.S. Appl. No. 15/108,268.
Non-Final Office Action dated Jul. 28, 2017 in U.S. Appl. No. 14/975,441.
Non-Final Office Action dated Jul. 9, 2019 in U.S. Appl. No. 15/596,364.
Non-Final Office Action dated Jun. 17, 2019 in U.S. Appl. No. 14/381,488.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Mar. 19, 2015 in U.S. Appl. No. 14/540,018.
Non-Final Office Action dated Mar. 19, 2019 in U.S. Appl. No. 15/046,225.
Non-Final Office Action dated Mar. 24, 2017 in U.S. Appl. No. 15/409,355.
Non-Final Office Action dated Mar. 8, 2018 in U.S. Appl. No. 15/608,780.
Non-Final Office Action dated May 10, 2016 in U.S. Appl. No. 14/381,488.
Non-Final Office Action dated May 13, 2016 in U.S. Appl. No. 14/508,911.
Non-Final Office Action dated May 15, 2019 in U.S. Appl. No. 15/084,307.
Non-Final Office Action dated May 23, 2019 in U.S. Appl. No. 15/459,977.
Non-Final Office Action dated May 7, 2015 for U.S. Appl. No. 13/327,526.
Non-Final Office Action dated Nov. 1, 2017 in U.S. Appl. No. 15/667,125.
Non-Final Office Action dated Nov. 26, 2018 in U.S. Appl. No. 15/937,713.
Non-Final Office Action dated Nov. 29, 2019 in U.S. Appl. No. 15/937,713.
Non-Final Office Action dated Nov. 5, 2018 in U.S. Appl. No. 16/038,790.
Non-Final Office Action dated Nov. 9, 2017 in U.S. Appl. No. 15/004,618.
Non-Final Office Action dated Oct. 11, 2016 in U.S. Appl. No. 15/224,460.
Non-Final Office Action dated Oct. 25, 2018 in U.S. Appl. No. 16/012,584.
Non-Final Office Action dated Oct. 3, 2013 in U.S. Appl. No. 12/969,581.
Non-Final Office Action dated Oct. 4, 2018 in U.S. Appl. No. 15/260,106.
Non-Final Office Action dated Sep. 18, 2019 in U.S. Appl. No. 16/194,819.
Non-Final Office Action dated Sep. 26, 2016 in U.S. Appl. No. 15/167,807.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Mar. 17, 2020 in U.S. Appl. No. 15/055,407.
Non-Final Office Action dated Mar. 12, 2020 in U.S. Appl. No. 16/789,358.
Non-Final Office Action dated Mar. 26, 2020 in U.S. Appl. No. 16/789,311.
Non-Final Office Action dated Mar. 26, 2020 in U.S. Appl. No. 16/012,635.
Notice of Allowability dated Jun. 19, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Dec. 27, 2019 in U.S. Appl. No. 15/260,106.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 21, 2014 for U.S. Appl. No. 12/969,581.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Mar. 20, 2019 in U.S. Appl. No. 16/219,553.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Sep. 24, 2019 in U.S. Appl. No. 15/217,886.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice of Opposition dated Jul. 9, 2015 for European Patent Application No. 11810645.9.
Notice of Reason for Refusal dated Nov. 21, 2019 in Korean Patent Application No. 10-2016-7008144.
Notice of Reasons for Rejection dated Apr. 2, 2018 in Japanese Patent Application No. 2014-558975.
Notice of Reasons for Rejection dated Aug. 31, 2018 in Japanese Patent Application No. 2016-520632.
Notice of Reasons for Rejection dated Dec. 28, 2016 in Japanese Patent Application No. 2014-558975.
Notice of Reasons for Rejection dated Dec. 5, 2018 in Japanese Patent Application No. 2017-245295.
Notice of Reasons for Rejection dated Jul. 30, 2018 in Japanese Patent Application No. 2016-537867.
Notice of Reasons for Rejection dated Feb. 25, 2020 in Japanese Patent Application No. 2019-014564.
Notice of Reasons for Refusal dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.

(56) References Cited

OTHER PUBLICATIONS

Office Action dated Dec. 13, 2018 in Canadian Patent Application No. 2,865,575.
Office Action dated Dec. 19, 2017 in Chinese Patent Application No. 201480061859.1.
Office Action dated Dec. 27, 2016 in Chinese Patent Application No. 201380022187.9.
Office Action dated Feb. 15, 2018 in Canadian Patent Application No. 2,865,575.
Office Action dated Feb. 17, 2017 in Canadian Patent Application No. 2,865,575.
Office Action dated Jan. 2, 2019 in Chinese Patent Application No. 201480059505.3.
Office Action dated Jul. 14, 2017 in Chinese Patent Application No. 201380022187.9.
Office Action dated Jun. 6, 2016 in Chinese Patent Application No. 201380022187.9.
Office Action dated Sep. 7, 2018 in Chinese Patent Application No. 201480061859.1.
Office Action dated Mar. 4, 2020 in Canadian Patent Application No. 2,865,575.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Scheduling ADR Mediation Teleconference, filed May 13, 2019 in the USDC for the District of Delaware, C.A. 18-1800-RGA, 4pp.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Ozkumur et al., "Inertial Focusing for Tumor Antigen-Dependent and—Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy No. variants using integrated high-resolution array CGH and massively parallel DNA sequencing," Nat Genet. 2010, 42(5), 400-405.
Patanjali et al., "Construction of a uniform-abundance (normalized) CNDA library, " Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes andsample integrity: BestKeeper—Excel-based tool using pair-wise correlations," Biotechnology Letters, 26(6), 505-515.
Picelli et al., "Single-cell RNA-sequencing: The future of genome biology is now," RNA Biology 2017, 14(5), 637-650.
Picelli et al., "Tn5 transposase and tagmentation procedures for massively scaled sequencing projects," Genome Research 2014, 24(12), 2033-2040.
Pihlak et al., "Rapid genome sequencing with short universal tiling probes," Nature Biotechnology 2008, 26, 1-9.
Pinkel et al., "Comparative Genomic Hybridization," Annual ReviewGenetics 2005, 6, 331-354.
Pleasance et al., "A small-cell lung cancer genome with complex signatures of tobacco exposure," Nature 2010, 463(7278), 184-190.
Plessy et al., "Population transcriptomics with single-cell resolution: a new field made possible bymicrofluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "Bar Codes" for Tracking the Origins of Expressed Sequence Tagsfrom a Maize cDNA Library Constructed Using Multiple mRNA Sources," Plant Physiol. 2003, 133, 475-481.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Raj et al., "Stochastic mRNA synthesis in mammalian cells," PLoS Biol. 2006, 4(10) 1707-1719.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Jun. 19, 2019 in U.S. Appl. No. 15/596,364.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Sep. 20, 2019 in U.S. Appl. No. 15/875,816.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody—DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Sebat et al., "Large-Scale Copy No. Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.

(56) References Cited

OTHER PUBLICATIONS

Shiroguchi et al., "Digital RNA sequencing minimizes sequence-dependent bias and amplification noise with optimized single-molecule barcodes," Proc Natl Acad Sci 2012, 109(4):1347-1352.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy No. variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition dated Jul. 21, 2016 filed against European Patent No. EP2414548B1.
Statement of Opposition filed against European Patent No. EP2414548B1 on Jul. 26, 2016.
Statement of Opposition of Strawman Limited filed against European Patent No. EP2414548B1 on Jul. 19, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Sun et al., "Ultra-deep profiling of alternatively spliced Drosophila Dscam isoforms by circularization-assisted multi-segment sequencing," EMBO J. 2013, 32(14), 2029-2038.
Takahashi et al., "Novel technique of quantitative nested real-time PCR assay for mycobacterium tuberculosis DNA," Journal of Clinical Microbiology 2006, 44, 1029-1039.
Tan et al., "Genome-wide comparison of DNA hydroxymethylation in mouse embryonic stem cells andneural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy No. estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Characterization of the Yeast Transcriptome," Cell 1997, 88, 243-251.
Velculescu et al., "Serial Analysis of Gene Expression," Science 1995, 270(5235), 484-487.
Vogelstein et al., "Digital PCR," Proc. Natl. Acad. Sci. 1999, 96, 9236-9241.
Vollbrecht et al., "Validation and comparison of two NGS assays for the detection of Egfr T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Advances and applications of single-cell sequencing technologies," Molecular Cell 2015, 58, 598-609.
Wang et al., "Combining Gold Nanoparticles with Real-Time Immuno-PCR for Analysis of HIV p24 Antigens," Proceedings of ICBBE 2007, 1198-1201.
Wang et al., "iCLIP predicts the dual splicing effects of TIA-RNA interactions," PLoS Biol 2010, 8(10), e1000530, 1-16.
Wang et al., "RNA-Seq: a revolutionary tool for transcriptomics," Nature Reviews Genetics 2009, 10(1), 57-63.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in Saccharomyces cerevisiae," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.

(56) References Cited

OTHER PUBLICATIONS

Yandell et al., "A probabilistic disease-gene finder for personal genomes," Genome Res. 2011, 21(9), 1529-1542.
Ye et al., Fluorescent microsphere-based readout technology for multiplexed human single nucleotide polymorphism analysis and bacterial identification, Human Mutation 2001, 17(4), 305-316.
Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.
Zhang et al., "DNA-based hybridization chain reaction for amplified bioelectronic signal and ultrasensitive detection of proteins," Anal Chem. 2012, 84, 5392-5399.
Zhang et al., "The impact of next-generation sequencing on genomics," J Genet Genomics 2011, 38(3), 95-109.
Zhao et al., "Homozygous Deletions and Chromosome Amplifications in Human Lung CarcinomasRevealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by Maldi-Tof Ms," Mol. BioSyst. 2012, 8, 2395-2404.
Zhu et al., "Reverse Transcriptase Template Switching: A SMART Approach for Full-Length cDNA Library Construction," BioTechniques 2001, 30(4), 892-897.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Chang et al., "Single-cell protein and gene expression profiling of stem memory T cells by BD Ab-seq," Annual Joint Meeting of the American Society for Cell Biology and the European Molecular Biology Organization 2017, 28(26), P1896.
Chen et al., "High-throughput sequencing of the transcriptome and chromatin accessibility in the same cell," Nature Biotechnology 2019, 37, 1452-1457.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 8, 2022 in Australian Patent Application No. 2018281745.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
Jacobsen et al., "33rd Annual Meeting & Pre-Conference Programs of the Society for Immunotherapy of Cancer," Journal for Immunotherapy of Cancer 2018, 6(S1), 7-11.
Lake et al., "Integrative single-cel l analysis of tra nscri ptiona I and epigenetic states in the human adult brain," Nature Biotechnology 2018, 36(1), 70-80.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Notice of Allowance dated Dec. 7, 2021 in Chinese Patent Application No. 201680007652.
Notice of Allowance dated Jan. 24, 2022 in Korean U.S. Appl. No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 7, 2022 in Singapore Patent Application No. 10201806890V.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 27, 2022 in U.S. Appl. No. 16/400,886.
Nowak et al., "Does the KIR2DS5 gene protect from some human diseases?," PLoS One 2010, 5(8), in 6 pages.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 2017800587991.
Office Action dated Feb. 9, 2022 in Japanese Patent Application No. 2019-540515 .
Office Action dated Mar. 7, 2022 in Korean Patent Application No. 10-2022-7004715.
Restriction Requirement dated Dec. 27, 2021 in U.S. Appl. No. 16/747,737.
Yang & Zhao, "Quantitative Analysis of Nonoxynol-9 in Blood," Contraception 1991, 43(2), 161-166.
Buenrosto et al., "Transposition of native chromatin for multimodal regulatory analysis and personal epigenomics," Nat Methods 2013, 10(12), 1213-1218.
Buenrosto et al., "ATAC-seq: A Method for Assaying Chromatin Accessibility Genome-Wide," Curr Protoc Mol Biol 2016, 109, 1-21.
De Simone et al., "Single Cell T Cell Receptor Sequencing: Techniques and Future Challenges," Frontiers in Immunology 2018, 9(1638), 1-7.
Dovgan et al., "Antibody—Oligonucleotide Conjugates as Therapeutic, Imaging, and Detection Agents," Bioconjugate Chem. 2019, 30, 2483-2501.

(56) References Cited

OTHER PUBLICATIONS

Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Examination Report dated Apr. 7, 2022 in Singapore Patent Application No. 10201806890V.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
Lee et al., "Comparison of Surface Markers between Human and Rabbit Mesenchymal Stem Cells," PLoS ONE 2014, 9(11), in 10 pages.
Minnoye et al., "Chromatin accessibility profiling methods," Nature Reviews Method Primers 2021, 1-24.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.
Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Notice of Allowance dated Apr. 26, 2022 in Chinese Patent Application No. 201780058799.1.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Notice of Allowance dated Jan. 31, 2023 in U.S. Appl. No. 16/747,737.
Office Action dated May 5, 2022 in European Patent Application No. 19787547.9.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Office Action dated Feb. 8, 2023 in Australian Patent Application No. 2017331459.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Restriction Requirement dated Dec. 23, 2022 in U.S. Appl. No. 17/531,618.
Restriction Requirement dated Jan. 20, 2023 in U.S. Appl. No. 17/373,519.
10X Genomics, Inc., 2022, "Chromium Fixed RNA Profiling Reagent Kits," 10xGenomics.com, User Guide, in 95 pages.
10x Genomics, Inc., LIT099 Product-Sheet "Chromium Single Cell Multiome ATAC + Gene Expression" digital, 2021.
AAT Bioquest, Calcein-Based Cell Viability Assays, AssayWise Letters, 2016, 5(1), 1-16.
AccuPrimeTM Pfx DNA polymerase brochure, Invitrogen pp. 1-4 (Year 2010).
Arguel et al., "A cost effective 5' selective single cell transcriptome profiling approach with improved UMI design," Nucleic Acids Research 2017, 45(7), e48, in 11 pages.
Armbrecht, et al. "Single-cell protein profiling in microchambers with barcoded beads", Microsystems & Nanoengineering, 2019, 5:55.
Attar, Moustafa, et al. "A practical solution for preserving single cells for RNA sequencing." Scientific Reports 8.1 (2018): 2151.

(56) References Cited

OTHER PUBLICATIONS

Biotium, Fura-2, AM Ester, Biotium, 2023, 1-3. Obtained online at: https://biotium.com/product/fura-2-am-ester/ on Feb. 14, 2023.
Blumenthal, "Rna Replication: Function and Structure of Qb-Replicase" Ann. Rev. Biochem. 1979 48:525-48.
Burger et al., "Maximizing mutagenesis with solubilized CRISPR-Cas9 ribonucleoprotein complexes," Development 2016, vol. 143, No. 11, 2025-2037.
Cahill et al., "Polymerase Chain Reaction and Qb Replicase Amplification" Clin._Chem. 1991, 37(9), 1482-1485.
Cao et al., "Supplementary Materials, Comprehensive Single-Cell Transcriptional Profiling of a Multicellular Organism," Science (2017), 337, 1-70.
Carninci et al., "Normalization and Subtraction of Cap-Trapper-Selected cDNAs to Prepare Full-Length cDNA Libraries for Rapid Discovery of New Genes," Genome Research 2000, 10:1617-1630.
CG000209_Chromium_NextGEM_SingleCell_ATAC_ReagentKits_v1.1_UserGuide_RevG_2022, Aug. 2022.
CG000496_Chromium_NextGEM_SingleCell_ATAC_ReagentKits_v2_UserGuide_RevB 2022, Aug. 2022.
CG000505_Chromium_Nuclei_Isolation_Kit_UG_RevA_2022, May 2022.
Chen et al., "Single-Cell Protein Secretion Detection and Profiling", Annual Reviews, Anal. Chem, 2019, 12, 431-449.
Choi et al., "Programmable in situ amplification for multiplexed imaging of mRNA expression," Nature Biotechnology (2010), 28(11), 1208-1212.
Delebecque et al. "Designing and using RNA scaffolds to assemble proteins in vivo". Nature protocols, 2012, 7(10), 1797-1807.
Delley et al., "Combined aptamer and transcriptome sequencing of single cells," Scientific Reports (2018), 8(2919), 1-8.
Dey et al., "Integrated genome and transcriptome sequencing of the same cell", Nature Biotechnology, 33(3) 2015, 285.
Dickey and Giangrande. "Oligonucleotide Aptamers: A Next-Generation Technology for the Capture and Detection of Circulating Tumor Cells." Methods, 2016 97:94-103.
Dua, et al. "Patents on SELEX and therapeutic aptamers. Recent patents on DNA & gene sequences," 2008, 2( 3), 172-186.
Dunker et al., "Single-cell transcriptomics enters the age of mass production," Molecular Cell. 58:563-564, May 21, 2015.
Elghanian, Robert, et al. "Selective colorimetric detection of polynucleotides based on the distance-dependent optical properties of gold nanoparticles." Science 277.5329 (1997): 1078-1081.
Eulberg, et al. "Development of an automated in vitro selection protocol to obtain RNA-based aptamers: identification of a biostable substance P antagonist," Nucleic acids research, 2005, 33(4).
Fathi, P. Design and Characterization of SSDNA Aptamer Candidates to Bind Bacteroides Fragilis Toxin Subtypes BFT-1 and BFT-2 (Doctoral dissertation, Johns Hopkins University). 2017.
Fisher Scientific, Invitrogen "Calcein AM, Cell-Permanent Green and Blue Dyes", Invitrogen, 2024, 1-4.
Gao et al., "The Comparison of Two Single-cell Sequencing Platforms: BD Rhapsody and 10x Genomics Chromium," Current Genomics 2020, 21(8), 602-609.
Gerlach, et al., "Combined quantification of intracellular (phospho-) proteins and transcriptomics from fixed single cells", Scientific Reports, 2019 vol. 9:1469, pp. 1-10.
Granja, Jeffrey M., et al. "Single-cell multiomic analysis identifies regulatory programs in mixed-phenotype acute leukemia." *Nature biotechnology* 37.12 (2019): 1458-1465.
Haddock, "Dapi Permeability," Flow Post-Itsm, Dec. 2020, obtained on httpswi.mit.edusitesdefaultfiles2021-05202012DAPI_Permeability.pdf.
Henry, et al., "Cell type specific genomics of Drosophila neuron" Nucleic Acids Research, vol. 40, No. 19, 2012.
Hoinka and Przytycka. "AptaPLEX-A Dedicated, Multithreaded Demultiplexer for Ht-Se Lex Data." Methods, 2016, 106:82-85.
Illumina, "Data Processing of Nextera Mate Pair Reads on Illumina Sequencing Platforms", Data Processing Technical Note from 2012.
Illumina, "Estimating Sequencing Coverage" Technical Note: Sequencing from 2014.
Illumina, "Optimizing Cluster Density on Illumina Sequencing Systems", Publication No. 770- 2014-031, 2016.
Invitrogen, "The attraction is simply magnetisk, Dynabeads® Streptavidin products and applications" Invitrogen, 2010, 1-8.
Jara-Acevedo et al., "Exosome beads array for multiplexed phenotyping in cancer," Journal of Proteomics 2019, 198(30), 87-97.
Jiang et al., "Whole transcriptome analysis with sequencing: methods, challenges and potential solutions," Cellular and Molecular Life Sciences 2015; 72: 3425-3439.
Jovelet et al., "Circulating Cell-Free Tumor DNA Analysis of 50 Genes by Next-Generation Sequencing in the Prospective MOSCATO Trial," Clinical Cancer Research (2016), 22(12), 2960-2968.
Kalamasz et al., "Optimization of Human T-Cell Expansion Ex Vivo Using Magnetic Beads Conjugated with Anti-CD3 and Anti-CD28 Antibodies," Journal of Immunother 2004, 27(5), 405-418.
Ku, et al. "Nucleic Acid Aptamers: An Emerging Tool for Biotechnology and Biomedical Sensing." Sensors, 2015, 15, 16281-16313.
Kurschat et al., "Optimizing splinted ligation of highly structured small RNAs", RNA, Cold Spring Harbor Laboratory Press, US, vol. 11, No. 12. Dec. 2005, 1909-1914.
Lao et al., "mRNA-Sequencing Whole Transcriptome Analysis of a Single Cell on the SOLID tm System," Journal of Biomolecular Techniques 2009, 20:266-271.
Lausted et al., "POSaM: a fast, flexible, open-source, inkjet oligonucleotide synthesizer and microarrayer," Genome Biol 2004, 5(8), R58.1-R58.17.
Lebl et al. "A High-Complexity, Multiplexed Solution-Phase Assay for Profiling Protease Activity in Microarrays", Combinatorial Chemistry and High Throughput Screening, 2008, 11(1), 24-35.
Lee et al., "Mutant Enrichment with 3'-Modified Oligonucleotides: A Practical PCR Method for Detecting Trace Mutant DNAs," The Journal of Molecular Diagnostics 2011; 13: 657-668.
Levay, et al. "Identifying High-Affinity Aptamer Ligands with Defined Cross-Reactivity Using High-Throughput Guided Systematic Evolution of Ligands by Exponential Enrichment." Nucleic acids research 12 2015, 43.
Liu et al., "Identification of lung adenocarcinoma-specific exosome RNAs in peripheral blood by RNA-Seq analysis," European Review for Medical and Pharmacological Sciences 2020, 24(4), 1877-1886.
Lustig et al., Long poly(A) tracts in the human genome are associated with the Alu family of repeated elements J of Molecular Biology 180 :753-759 1984.
Ma, "Affinity-based isolation of tagged nuclei from Drosophila tissues for gene expression analysis," Journal of Visualized Experiments (2014), 85, 1-9.
Mairal et al. "Aptamers: Molecular Tools for Analytical Applications." Analytical and bioanalytical chemistry 2008, 390: 989-1007.
Matula et al., "Single-Cell Analysis Using Droplet Microfluidics," Adv Biosyst. Jan. 2020; 4(1), 28 pages.
Mayer et al., "Obtaining deeper insights into microbiome diversity using a simple method to block host and nontargets in amplicon sequencing," Molecular Ecology Resources 2021, 21(6), 1952-1965.
Medepalli, Krishnakiran, et al. "A new technique for reversible permeabilization of live cells for intracellular delivery of quantum dots." *Nanotechnology* 24.20 (2013): 205101.
Nair, et al., "Enzymatic cleavage of uracil-containing single-stranded DNA linkers for the efficient release of affinity-selected circulating tumor cells" Chem Commun (Camb). Feb. 21, 2015 ;51 (15):3266-9.
Nitsch et al., "Determination of In Vitro Membrane Permeability by Analysis of Intracellular and Extracellular Fluorescein Signals in Renal Cells," In Vivo (2019), 33, 1767-1771.
Ogawa, T. et al., "The Efficacy and further functional advantages of random-base molecular barcodes for absolute and digital quantification of nucleic acid molecules", Sci Rep 7, 2017 12576.
Picelli et al., "Full-length RNA-seq from single cells using Smart-seq2," Nat Protoc 2014, 9, 171-181.
Rittie et al., "Enzymes used in molecular biology: a useful guide," J. Cell Commun. Signal. 2008, 2:25-45.

(56) References Cited

OTHER PUBLICATIONS

Rohland et al., "Cost-Effective, High-Throughput DNA Sequencing Libraries for Multiplexed Target Capture," Genome Research 2012, 22:939-946.
Scotto-Lavino et al., "3' End cDNA amplification using classic RACE," Nature Protocols 2006, vol. 1, 2742-2745.
Sefi et al., "Amplication of GC-rich Putative Mouse PeP Promoter using Betaine and DMSO in Ammonium Sulfate Polymerase Chain Reaction Buffer," Avicenna J. Med. Biotechnol. Oct. 2012; 4(4):206-9.
Sharma et al., "Immunoaffinity-based isolation of melanoma cell-derived exosomes from plasma of patients with melanoma," Journal of Extracellular Vesicles 2018, 7(1), 1435138.
Singh, R., "Target Enrichment Approaches for Next-Generation Sequencing Applications in Oncology", Diagnostics, vol. 12, No. 7, Jun. 2022 p. 1539.
Spanova et al., "Magnetic hydrophilic methacrylate-based polymer microspheres designed for polymerase chain reaction applications", Journal of Chromatography vol. 800, 2004, 27-32.
Tsompana et al., "Chromatin Accessibility: a window into the genome" Epigenetics & Chromatin 2014 7:33.
Uellendahl-Werth et al., "A benchmark of hemoglobin blocking during library preparation for mRNA Sequencing of human blood samples," Scientific Reports 2020, 10(1), 5630.
Van Nieuwerburgh, et al., "Quantitative Bias in Illumina TruSeq and a Novel Post Amplification Barcoding Strategy for Multiplexed DNA and Small RNA Deep Sequencing", PLOS ONE, vol. 6, No. 10, 2011.
Wang et al., "Development of Multicolor Flow Cytometry Calibration Standards: Assignment of Equivalent Reference Fluorophores (ERF) Unit" J. Res. Natl. Inst. Stand. Technol. 2011 116, 671-683.
Wangsanuwat et al., "Efficient and cost-effective bacterial mRNA sequencing from low input samples through ribosomal RNA depletion," BMC Genomics 2020, 21(1), 1-12.
Winter, E, Varshavsky A. "A Dna binding protein that recognizes oligo(dA).oligo(dT) tracts." EMBO J. Jun. 1989;8(6):1867-77.
Wu & Lambowitz, "Facile single-stranded DNA sequencing of human plasma DNA via thermostable group II intron reverse transcriptase template switching," Scientific Reports 2017, 7(8421), 1-14.
Wu, et al., "Time-resolved assessment of single-cell protein secretion by sequencing", bioRxiv, Dec. 21, 2021.
Wulf et al., "Non-templated addition and template switching by Moloney murine leukemia virus (MMLV)-based reverse transcriptases co-occur and compete with each other", J. Biol. Chem. 2019, 294(48) 18220-18231.
Xiang, Charlie C., et al. "Using DSP, a reversible cross-linker, to fix tissue sections for immunostaining, microdissection and expression profiling." Nucleic acids research 32.22 (2004).
Yang et al., HHS Public Access, Author Manuscript, Getting Across the Cell Membrane: An Overview for Small Molecules, Peptides, and Proteins, 2015, 1-25.
Zheng, et al. "Aptamer-Functionalized Barcode Particles for the Capture and Detection of Multiple Types of Circulating Tumor Cells." Advanced materials (Weinheim), 2014, 26, 7333-7338.
ZHOU and ROSSI. "Aptamers as Targeted Therapeutics: Current Potential and Challenges." Nature reviews. Drug discovery, 2017, 16:181-202.
Zhulidov et al., "Simple cDNA normalization using kamchatka crab duplex-specific nuclease," Nucleic Acids Research. 2004, 32(3)e37.
Advisory Action dated Jul. 9, 2019 in U.S. Appl. No. 15/260,106.
Advisory Action dated Jul. 27, 2023 in U.S. Appl. No. 17/163,177.
Advisory Action dated May 31, 2023 in U.S. Appl. No. 16/789,311.
Advisory Action dated Nov. 15, 2024 in U.S. Appl. No. 16/789,311.
Corrected Notice of Allowability dated Aug. 25, 2023 in U.S. Appl. No. 16/459,444.
Corrected Notice of Allowability dated Mar. 27, 2024 in U.S. Appl. No. 17/370,923.
Final Office Action dated Apr. 25, 2023 in U.S. Appl. No. 16/525,054.
Final Office Action dated Apr. 9, 2024 in U.S. Appl. No. 17/147,283.
Final Office Action dated Aug. 21, 2025 in U.S. Appl. No. 17/684,289.
Final Office Action dated Dec. 27, 2023 in U.S. Appl. No. 17/174,249.
Final Office Action dated Dec. 21, 2022 in U.S. Appl. No. 16/747,737.
Final Office Action dated Dec. 9, 2024 in U.S. Appl. No. 17/373,653.
Final Office Action dated Feb. 19, 2025 in U.S. Appl. No. 17/174,249.
Final Office Action dated Feb. 21, 2023 in U.S. Appl. No. 16/551,620.
Final Office Action dated Feb. 21, 2025 in U.S. Appl. No. 16/525,054.
Final Office Action dated Feb. 21, 2025 in U.S. Appl. No. 17/592,271.
Final Office Action dated Feb. 27, 2025 in U.S. Appl. No. 17/157,872.
Final Office Action dated Feb. 9, 2024 in U.S. Appl. No. 17/151,058.
Final Office Action dated Jan. 24, 2025 in U.S. Appl. No. 17/531,555.
Final Office Action dated Jan. 7, 2025 in U.S. Appl. No. 17/147,283.
Final Office Action dated Jul. 18, 2025 in U.S. Appl. No. 17/151,058.
Final Office Action dated Jul. 24, 2024 in U.S. Appl. No. 17/684,289.
Final Office Action dated Jul. 24, 2024 in U.S. Appl. No. 18/053,603.
Final Office Action dated Jul. 9, 2025 in U.S. Appl. No. 16/551,620.
Final Office Action dated Jun. 18, 2024 in U.S. Appl. No. 16/551,620.
Final Office Action dated Jun. 5, 2025 in U.S. Appl. No. 18/194,590.
Final Office Action dated Jun. 8, 2023 in U.S. Appl. No. 17/147,283.
Final Office Action dated Mar. 10, 2025 in U.S. Appl. No. 17/151,050.
Final Office Action dated Mar. 17, 2025 in U.S. Appl. No. 17/151,058.
Final Office Action dated Mar. 21, 2024 in U.S. Appl. No. 16/788,743.
Final Office Action dated Mar. 28, 2019 in U.S. Appl. No. 15/260,106.
Final Office Action dated May 13, 2024 in U.S. Appl. No. 17/157,872.
Final Office Action dated May 15, 2023 in U.S. Appl. No. 16/551,638.
Final Office Action dated May 19, 2023 in U.S. Appl. No. 17/163,177.
Final Office Action dated May 30, 2024 in U.S. Appl. No. 17/528,104.
Final Office Action dated May 31, 2023 in U.S. Appl. No. 16/934,530.
Final Office Action dated May 8, 2024 in U.S. Appl. No. 17/373,653.
Final Office Action dated Nov. 15, 2022 in U.S. Appl. No. 16/525,054.
Final Office Action dated Nov. 20, 2024 in U.S. Appl. No. 16/540,971.
Final Office Action dated Oct. 10, 2024 in U.S. Appl. No. 17/592,271.
Final Office Action dated Oct. 13, 2023 in U.S. Appl. No. 15/055,407.
Final Office Action dated Oct. 18, 2024 in U.S. Appl. No. 18/186,940.
Final Office Action dated Oct. 23, 2023 in U.S. Appl. No. 16/540,971.
Final Office Action dated Oct. 5, 2023 in U.S. Appl. No. 17/151,050.
Final Office Action dated Oct. 9, 2024 in U.S. Appl. No. 17/163,177.
Final Office Action dated Sep. 15, 2025 in U.S. Appl. No. 18/194,590.
|Final Office Action dated Sep. 19, 2024 in U.S. Appl. No. 18/324,880.
Final Office Action dated Sep. 19, 2024 in U.S. Appl. No. 18/324,890.
Final Office Action dated Sep. 6, 2024 in U.S. Appl. No. 16/789,311.
Non-Final Office Action dated Apr. 17, 2024 in U.S. Appl. No. 16/789,311.
Non-Final Office Action dated Apr. 26, 2023 in U.S. Appl. No. 16/374,626.
Non-Final Office Action dated Apr. 26, 2023 in U.S. Appl. No. 16/540,971.
Non-Final Office Action dated Aug. 14, 2025 in U.S. Appl. No. 17/147,283.
Non-Final Office Action dated Aug. 19, 2025 in U.S. Appl. No. 17/174,249.
Non-Final Office Action dated Aug. 21, 2025 in U.S. Appl. No. 18/186,936.
Non-Final Office Action dated Aug. 26, 2025 in U.S. Appl. No. 17/163,177.
Non-Final Office Action dated Dec. 28, 2023 in U.S. Appl. No. 17/157,872.
Non-Final Office Action dated Feb. 23, 2023 in U.S. Appl. No. 17/408,374.
Non-Final Office Action dated Feb. 3, 2025 in U.S. Appl. No. 17/528,104.
Non-Final Office Action dated Feb. 9, 2022 in U.S. Appl. No. 16/525,054.
Non-Final Office Action dated Feb. 9, 2024 in U.S. Appl. No. 16/846,133.
Non-Final Office Action dated Jan. 19, 2024 in U.S. Appl. No. 17/336,055.
Non-Final Office Action dated Jan. 2, 2024 in U.S. Appl. No. 17/373,653.
Non-Final Office Action dated Jan. 6, 2025 in U.S. Appl. No. 16/551,620.
Non-Final Office Action dated Jan. 6, 2025 in U.S. Appl. No. 18/190,465.

(56) References Cited

OTHER PUBLICATIONS

Non-Final Office Action dated Jul. 1, 2025 in U.S. Appl. No. 16/525,054.
Non-Final Office Action dated Jul. 15, 2025 in U.S. Appl. No. 17/957,386.
Non-Final Office Action dated Jul. 27, 2023 in U.S. Appl. No. 17/373,519.
Non-Final Office Action dated Jun. 14, 2023 In U.S. Appl. No. 17/174,249.
Non-Final Office Action dated Jun. 14, 2024 in U.S. Appl. No. 16/525,054.
Non-Final Office Action dated Jun. 18, 2025 in U.S. Appl. No. 17/707,409.
Non-Final Office Action dated Jun. 5, 2025 in U.S. Appl. No. 17/157,872.
Non-Final Office Action dated Jun. 29, 2023 in U.S. Appl. No. 17/151,058.
Non-Final Office Action dated Jun. 30, 2023 In U.S. Appl. No. 17/684,289.
Non-Final Office Action dated Mar. 13, 2023 in U.S. Appl. No. 17/151,050.
Non-Final Office Action dated Mar. 20, 2024 in U.S. Appl. No. 17/163,177.
Non-Final Office Action dated Mar. 26, 2024 in U.S. Appl. No. 18/053,603.
Non-Final Office Action dated Mar. 28, 2024 in U.S. Appl. No. 17/531,555.
Non-Final Office Action dated Mar. 28, 2025 in U.S. Appl. No. 17/545,845.
Non-Final Office Action dated May 20, 2024 in U.S. Appl. No. 18/324,880.
Non-Final Office Action dated May 20, 2024 in U.S. Appl. No. 18/324,890.
Non-Final Office Action dated May 7, 2024 in U.S. Appl. No. 17/390,640.
Non-Final Office Action dated May 7, 2025 in U.S. Appl. No. 18/643,870.
Non-Final Office Action dated Nov. 13, 2024 in U.S. Appl. No. 18/194,590.
Non-Final Office Action dated Nov. 19, 2024 in U.S. Appl. No. 17/684,289.
Non-Final Office Action dated Nov. 7, 2023 in U.S. Appl. No. 17/528,104.
Non-Final Office Action dated Nov. 8, 2024 in U.S. Appl. No. 18/053,603.
Non-Final Office Action dated Oct. 5, 2023 in U.S. Appl. No. 16/848,241.
Non-Final Office Action dated Sep. 4, 2025 in U.S. Appl. No. 17/373,653.
Non-Final Office Action dated Sep. 28, 2023 in U.S. Appl. No. 16/789,311.
Non-Final Office Action dated Sep. 28, 2023 in U.S. Appl. No. 17/184,405.
Non-Final Office Action dated Sep. 3, 2024 in U.S. Appl. No. 17/174,249.
Non-Final Office Action dated Sep. 5, 2024 in U.S. Appl. No. 17/147,283.
Non-Final Office Action dated Sep. 10, 2025 in U.S. Appl. No. 19/022,242.
Notice of Allowability dated Mar. 7, 2023 for U.S. Appl. No. 17/147,272.
Notice of Allowance dated Apr. 24, 2024 in U.S. Appl. No. 16/788,743.
Notice of Allowance dated Apr. 25, 2024 in U.S. Appl. No. 16/848,241.
Notice of Allowance dated Apr. 29, 2020 in U.S. Appl. No. 15/937,713.
Notice of Allowance dated Apr. 8, 2024 in U.S. Appl. No. 16/846,133.
Notice of Allowance dated Aug. 28, 2023 in U.S. Appl. No. 16/374,626.
Notice of Allowance dated Dec. 28, 2023 in U.S. Appl. No. 16/551,638.
Notice of Allowance dated Dec. 5, 2023 in U.S. Appl. No. 17/373,519.
Notice of Allowance dated Dec. 6, 2023 in U.S. Appl. No. 16/934,530.
Notice of Allowance dated Feb. 24, 2023 in U.S. Appl. No. 17/183,840.
Notice of Allowance dated Feb. 23, 2023 in U.S. Appl. No. 17/320,052.
Notice of Allowance dated Feb. 1, 2023 in U.S. Appl. No. 17/147,272.
Notice of Allowance dated Jun. 8, 2023 in U.S. Appl. No. 16/459,444.
Notice of Allowance dated Mar. 1, 2023 in U.S. Appl. No. 17/192,814.
Notice of Allowance dated Mar. 20, 2024 in U.S. Appl. No. 18/190,884.
Notice of Allowance dated May 28, 2025 in U.S. Appl. No. 18/324,880.
Notice of Allowance dated May 27, 2025 in U.S. Appl. No. 18/324,890.
Notice of Allowance dated Nov. 16, 2023 in U.S. Appl. No. 16/677,012.
Notice of Allowance dated Sep. 19, 2024 in U.S. Appl. No. 17/161,558.
Notice of Allowance dated Sep. 24, 2018 in U.S. Appl. No. 16/038,887.
Notice of Allowance dated Sep. 24, 2018 in U.S. Appl. No. 16/038,979.
Notice of Panel Decision from Pre-Appeal Brief Review in U.S. Appl. No. 17/151,058, dated Sep. 4, 2024.
Restriction Requirement dated Apr. 3, 2023 in U.S. Appl. No. 17/161,558.
Restriction Requirement dated Aug. 26, 2024 in U.S. Appl. No. 18/194,590.
Restriction Requirement dated Feb. 27, 2023 in U.S. Appl. No. 17/151,058.
Restriction Requirement dated Jun. 28, 2023 in U.S. Appl. No. 17/336,055.
Restriction Requirement dated Mar. 26, 2025 in U.S. Appl. No. 17/707,409.
Restriction Requirement dated May 22, 2018 in U.S. Appl. No. 15/260,106.
Restriction Requirement dated Oct. 5, 2023 in U.S. Appl. No. 17/373,653.
Restriction Requirement dated Oct. 11, 2023 in U.S. Appl. No. 17/531,555.
Restriction Requirement dated Sep. 20, 2021 in U.S. Appl. No. 16/525,054.
Supplemental Notice of Allowability dated Apr. 2, 2024 in U.S. Appl. No. 18/190,884.
International Preliminary Report on Patentability dated Feb. 23, 2021 in PCT Application No. PCT/US2019/046549.
International Preliminary Report on Patentability dated Feb. 9, 2021 in PCT Application No. PCT/US2019/043949.
International Preliminary Report on Patentability dated Jun. 24, 2021 in PCT Application No. PCT/US2019/065237.
International Preliminary Report on Patentability dated Mar. 2, 2021 in PCT Application No. PCT/US2019/048179.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Search Report and Written Opinion dated Feb. 13, 2023, in PCT Application No. PCT/US2022/075656.
International Search Report and Written Opinion dated Feb. 27, 2024 in PCT Application No. PCT/US2023/036545.
International Search Report and Written Opinion dated Jan. 12, 2024 in PCT Application No. PCT/US2023/078302.
International Search Report and Written Opinion dated Jun. 11, 2024 in PCT Application No. PCT/US2023/084669.
International Search Report and Written Opinion dated Jun. 20, 2016 in PCT Application No. PCT/US2016/014612.
International Search Report and Written Opinion dated Jun. 30, 2020 in PCT Application No. PCT/US2020/017890.
International Search Report and Written Opinion dated Nov. 18, 2024 in PCT Application No. PCT/US2024/031765.

(56) References Cited

OTHER PUBLICATIONS

International Search Report and Written Opinion dated Oct. 8, 2019 in PCT Application No. PCT/US2019/043949.
Decision to Grant dated Oct. 18, 2018 in European Patent Application No. 1461937.3.
Decision to Grant dated Oct. 14, 2021 in European Patent Application No. 17202409.3.
Decision to Grant dated Jul. 20, 2023 in European Patent Application No. 17781265.8.
Decision to Grant dated Jul. 24, 2025 in Japanese Patent Application No. 2023-165263.
Decision to Grant dated Feb. 29, 2024 in European Patent Application No. 21735076.8.
Decision of Grant dated Aug. 21, 2023 in Japanese Patent Application No. 2020-561800.
Decision of Grant dated Aug. 28, 2025 in Japanese Patent Application No. 2024000242.
Decision of Grant dated Dec. 4, 2023 in Japanese Patent Application No. 2022-096387.
Decision of Grant dated Nov. 27, 2023 In Japanese Patent Application No. 2021-505735.
Decision of Grant dated Oct. 17, 2024 in Japanese Patent Application No. 2021-507836.
Decision of Grant dated Sep. 9, 2024 in Japanese Patent Application No. 2022-077421.
Decision to Grant dated Jul. 25, 2024 in Japanese Patent Application No. 2022-071002.
Decision to Grant dated Jul. 18, 2024 in European Patent Application No. 21707112.5.
Decision to Grant dated Jul. 8, 2024 in Japanese Patent Application No. 2019-566787.
Examination Report dated Apr. 16, 2025 in European Patent Application No. 23166582.9.
Examination Report dated Apr. 17, 2025 in European Patent Application No. 24166876.3.
Examination Report dated Apr. 18, 2024 in Australian Patent Application No. 2022211826.
Examination Report dated Apr. 19, 2024 in European Patent Application No. 23166391.5.
Examination Report dated Aug. 28, 2024 in European Patent Application No. 21730393.2.
Examination Report dated Dec. 12, 2024 in European Patent Application No. 20711394.5.
Examination Report dated Dec. 19, 2024 in European Patent Application No. 18703156.2.
Examination Report dated Dec. 2, 2024 in European Patent Application No. 22777544.2.
Examination Report dated Feb. 13, 2025 in Australian Patent Application No. 2023203512.
Examination Report dated Feb. 14, 2025 in European Patent Application No. 21851636.7.
Examination Report dated Feb. 26, 2025 in European Patent Application No. 23191518.2.
Examination Report dated Feb. 6, 2025 in European Patent Application No. 21827480.1.
Examination Report dated Jan. 24, 2025 in Australian Patent Application No. 2022291534.
Examination Report dated Jan. 7, 2025 in European Patent Application No. 21704096.3.
Examination Report dated Jul. 10, 2025 in European Patent Application No. 21708803.8.
Examination Report dated Mar. 21, 2025 in European Patent Application No. 21714720.6.
Examination Report dated Mar. 31, 2025 in European Patent Application No. 24166038.0.
Examination Report dated Mar. 6, 2024 in European Patent Application No. 19836239.4.
Examination Report dated May 17, 2022 in Australian Patent Application No. 2019204928.
Examination Report dated Nov. 12, 2020 in European Patent Application No. 18716877.8.
Examination Report dated Nov. 18, 2024 in Canadian Patent Application No. 3,059,559.
Examination Report dated Nov. 24, 2023 in European Patent Application No. 20209777.0.
Examination Report dated Nov. 27, 2024 in European Patent Application No. 19836239.4.
Examination Report dated Nov. 9, 2023 in European Patent Application No. 20711394.5.
Examination Report dated Oct. 25, 2021 in European Patent Application No. 17781265.8.
Examination Report dated Oct. 25, 2024 in European Patent Application No. 23166391.5.
Examination Report dated Oct. 31, 2023 in European Patent Application No. 20753616.0.
Examination Report dated Sep. 21, 2023 in Canadian Patent Application No. 3,034,924.
Examination Report dated Sep. 3, 2024 in Australian Patent Application No. 2019262048.
Extended European Search Report dated Aug. 13, 2024 in European Patent Application No. 24166038.0.
Extended European Search Report dated Aug. 28, 2024 in European Patent Application No. 24166876.3.
Extended European Search Report dated Feb. 23, 2024 in European Patent Application No. 23191518.2.
Extended European Search Report dated Feb. 7, 2025 in European Patent Application No. 24194064.2.
Extended European Search Report dated Jan. 24, 2025 in European Patent Application No. 24194281.2.
Extended European Search Report dated Jun. 3, 2024 in European Patent Application No. 23216012.7.
Extended European Search Report dated Jun. 5, 2025 in European Patent Application No. 24221567.1.
Extended European Search Report dated Nov. 20, 2024 in European Patent Application No. 24194082.4.
Extended European Search Report dated Oct. 4, 2023 in European Patent Application No. 23166582.9.
Extended European Search Report dated Sep. 5, 2025 in European Patent Application No. 25152849.3.
Extended European Search Report dated Sep. 24, 2025 in European Patent Application No. 25173019.8.
Grounds for Opposition dated Jul. 21, 2016 and filed in European Patent 2414548B1.
Notice of Allowance dated Apr. 1, 2019 in Singapore Patent Application No. 11201405274W.
Notice of Allowance dated Apr. 4, 2023 in Australian Patent Application No. 2017331459.
Notice of Allowance dated Aug. 23, 2023 in Canadian Patent Application No. 2865575.
Notice of Allowance dated Aug. 25, 2023 in European Patent Application No. 22200785.8.
Notice of Allowance dated Dec. 6, 2023 in Korean Patent Application No. 10-2023-7012325.
Notice of Allowance dated Feb. 20, 2025 in Korean Patent Application No. 10-2022-7029623.
Notice of Allowance dated Feb. 21, 2023 in Korean Patent Application No. 10-2022-7017261.
Notice of Allowance dated Jan. 19, 2023 in Korean Patent Application No. 10-2022-7004715.
Notice of Allowance dated Jan. 20, 2024 in Chinese Patent Application No. 201911165393.0.
Notice of Allowance dated Jan. 24, 2022 in Korean Patent Application No. 10-2019-7011635.
Notice of Allowance dated Jun. 14, 2018 in Singapore Patent Application No. 11201601188T.
Notice of Allowance dated Jun. 17, 2020 in European Patent Application No. 18195513.9.
Notice of Allowance dated Jun. 18, 2021 in European Patent Application No. 17202409.3.
Notice of Allowance dated Jul. 7, 2017 in European Patent Application No. 13755319.4.

(56) References Cited

OTHER PUBLICATIONS

Notice of Allowance dated Jul. 12, 2018 in Japanese Patent Application No. 2014-558975.
Notice of Allowance dated Jul. 24, 2025 in Japanese Patent Application No. 2023-220540.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Mar. 18, 2025 in Japanese Patent Application No. 2021-517856.
Notice of Allowance dated May 23, 2024 in Chinese Patent Application No. 201980037342.1.
Notice of Allowance dated Nov. 21, 2024 in Korean Patent Application No. 10-2023-7017312.
Notice of Allowance dated Oct. 2, 2023 in European Patent Application No. 21735067.8.
Notice of Allowance dated Oct. 8, 2020 in Singapore Patent Application No. 11201901733P.
Notice of Allowance dated Oct. 25, 2023 in European Patent Application No. 20816802.1.
Notice of Allowance dated Sep. 14, 2023 in Canadian Patent Application No. 2982467.
Notice of Allowance dated Sep. 29, 2023 in European Patent Application No. 22165594.7.
Notice of Opposition dated Jul. 27, 2016 in European Patent Application No. 10762102.1.
Notice of Preliminary Rejection dated Feb. 23, 2024 for Korean Patent Application No. 10-2023-7017312.
Office Action dated Apr. 10, 2023 in Japanese Patent Application No. 2022-030956.
Office Action dated Apr. 14, 2023 in Chinese Patent Application No. 201980082680.7.
Office Action dated Apr. 17, 2025 in Chinese Patent Application No. 202180014118.8.
Office Action dated Apr. 24, 2023 in European Patent Application No. 21714995.4.
Office Action dated Apr. 24, 2023 in Japanese Patent Application No. 2020-561800.
Office Action dated Apr. 26, 2023 in European Patent Application No. 18703156.2.
Office Action dated Apr. 26, 2025 in Chinese Patent Application No. 202180060954.X.
Office Action dated Apr. 27, 2024 in Chinese Patent Application No. 202080048361.7.
|Office Action dated Apr. 27, 2024 in Chinese Patent Application No. 2021980065685.9.
Office Action dated Apr. 27, 2025 in Chinese Patent Application No. 202180065616.5.
Office Action dated Apr. 9, 2025 in Canadian Patent Application No. 3218231.
Office Action dated Aug. 10, 2024 in Chinese Patent Application No. 201980037175.0.
Office Action dated Aug. 11, 2023 in European Patent Application No. 19752792.2.
Office Action dated Aug. 4, 2025 in Japanese Patent Application No. 2024-088926.
Office Action dated Aug. 21, 2023 in Japanese Patent Application No. 2021-507836.
Office Action dated Aug. 30, 2023 in Chinese Patent Application No. 2019111653930.
Office Action dated Aug. 31, 2021 in Chinese Patent Application No. 2016800157452.
Office Action dated Aug. 31, 2023 in Chinese Patent Application No. 2020800483617.
Office Action dated Dec. 15, 2023 in Chinese Patent Application No. 201980082680.7.
Office Action dated Dec. 17, 2024 in Japanese Patent Application No. 2023-165263.
Office Action dated Dec. 26, 2024 in Chinese Patent Application No. 202180025606.9.
Office Action dated Feb. 1, 2024 in Japanese Patent Application No. 2021-507836.
Office Action dated Feb. 1, 2024 in Japanese Patent Application No. 2022-071002.
Office Action dated Feb. 13, 2024 in Japanese Patent Application No. 2022-525692.
Office Action dated Feb. 20, 2023 in European Patent Application No. 19723988.2.
Office Action dated Feb. 23, 2022 in Chinese Patent Application No. 2016800523302.
Office Action dated Feb. 23, 2023 in European Patent Application No. 20816802.1.
Office Action dated Feb. 25, 2020 in Japanese Patent Application No. 2019-014564.
Office Action dated Feb. 28, 2023 in Chinese Patent Application No. 2019111653930.
Office Action dated Feb. 28, 2024 in Chinese Patent Application No. 202080014409.2.
Office Action dated Jan. 30, 2023 in European Patent Application No. 19752792.2.
Office Action dated Jan. 31, 2024 in Chinese Patent Application No. 201980037342.1.
Office Action dated Jan. 6, 2025 in Japanese Patent Application No. 2023-220540.
Office Action dated Jul. 10, 2023 in Japanese Patent Application No. 2022-096387.
Office Action dated Jul. 10, 2024 in Chinese Patent Application No. 202080014409.2.
Office Action dated Jul. 12, 2023 in Canadian Patent Application No. 3,059,559.
Office Action dated Jul. 12, 2023 in Chinese Patent Application No. 2020800212600.
Office Action dated Jul. 12, 2024 in Chinese Patent Application No. 201980070893.8.
Office Action dated Jul. 13, 2023 in Chinese Patent Application No. 202080077712.7.
Office Action dated Jul. 24, 2024 in Chinese Patent Application No. 201980068704.3.
Office Action dated Jul. 28, 2023 in Chinese Patent Application No. 201880014793.9.
Office Action dated Jul. 28, 2025 in Japanese Patent Application No. 2024-111567.
Office Action dated Jul. 29, 2023 in Chinese Patent Application No. 201980073850.5.
Office Action dated Jul. 31, 2023 in Chinese Patent Application No. 201980037175.0.
Office Action dated Jul. 31, 2023 in Chinese Patent Application No. 201980068704.3.
Office Action dated Jul. 6, 2024 in Chinese Patent Application No. 202080048361.7.
Office Action dated Jul. 7, 2025 in Chinese Patent Application No. 202180026337.8.
Office Action dated Jun. 1, 2023 in Japanese Patent Application No. 2020-561807.
Office Action dated Jun. 10, 2024 in Japanese Patent Application No. 2021-517856.
Office Action dated Jun. 16, 2023 in Chinese Patent Application No. 2019800708938.
Office Action dated Jun. 18, 2024 In Japanese Patent Application No. 2021-523956.
Office Action dated Jun. 22, 2023 in Japanese Patent Application No. 2022-071002.
Office Action dated Jun. 24, 2025 in Chinese Patent Application No. 202180020701.X.
Office Action dated Jun. 28, 2023 in European Patent Application No. 19836239.4.

(56) References Cited

OTHER PUBLICATIONS

Office Action dated Mar. 10, 2022 in Canadian Patent Application No. 2,865,575.
Office Action dated Mar. 15, 2023 in European Patent Application No. 19787547.9.
Office Action dated Mar. 24, 2025 in Japanese Patent Application No. 2024-000242.
Office Action dated Mar. 25, 2025 in Chinese Patent Application No. 202180020686.9.
Office Action dated Mar. 25, 2025 in Chinese Patent Application No. 202180022155.3.
Office Action dated Mar. 27, 2023 in European Patent Application No. 19836036.4.
Office Action dated Mar. 29, 2023 in Chinese Patent Application No. 2020800144092.
Office Action dated Mar. 31, 2025 in Japanese Patent Application No. 2023-213088.
Office Action dated Mar. 3, 2025 in Chinese Patent Application No. 202210713090.3.
Office Action dated May 1, 2024 in Chinese Patent Application No. 201980070893.8.
Office Action dated May 16, 2023 in European Patent Application No. 21707112.5.
Office Action dated May 26, 2023 in Chinese Patent Application No. 2019800373421.
Office Action dated May 27, 2023 in Chinese Patent Application No. 2019800656859.
Office Action dated May 30, 2023 in Chinese Patent Application No. 2019800653102.
Office Action dated May 30, 2023 in Korean Patent Application No. 10-2023-7012325.
Office Action dated May 30, 2024 in Korean Patent Application No. 10-2022-7029623.
Office Action dated May 31, 2024 in Chinese Patent Application No. 201980037175.0.
Office Action dated Nov. 2, 2024 in Chinese Patent Application No. 201980073850.5.
Office Action dated Nov. 24, 2022 in Chinese Patent Application No. 2018800147939.
Office Action dated Nov. 9, 2023 in Japanese Patent Application No. 2017-549390.
Office Action dated Oct. 10, 2017 in European Patent Application No. 14761937.3.
Office Action dated Oct. 10, 2023 in European Patent Application No. 16719706.0.
Office Action dated Oct. 13, 2023 in Chinese Patent Application No. 202080014409.2.
Office Action dated Oct. 17, 2024 in Chinese Patent Application No. 202180014118.8.
Office Action dated Oct. 19, 2023 in Japanese Patent Application No. 2019-566787.
Office Action dated Oct. 19, 2024 in Chinese Patent Application No. 202080077712.7.
Office Action dated Oct. 21, 2021, in Chinese Patent Application No. 2016800073512.
Office Action dated Oct. 23, 2023 in Japanese Patent Application No. 2021-517856.
Office Action dated Oct. 26, 2023 In Japanese Patent Application No. 2022-525692.
Office Action dated Oct. 30, 2023 in Japanese Patent Application No. 2021-523956.
Office Action dated Sep. 15, 2015 in Chinese Patent Application No. 201380022187.9.
Office Action dated Sep. 21, 2022 in Israel Patent Application No. 265478.
Office Action dated Sep. 21, 2023 in Canadian Patent Application No. 3034924.
Office Action dated Sep. 21, 2023 in Israel Patent Application No. 265478.
Office Action dated Sep. 21, 2023 in Japanese Patent Application No. 2022-030956.
Summons to Attend Oral Proceedings dated Aug. 8, 2023 in European Patent Application No. 14749671.5.
Complaint filed in Becton, *Dickinson and Company and Cellular Research Inc.* v. *10X Genomics, Inc.* dated Nov. 15, 2018 in the USDC for the District of Delaware, C.A. 18-1800-RGA, 141 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Motion to Dismiss and Opening Brief in Support of the Motion to Dismiss filed in Becton, *Dickinson and Company and Cellular Research Inc.* v. *10X Genomics, Inc.* (C.A. No. 18-1800-RGA) on Jan. 18, 2019 in 72 pages.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 101 pp.
Defendant 10X Genomics, Inc.'s Reply Brief in support of its Motion to Dismiss Pursuant to Federal Rule of Civil Procedure 12(b)(6), dated Apr. 12, 2019 in USDC District of Delaware, C.A. No. 18-1800 RGA, 15 pp.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Petition for Inter Partes Review of U.S. Pat. No. 10,155,981, *Parse Biosciences, Inc.* v. *10X Genomics, Inc.* filed Apr. 20, 2023, Case No. IPR2023-00876, 93 pp.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Stipulated Protective Order Pursuant to Rule 26(c) of the Federal Rules of Civil Procedure, dated Jun. 20, 2019 in the USDC for the District of Delaware, C.A. 18-1800 (RGA), 26 pp.
IPR2023-00876, *Parse Biosciences Inc.* v. *10X Genomics Inc.*, filed Apr. 20, 2023.
IPR2023-00958, *Parse Biosciences Inc.* v. *10X Genomics Inc.*, filed May 25, 2023.
Scheduling Order pursuant to Local Rule 16.1(b), filed May 7, 2019 in the USDC for the District of Delaware, C.A. 18-1800-RGA, 10 pp.
Scheduling Order signed by Judge Andrews, dated May 8, 2019 in the USDC for the District of Delaware, C.A. 18-1800-RGA, 10 pp.
Ex Parte David H. Gelfand, Ivo Glynne Gut, Keith A. Bauer, and Florence Mauger, Appeal No. 2017-001917 (PTAB Aug. 6, 2018).
Ex Parte Olga Oranatsky, Appeal No. 2018-001623 (PTAB Jul. 29, 2019).
Ex Parte Brian Jon Peter, Appeal No. 2017-008386 (PTAB May 29, 2018).
Abcam, ab109202 DRAQ7 1ml (0.3mM) Protocol, Abcam, 2014, 1-20.
AAT Bioquest, Calcein, 2025, 1-10. Obtained online at: https://www.aatbio.com/resources/application-notes/calcein on Nov. 14, 2025.
BD FACSMelody Cell Sorter, Technical Specifications, BD Biosciences 2016, 1-4.
BD Rhapsody Single-Cell Analysis System User Guide, Becton, Dickinson and Company 2019, 1-230.
Brilliant Stain Buffer Technical Data Sheet, BD Horizon, 2014, 1-3.
Chaintoutis et at., "A Novel Real-Time RT-PCR-Based Methodology for the Preliminary Typing of SARS-CoV-2 Variants, Employ-

(56) References Cited

OTHER PUBLICATIONS ing Non-Extendable LNA Oligonucleotides and Three Signature Mutations at the Spike Protein Receptor-Binding Domain," LIFE 2021, vol. 11, No. 10, 1015, 15 pages.
Dower et al., "Detection and Characterization of high affinity plasma membrane receptors for human interleukin," The Rockefeller University Press 1985, 162:501-515.
Fixation and Permeabilization Solution, pp. 1-2, 2007, BD Biosciences.
Fluoro Trends, Celle Fixation, Permeabilization, and Intracellular Staining, pp. 1-8, May 2019, vol. 1, Issue 2.
Gehring, "Expanding Single-Cell RNA-Sequencing in Scale and Dimension," US Berkeley 2018, ProQuest ID: Gehring_berkeley_0028E_18003.
Guan et al., "Methods and Application of Plant Gene Cloning," Science and Technology Press of China 2009, 21-24.
Hobro et al., "An evaluation of fixation methods: Spatial and Compositional Cellular Changes Observed by Raman Imaging," Elsevier 2016, 31-45.
Jamur et al., "Permeabilization of Cell Membranes," Humana Press 2010, 63-66.
Ji et al., "Protein- and Sequencing-based Massively Parallel Single-cell Approaches to Gene Expression Profiling," BioProtocol, 2019, 3161, 1-24.
Johnson, "Detergents: Triton X-100, Tween-20, and More," pp. 1-12, Original Version Jan. 18, 2013 Labome, Mater Methods 3:163.
Laforte et al., "Antibody colocalization microarray for cross-reactivity-free multiplexed protein analysis," Serum/Plasma Proteomics: Methods and Protocols 2017, 239-261.
Stoeckius, "CITE-Seq Protocol", NYGS Innovation Lab 2017, 1-8.
US Forest Service Caring for the Land and Serving People, USDA Accessed from Internet on Jan. 21, 2022, pp. 1-7.
Weber et al., "Database entry EH937753," Plant Physiol., 2007, 32-42.
Final Office Action dated Apr. 8, 2026 in U.S. Appl. No. 18/187,488.
Final Office Action dated Dec. 1, 2025 in U.S. Appl. No. 18/186,940.
Final Office Action dated Feb. 20, 2026 in U.S. Appl. No. 16/525,054.
Final Office Action dated Jan. 9, 2026 in U.S. Appl. No. 18/058,216.
Final Office Action dated Mar. 6, 2026 in U.S. Appl. No. 17/174,249.
Final Office Action dated Mar. 11, 2026 in U.S. Appl. No. 17/151,058.
Final Office Action dated Oct. 9, 2025 in U.S. Appl. No. 17/157,872.
Final Office Action dated Oct. 24, 2025 in U.S. Appl. No. 17/545,845.
Non-Final Office Action dated Jan. 28, 2026 in U.S. Appl. No. 17/684,289.
Non-Final Office Action dated Jan. 28, 2026 in U.S. Appl. No. 18/186,449.
Non-Final Office Action dated Nov. 6, 2025 in U.S. Appl. No. 16/540,971.
Non-Final Office Action dated Nov. 18, 2025 in U.S. Appl. No. 16/551,620.
Non-Final Office Action dated Oct. 31, 2025 in U.S. Appl. No. 17/531,555.
Notice of Allowance dated Dec. 17, 2025 in U.S. Appl. No. 17/147,283.
Notice of Allowance dated Nov. 10, 2025 in U.S. Appl. No. 18/643,870.
Restriction Requirement dated Feb. 19, 2026 in U.S. Appl. No. 17/745,806.
Decision of Grant dated Jan. 5, 2026 In Japanese Patent Application No. 2023213088.
Decision of Rejection dated Jan. 6, 2026 in Chinese Patent Application No. 202180060954X.
Decision to Grant dated Feb. 24, 2026 in Japanese Patent Application No. 2024-088926.
Decision of Rejection dated Feb. 25, 2026 in Chinese Patent Application No. 2021800206869.
Examination Report dated Dec. 15, 2025 in European Patent Application No. 241940642.
Examination Report dated Feb. 5, 2026 in European Patent Application No. 238176168.
Examination Report dated Jan. 23, 2026 in European Patent Application No. 222037848.
Examination Report dated Jul. 21, 2025 in European Patent Application No. 218303634.
Examination Report dated Mar. 2, 2026 in European Patent Application No. 238143283.
Examination Report dated Mar. 2, 2026 in European Patent Application No. 217050194.
Examination Report dated Nov. 6, 2025 in European Patent Application No. 217303932.
Examination Report dated Nov. 7, 2025 in European Patent Application No. 217116607.
Examination Report dated Oct. 8, 2024 in European Patent Application No. 222037848.
Examination Report dated Oct. 17, 2025 in European Patent Application No. 24194082.4.
Extended European Search Report dated Apr. 1, 2026 in European Patent Application No. 25221455.6.
Extended European Search Report dated Apr. 17, 2026 in European Patent Application No. 25214751.7.
Extended European Search Report dated Apr. 21, 2026 in European Patent Application No. 25223871.2.
Extended European Search Report dated Feb. 6, 2026 in European Patent Application No. 252116439.
Extended European Search Report dated Mar. 18, 2026 in European Patent Application No. 251962528.
Notice of Acceptance dated Jan. 23, 2026 in Australian Patent Application No. 2022291534.
Notice of Acceptance dated Feb. 6, 2026 in Australian Patent Application No. 2023203512.
Notice of Reasons for Rejection dated Nov. 19, 2025 in Japanese Patent Application No. 2024-165113.
Notice of Reexamination dated Dec. 5, 2025 in Chinese Patent Application No. 2016800157452.
Office Action dated Apr. 16, 2026 in Japanese Patent Application No. 2024-111567.
Office Action dated Mar. 31, 2026 in Chinese Patent Application No. 202180082865.5.
Office Action dated Feb. 12, 2026 in Chinese Patent Application No. 2022107130903.
Office Action dated Feb. 17, 2026 in Japanese Patent Application No. 2022-030956.
Office Action dated Feb. 20, 2026 in Canadian Patent Application No. 3059559.
Office Action dated Jan. 24, 2026 in Chinese Patent Application No. 2021800656165.
Office Action dated Jan. 22, 2026 in Chinese Patent Application No. 2021800256069.
Office Action dated Mar. 25, 2026 in Chinese Patent Application No. 202180039739.1.
Office Action dated Mar. 26, 2026 in Chinese Patent Application No. 202180020701X.
Office Action dated Nov. 25, 2025 in Chinese Patent Application No. 2021800206869.
Office Action dated Nov. 26, 2025 in Chinese Patent Application No. 2021800221553.
Office Action dated Oct. 31, 2025 in Canadian Patent Application No. 3097976.
Office Action dated Sep. 24, 2025 in Chinese Patent Application No. 202210713090.3.
Office Action dated Sep. 29, 2025 in Chinese Patent Application No. 202180014118.8.
Ho et al., "Extendable blocking probe in reverse transcription for analysis of RNA variants with superior selectivity," Nucleic Acids Research, 2015, vol. 43, No. 1, 11 pages.
Nannya et al., "A Robust Algorithm for Copy Number Detection Using High-Density Oligonucleotide Single Nucleotide Polymorphism Genotyping Arrays," Cancer Res 2005, 65:(14), 6071-6079.
Stahl et al., "Visualization and analysis of gene expression in tissue sections by spatial transcriptomics," Science Mag, 2016, vol. 353, pp. 78-82 and supplemental.

(56) References Cited

OTHER PUBLICATIONS

Final Office Action dated Apr. 21, 2026 in U.S. Appl. No. 17/163,177.
Final Office Action dated Apr. 27, 2026 in U.S. Appl. No. 17/157,872.
Final Office Action dated Jan. 16, 2026 in U.S. Appl. No. 17/957,386.
Final Office Action dated May 4, 2026 in U.S. Appl. No. 19/022,242.
Non-Final Office Action dated Apr. 20, 2026 in U.S. Appl. No. 18/194,590.
Non-Final Office Action dated Apr. 21, 2026 in U.S. Appl. No. 18/058,216.
Non-Final Office Action dated Apr. 28, 2026 in U.S. Appl. No. 18/687,030.
Restriction Requirement dated Apr. 20, 2026 in U.S. Appl. No. 18/686,812.
Restriction Requirement dated May 5, 2026 in U.S. Appl. No. 18/688,919.
International Search Report and Written Opinion dated Jan. 9, 2024 in PCT Application No. PCT/US2023/078303.
Examination Report dated Apr. 9, 2025 in European Patent Application No. 227775442.
Examination Report dated Feb. 18, 2026 in European Patent Application No. 23216012.7.
Examination Report dated May 12, 2026 in European Patent Application No. 242215671.
Notice of Acceptance and Request for Reexamination dated May 13, 2026 in Chinese Patent Application No. 2022107130903.
Office Action dated Apr. 21, 2026 in Chinese Patent Application No. 2021800656165.
Office Action dated Apr. 24, 2026 in Chinese Patent Application No. 202180026337.8.
Office Action dated Mar. 31, 2026 in Brazilian Patent Application No. 1120190059008.
Office Action dated May 1, 2026 in Chinese Patent Application No. 2021800256069.

* cited by examiner

NUCLEI BARCODING AND CAPTURE IN SINGLE CELLS

RELATED APPLICATIONS

This application claims the benefit under 35 U.S.C. § 119(e) of U.S. Provisional Patent Application Ser. No. 62/714,222, filed Aug. 3, 2018, the content of this related application is incorporated herein by reference in its entirety for all purposes.

BACKGROUND

Field

The present disclosure relates generally to the field of molecular barcoding of targets and more particularly to nuclei barcoding.

Description of the Related Art

Methods and techniques such as barcoding using beads coupled to nucleic acid barcodes are useful for single cell analysis, such as deciphering gene expression profiles to determine the states of single cells using, for example, reverse transcription, polymerase chain reaction (PCR) amplification, and next generation sequencing (NGS). However, preparing single cell suspensions for single cell analysis can be challenging.

SUMMARY

Disclosed herein include embodiments of a method for determining the numbers of targets in a plurality of cells. In some embodiments, the method comprises: isolating a plurality of nuclei of a plurality of cells using a nuclei-isolation composition, wherein the nuclei-isolation composition comprises a nuclei-binding reagent, and wherein the nuclei-binding reagent is capable of specifically binding to one or more components of a nucleus; barcoding a plurality of targets in the plurality of nuclei using a plurality of barcodes to generate a plurality of barcoded targets, wherein each of the plurality of barcodes comprises a molecular label sequence and a target-binding region, and wherein the molecular label sequences of at least two barcodes of the plurality of barcodes comprise different sequences; obtaining sequencing data of the plurality of barcoded target targets; and estimating the number of each of the plurality of targets in the plurality of cells using the molecular label sequences of the plurality of barcodes in the sequencing data.

In some embodiments, isolating the plurality of nuclei comprises: contacting the plurality of nuclei of the plurality of cells with the nuclei-isolation composition to generate nuclei bound to the nuclei-binding reagent. Isolating the plurality of nuclei can comprise: isolating the nuclei bound to the nuclei-binding reagent using a reagent capable of specifically binding to the nuclei-binding reagent.

In some embodiments, the nuclei-binding reagent is associated with a first epitope, and the reagent capable of specifically binding to the nuclei-binding reagent comprises a first epitope-binding reagent. The first epitope can comprise biotin, hapten, or a combination thereof. The hapten can comprise digoxigenin, 2,4-dinitrophenol, fluorescein, or a combination thereof. The reagent capable of specifically binding to the nuclei-binding reagent can comprise an anti-hapten antibody. The reagent capable of specifically binding to the nuclei-binding reagent can comprise avidin, streptavidin, neutravidin, or a combination thereof. In some embodiments, the nuclei binding reagent comprises a functional group selected from the group consisting of biotin, streptavidin, heparin, an aptamer, a click-chemistry moiety, digoxigenin, primary amine(s), carboxyl(s), hydroxyl(s), aldehyde(s), ketone(s), or a combination thereof. In some embodiments, the reagent capable of specifically binding to the nuclei-binding reagent comprises a functional group selected from the group consisting of biotin, streptavidin, heparin, an aptamer, a click-chemistry moiety, digoxigenin, primary amine(s), carboxyl(s), hydroxyl(s), aldehyde(s), ketone(s), or a combination thereof.

In some embodiments, the nuclei-binding reagent comprises a primary antibody capable of specifically binding to the one or more components of the nucleus, and the reagent capable of specifically binding to the nuclei-binding reagent comprises a secondary antibody capable of specifically binding to the primary antibody.

In some embodiments, the nuclei-binding reagent comprises a carbohydrate-binding reagent. The carbohydrate-binding reagent can comprise a carbohydrate-binding protein. The carbohydrate-binding protein can comprise a lectin. The lectin can comprise a mannose binding lectin, a galactose binding lectin, an N-acetylgalactosamine binding lectin, an N-acetylglucosamine binding lectin, a N-acetylneuraminic acid binding lectin, a fucose binding lectin, or a combination thereof. The lectin can comprise Concanavalin A (ConA), Lentil lectin (LCH), Snowdrop lectin (GNA), *Ricinus communis* Agglutinin (RCA), Peanut agglutinin (PNA), Jacalin (AIL), Hairy vetch lectin (VVL), Wheat Germ Agglutinin (WGA), Elderberry lectin (SNA), *Maackia amurensis* leukoagglutinin (MAL), *Maackia amurensis* hemoagglutinin (MAH), *Ulex europaeus* agglutinin (UEA), *Aleuria aurantia* lectin (AAL), or a combination thereof. The lectin can be, or comprise, an agglutinin. The agglutinin can be, or comprise, Wheat Germ Agglutinin (WGA). The carbohydrate-binding protein can be from, or derived from, an animal, a bacterium, a virus, a fungus, or a combination thereof. The carbohydrate-binding protein can be from, or derived from, a plant. The plant can be, *Canavalia ensiformis, Lens culinaris, Galanthus nivalis, Ricinus communis, Arachis hypogaea, Artocarpus integrifolia, Vicia villosa, Triticum vulgaris, Sambucus nigra, Maackia amurensis, Ulex europaeus, Aleuria aurantia*, or a combination thereof.

In some embodiments, the one or more components of the nucleus comprise a sugar, an oligosaccharide, a polysaccharides, a derivative thereof, or a combination thereof. The one or more components of the nucleus can comprise s a monosaccharide, a disaccharide, a polyol, a malto-oligosaccharide, a non-malto-oligosaccharide, a starch, a non-starch polysaccharide, a derivative thereof, or a combination thereof. The one or more components of the nucleus can comprise glucose, galactose, fructose, xylose, sucrose, lactose, maltose, trehalose, sorbitol, mannitol, maltodextrin, raffinose, stachyose, fructo-oligosaccharid, amylose, amylopectin, modified starch, glycogen, cellulose, hemicellulose, pectin, hydrocolloid, a derivative thereof, or a combination thereof. The one or more components of the nucleus can comprise a α-D-mannosyl residue, α-D-glucosyl residue, a branched α-mannosidic structure of high α-mannose type, a branched α-mannosidic structure of hybrid type and biantennary complex type N-Glycan, a fucosylated core region of bi- and triantennary complex type N-Glycan, a α 1-3 and a 1-6 linked high mannose structure, Galβ1-4GalNAcβ1-R, Galβ1-3GalNAcα1-Ser/Thr, (Sia)Galβ1-3GalNAcα1-Ser/Thr, GalNAcα-Ser/Thr, GlcNAcβ1-4GlcNAcβ1-4GlcNAc, Neu5Ac (sialic acid), Neu5Acα2-6Gal(NAc)-R, Neu5Ac/Gcα2,3Galβ1,4Glc(NAc), Neu5Ac/Gcα2,3Galβ1,3(Neu5Acα2,6)GalNac, Fucα1-2Gal-R, Fucα1-2Galβ1-4(Fucα1-3/4)Galβ1-4GlcNAc, R2-GlcNAcβ1-4(Fucα1-6)GlcNAc-R1, a derivative thereof, or a combination thereof. The one or more components of the nucleus can comprise a glycoprotein, a glycolipid, or a combination thereof.

In some embodiments, the one or more components of the nucleus comprise Lamin, Emerin, Nesprin, Nurim, UNC-83, Klar, ZYG-12, Kmslp, UNC-84, Klaroid, SUN-1, Sadlp, LBR, MAN1, LAP1, LAP2, LINK, a nuclear pore complex, a portion thereof, or a combination thereof.

In some embodiments, the nuclei-binding reagent is associated with a nucleus-isolation particle. The reagent capable of specifically binding to the nuclei-binding reagent can be associated with the nucleus-isolation particle. The reagent capable of specifically binding to the nuclei-binding reagent can be immobilized, or partially immobilized, on the nucleus-isolation particle. For example, the reagent capable of specifically binding to the nuclei-binding reagent can be reversibly, non-reversibly, covalently, non-covalently, or a combination thereof, associated with the nucleus-isolation particle. As another example, the reagent capable of specifically binding to the nuclei-binding reagent can embedded, partially embedded, non-embedded, enclosed, partially enclosed, non-enclosed, or a combination thereof, in the nucleus-isolation particle. In some embodiments, the reagent capable of specifically binding to the nuclei binding reagent is associated with the nucleus-isolation particle through a cleavable linker. The cleavable linker can, for example, comprises a chemically cleavable linkage, a photocleavable linkage, an acid labile linker, a heat sensitive linkage, an enzymatically cleavable linkage, or a combination thereof.

In some embodiments, the nucleus-isolation particle comprises a nucleus-isolation bead. The nucleus-isolation particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The nucleus-isolation particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. The nucleus-isolation particle can be disruptable. The nucleus-isolation particle can comprise a nucleus-isolation disruptable hydrogel particle. In some embodiments, isolating the nuclei bound to the nuclei-binding reagent comprises contacting the nuclei bound to the nuclei-binding reagent with a plurality of nucleus isolation particles. In some embodiments, the method comprises, prior to contacting the nuclei bound to the nuclei-binding reagent with a plurality of nucleus isolation particles, contacting the nuclei bound to the nuclei-binding reagent with a plurality of null particles. In some embodiments, the ratio of null particles to nucleus isolation particles is at least 10:1. The null particle, in some embodiments, does not comprise a magnetic property. In some embodiments, the null particle does not comprise a reagent capable of specifically binding to the nuclei binding reagent. In some embodiments, the null particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or a combination thereof. In some embodiments, the plurality of null particles reduce clumping of the nucleus isolation particles, or prevent clumping of the nucleus isolation particles, or both. In some embodiments, contacting the nuclei bound to the nuclei-binding reagent with a plurality of nucleus isolation particles generates a plurality of nuclei bound to nucleus isolation particles through the reagent capable of specifically binding to the nuclei binding reagent. In some embodiments, the percentage of nuclei bound to a single nucleus isolation particle after contacting the nuclei bound to the nuclei-binding reagent with a plurality of nucleus isolation particles is at least 90%, at least 95%, or at least 99%. In some embodiments, the percentage of nucleus isolation particles bound to a single nuclei or no nuclei after contacting the nuclei bound to the nuclei-binding reagent with a plurality of nucleus isolation particles is at least 90%, at least 95%, or at least 99%.

In some embodiments, isolating the nuclei bound to the nuclei-binding reagent can comprise: isolating the nucleus-isolation particle by magnetic removal, centrifugation, or any combination thereof. In some embodiments, the method comprises, prior to isolating the plurality of nucleus-isolation particles, contacting the plurality of nuclei bound to nucleus isolation particles with free first epitope, wherein free first epitope comprises all or a portion of the first epitope. In some embodiments, the plurality of barcodes is associated with the nucleus-isolation particle. At least one barcode of the plurality of barcodes can be immobilized on the nucleus-isolation particle. At least one barcode of the plurality of barcodes can be partially immobilized on the nucleus-isolation particle. At least one barcode of the plurality of barcodes can be enclosed in the nucleus-isolation particle. At least one barcode of the plurality of barcodes can be partially enclosed in the nucleus-isolation particle. At least one barcode of the plurality of barcodes can be not enclosed in the nucleus-isolation particle. At least one barcode of the plurality of barcodes can be embedded in the nucleus-isolation particle. At least one barcode of the plurality of barcodes can be partially embedded in the nucleus-isolation particle. At least one barcode of the plurality of barcodes can be not embedded in the nucleus-isolation particle.

In some embodiments, the nuclei-binding reagent comprises a nuclear envelope surface component-binding reagent, and the nuclei-binding reagent can be capable of specifically binding to one or more nuclear envelope surface components.

In some embodiments, the method comprises: prior to barcoding the plurality of targets in the plurality of nuclei using the plurality of barcodes to generate the plurality of barcoded targets, lysing the plurality of nuclei. In some embodiments, the method comprises: prior to isolating the plurality of nuclei of the plurality of cells using the nuclei-isolation composition, lysing the plurality of cells without lysing nuclei of the plurality of cells. In some embodiments, the method comprises prior to lysing the plurality of nuclei, partitioning the plurality of nuclei. In some embodiments, partitioning the plurality of nuclei comprises partitioning the plurality of nuclei to a plurality of partitions, wherein a partition of the plurality of partitions comprises a single nuclei from the plurality of nuclei. In some embodiments, the plurality of partitions comprises microwells of a microwell array. In some embodiments, the plurality of partitions comprise a plurality of droplets. In some embodiments, two or more partitions of the plurality of partitions comprise a single nuclei. In some embodiments, a partition of the plurality of partitions comprises a single nuclei and a single nuclei isolation particle. In some embodiments, a partition of the plurality of partitions comprises a single nuclei and a single barcoding particle. In some embodiments, a partition of the plurality of partitions comprises a single nuclei, a single nuclei isolation particle, and a single barcoding particle In some embodiments, the method comprises: prior to isolating the plurality of nuclei of the plurality of cells using the nuclei-isolation composition, permeating (e.g., lying the plasma membrane of) the plurality of cells; and depleting one or more organelles of the plurality of cells using an organelles-capture composition comprising an organelles-binding reagent, wherein the organelles-binding reagent is capable of specifically binding to one or more components of the one or more organelles of the plurality of cells. Depleting the one or more organelles can comprise: contacting the one or more organelles of the plurality of cells with the organelles-capture composition to generate one or more organelles bound to the organelle component-binding reagent. Depleting the one or more organelles can comprise: depleting the one or more organelles bound to the organelles-binding reagent using a reagent capable of specifically binding to the organelles-binding reagent. The organelles-binding reagent can be associated with a second epitope, and the reagent capable of specifically binding to the organelles-binding reagent can comprise a second epitope-binding reagent.

In some embodiments, the second epitope can comprise biotin, hapten, or a combination thereof. The hapten can comprise digoxigenin, 2,4-dinitrophenol, fluorescein, or a combination thereof. The reagent capable of specifically binding to the organelles-binding reagent can comprise an anti-hapten antibody. The reagent capable of specifically binding to the organelles-binding reagent can comprise avidin, streptavidin, neutravidin, or a combination thereof. The organelles-binding reagent can comprise a primary antibody capable of specifically binding to the one or more components of the one or more organelles of the plurality of cells, and the reagent capable of specifically binding to the organelles-binding reagent can comprise a secondary antibody capable of specifically binding to the primary antibody.

In some embodiments, the organelles-binding reagent is associated with an organelles-capture particle. The organelles-binding reagent can be immobilized, or partially immobilized, on the organelles-capture particle. For example, the organelles-binding reagent can be reversibly, non-reversibly, covalently, non-covalently, or a combination thereof, associated with the organelles-capture particle e. As another example, the organelles-binding reagent can embedded, partially embedded, non-embedded, enclosed, partially enclosed, non-enclosed, or a combination thereof, in the organelles-capture particle.

In some embodiments, the organelles-capture particle comprises an organelles-capture bead. The organelles-capture particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The organelles-capture particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof.

In some embodiments, depleting the organelles of the plurality of cells using the organelles-capture composition can comprise: depleting the one or more organelles-capture particles by magnetic removal, centrifugation, or any combination thereof. The organelles can comprise mitochondria of the plurality of cells. The one or more components of the one or more organelles of the plurality of cells can comprise: ABCD3, ESR2, NOS3, ALB, HIF1A, NR3C1, ATP5A1, HK1, PGR, CASQ1, HSPA1A, PHB, CLTC, HSPD1, PLN, COX4I1, IFM1, SOD1, CPS1, LGALS3, TP53, Cytochrome C Oxidase, MAPT, TP5B, ERN1, MT-CO1, VDAC1, or a combination thereof.

In some embodiments, the organelles-binding reagent can comprise an organelle surface component-binding reagent, the one or more components of the one or more organelles can comprise one or more organelle surface components, and the organelles-binding reagent can be capable of specifically binding to the one or more organelle surface components. The nuclei-binding reagent can comprise a nuclei indexing oligonucleotide, and wherein the nuclei indexing oligonucleotide comprises a nuclei indexing sequence.

In some embodiments, the method comprises: barcoding the nuclei indexing oligonucleotides using the plurality of barcodes to generate a plurality of barcoded nuclei indexing oligonucleotides; and obtaining sequencing data of the plurality of barcoded nuclei indexing oligonucleotides. Barcoding the nuclei indexing oligonucleotides can comprise: stochastically barcoding using the plurality of barcodes to generate the plurality of barcoded nuclei indexing oligonucleotides. Barcoding the nuclei indexing oligonucleotides using the plurality of barcodes can comprise: contacting the plurality of barcodes with the nuclei indexing oligonucleotides to generate barcodes hybridized to the nuclei indexing oligonucleotides; and extending the barcodes hybridized to the nuclei indexing oligonucleotides to generate the plurality of barcoded nuclei indexing oligonucleotides. Extending the barcodes can comprise: extending the barcodes using a DNA polymerase to generate the plurality of barcoded nuclei indexing oligonucleotides. Extending the barcodes can comprise: extending the barcodes using a reverse transcriptase to generate the plurality of barcoded nuclei indexing oligonucleotides.

In some embodiments, the method can comprise: amplifying the plurality of barcoded nuclei indexing oligonucleotides to produce a plurality of barcoded nucleus indexing amplicons. Amplifying the plurality of barcoded nuclei indexing oligonucleotides can comprise: amplifying, using polymerase chain reaction (PCR), at least a portion of the molecular label sequence and at least a portion of the nuclei indexing oligonucleotide. Obtaining the sequencing data of the plurality of barcoded nuclei indexing oligonucleotides can comprise: obtaining sequencing data of the plurality of barcoded nucleus indexing amplicons. Obtaining the sequencing data of the plurality of barcoded nuclei indexing oligonucleotides can comprise: sequencing the at least a portion of the molecular label sequence and the at least a portion of the nuclei indexing oligonucleotide.

In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can comprise a barcoding bead. The barcoding particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The barcoding particle can comprise a disruptable hydrogel particle.

In some embodiments, barcoding the plurality of targets using the plurality of barcodes to generate the plurality of barcoded targets comprises: contacting copies of the targets with target-binding regions of the barcodes; and reverse transcribing the plurality targets using the plurality of barcodes to generate the plurality of barcoded targets. The method can comprise: prior to obtaining the sequencing data of the plurality of barcoded targets, amplifying the plurality of barcoded targets to generate a plurality of amplified barcoded targets. Amplifying the barcoded targets to generate the plurality of amplified barcoded targets can comprise: amplifying, using polymerase chain reaction (PCR), the barcoded targets to generate the plurality of amplified barcoded targets. The method can comprise: amplifying the plurality of amplified barcoded targets to generate a plurality of barcoded targets amplicons. Amplifying the plurality of amplified barcoded targets can comprise: amplifying the molecular label sequence and the sequence of a target of the plurality of targets, or a portion thereof, to generate the plurality of barcoded targets amplicons. Amplifying the plurality of amplified barcoded targets can comprise: amplifying, using polymerase chain reaction (PCR), the plurality of amplified barcoded targets to generate the plurality of barcoded targets amplicons. Barcoding the plurality of targets of the cell using the plurality of barcodes to generate the plurality of barcoded targets can comprise: stochastically barcoding the plurality of targets of the cell using a plurality of stochastic barcodes to generate a plurality of stochastically barcoded targets.

In some embodiments, each of the plurality of barcodes comprises a cell label sequence, a binding site for a universal primer, or any combination thereof, and the cell label sequences of at least two barcodes of the plurality of barcodes comprise an identical sequence. The target-binding region can comprise a poly(dT) region. At least 100 molecular label sequences of the plurality of barcodes can comprise different sequences. At least 1000 molecular label sequences of the plurality of barcodes can comprise different sequences. At least 10000 molecular label sequences of the plurality of barcodes can comprise different sequences. The molecular label sequences of the plurality of barcodes can comprise random sequences. The target-binding region can comprise a gene-specific sequence, an oligo(dT) sequence, a random multimer, or any combination thereof. the plurality of cells comprise a tissue sample. The plurality of cells can, for example, comprise an epithelial tissue sample, frozen cells, fixed cells, formalin-fixed paraffin-embedded cells, tumor cells, fixed tumor cells, frozen tumor cells, formalin-fixed paraffin-embedded tumor cells, or a combination thereof. In some embodiments, the plurality of cells comprise one or more extranuclear cellular components. Non-limiting examples of extranuclear cellular components comprise mitochondria, peroxisomes, cytosol, vesicles, lysosomes, plasma membranes, chloroplasts, inner mitochondrial matrices, inner mitochondrial membranes, intermembrane spaces, outer mitochondrial membranes, secretory vesicles, smooth endoplasmic reticuli, rough endoplasmic reticuli, golgi bodies, phagosomes, endosomes, exosomes, plasma membranes, microtubules, microfilaments, intermediate filaments, filopodia, ruffles, lamellipodia, sarcomeres, focal contacts, podosomes, ribosomes, microsomes, lipid rafts, cell walls, or any combination thereof. In some embodiments, the one or more extranuclear cellular components comprise one or more undesirable nucleic acid species. In some embodiments, the abundance of the at least one of the one or more extranuclear cellular components is reduced by isolating the plurality of nuclei, reduced by depleting the one or more organelles, or both. In some embodiments, the plurality of cells comprises a plurality of targets and one or more undesirable nucleic acid species. In some embodiments, undesirable nucleic acid species are derived from non-nuclear organelles. In some embodiments, the undesirable nucleic acid species comprises ribosomal RNA, mitochondrial RNA, mitochondrial DNA. In some embodiments, the abundance of the at least one of the one or more undesirable nucleic acid species is reduced by isolating the plurality of nuclei, by depleting the one or more organelles, or both. In some embodiments, the one or more undesirable nucleic acid species amounts to about 50%, about 60%, about 70%, about 80%, or more of the nucleic acid content of the plurality of cells. In some embodiments, the undesirable nucleic acid species represents less than 40%, less than 20%, less than 10%, less than 5% of the plurality of barcoded targets amplicons. In some embodiments, obtaining sequencing data of the plurality of barcoded targets comprises generating a plurality of sequencing reads. the sequencing reads for the undesirable nucleic acid species can be, for example, less than 40%, less than 20%, less than 10%, less than 5% of the total sequencing reads.

Disclosed herein includes embodiments of a barcoding composition. In some embodiments, the barcoding composition comprises: a nuclei-isolation composition comprising a nuclei-binding reagent, wherein the nuclei-binding reagent is capable of specifically binding to one or more components of a nucleus; and a plurality of barcodes, wherein each of the plurality of barcodes comprises a molecular label sequence and a target-binding region, and wherein the molecular label sequences of at least two barcodes of the plurality of barcodes comprise different sequences.

In some embodiments, the composition comprises: a reagent capable of specifically binding to the nuclei-binding reagent. The nuclei-binding reagent can be associated with a first epitope, and the reagent capable of specifically binding to the nuclei-binding reagent can comprise a first epitope-binding reagent. The first epitope can comprise biotin, hapten, or a combination thereof. The hapten can comprise digoxigenin, 2,4-dinitrophenol, fluorescein, or a combination thereof. The reagent capable of specifically binding to the nuclei-binding reagent can comprise an anti-hapten antibody. The reagent capable of specifically binding to the nuclei-binding reagent can comprise avidin, streptavidin, neutravidin, or a combination thereof.

In some embodiments, the nuclei-binding reagent comprises a primary antibody capable of specifically binding to the one or more components of the nucleus, and the reagent capable of specifically binding to the nuclei-binding reagent comprises a secondary antibody capable of specifically binding to the primary antibody.

In some embodiments, the nuclei-binding reagent comprises a carbohydrate-binding reagent. The carbohydrate-binding reagent can comprise a carbohydrate-binding protein. The carbohydrate-binding protein can comprise a lectin. The lectin can comprise a mannose binding lectin, a galactose binding lectin, an N-acetylgalactosamine binding lectin, an N-acetylglucosamine binding lectin, a N-acetylneuraminic acid binding lectin, a fucose binding lectin, or a combination thereof. The lectin can comprise Concanavalin A (ConA), Lentil lectin (LCH), Snowdrop lectin (GNA), *Ricinus communis* Agglutinin (RCA), Peanut agglutinin (PNA), Jacalin (AIL), Hairy vetch lectin (VVL), Wheat Germ Agglutinin (WGA), Elderberry lectin (SNA), *Maackia amurensis* leukoagglutinin (MAL), *Maackia amurensis* hemoagglutinin (MAH), *Ulex europaeus* agglutinin (UEA), *Aleuria aurantia* lectin (AAL), or a combination thereof. The lectin can be, or comprise, an agglutinin. The agglutinin can be, or comprise, Wheat Germ Agglutinin (WGA). The carbohydrate-binding protein can be from, or derived from, an animal, a bacterium, a virus, or a fungus. The carbohydrate-binding protein can be from, or derived from, a plant. The plant can be, *Canavalia ensiformis, Lens culinaris, Galanthus nivalis, Ricinus communis, Arachis hypogaea, Artocarpus integrifolia, Vicia villosa, Triticum vulgaris, Sambucus nigra, Maackia amurensis, Ulex europaeus, Aleuria aurantia*, or a combination thereof.

In some embodiments, the one or more components of the nucleus comprise a sugar, an oligosaccharide, a polysaccharides, a derivative thereof, or a combination thereof. The one or more components of the nucleus can comprise s a monosaccharide, a disaccharide, a polyol, a malto-oligosaccharide, a non-malto-oligosaccharide, a starch, a non-starch polysaccharide, a derivative thereof, or a combination thereof. The one or more components of the nucleus can comprise glucose, galactose, fructose, xylose, sucrose, lactose, maltose, trehalose, sorbitol, mannitol, maltodextrin, raffinose, stachyose, fructo-oligosaccharid, amylose, amylopectin, modified starch, glycogen, cellulose, hemicellulose, pectin, hydrocolloid, a derivative thereof, or a combination thereof. The one or more components of the nucleus can comprise a α-D-mannosyl residue, α-D-glucosyl residue, a branched α-mannosidic structure of high α-mannose type, a branched α-mannosidic structure of hybrid type and biantennary complex type N-Glycan, a fucosylated core region of bi- and triantennary complex type N-Glycan, a α 1-3 and a 1-6 linked high mannose structure, Galβ1-4GalNAcβ1-R, Galβ1-3GalNAcα1-Ser/Thr, (Sia)Galβ1-3GalNAcα1-Ser/Thr, GalNAcα-Ser/Thr, GlcNAcβ1-4GlcNAcβ1-4GlcNAc, Neu5Ac (sialic acid), Neu5Acα2-6Gal(NAc)-R, Neu5Ac/Gcα2,3Galβ1,4Glc(NAc), Neu5Ac/Gcα2,3Galβ1,3(Neu5Acα2,6)GalNac, Fucα1-2Gal-R, Fucα1-2Galβ1-4(Fucα1-3/4)Galβ1-4GlcNAc, R2-GlcNAcβ1-4(Fucα1-6)GlcNAc-R1, a derivative thereof, or a combination thereof. The one or more components of the nucleus can comprise a glycoprotein, a glycolipid, or a combination thereof.

In some embodiments, the nuclei-binding reagent is associated with a nucleus-isolation particle. The reagent capable of specifically binding to the nuclei-binding reagent can be associated with the nucleus-isolation particle. The reagent capable of specifically binding to the nuclei-binding reagent can be immobilized, or partially immobilized, on the nucleus-isolation particle. The nucleus-isolation particle can comprise a nucleus-isolation bead. The nucleus-isolation particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The nucleus-isolation particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The nucleus-isolation particle can be disruptable. The nucleus-isolation particle can comprise a nucleus-isolation disruptable hydrogel particle.

In some embodiments, the plurality of barcodes is associated with the nucleus-isolation particle. At least one barcode of the plurality of barcodes can be immobilized on the nucleus-isolation particle. At least one barcode of the plurality of barcodes can be partially immobilized on the nucleus-isolation particle. At least one barcode of the plurality of barcodes can be enclosed in the nucleus-isolation particle. At least one barcode of the plurality of barcodes can be partially enclosed in the nucleus-isolation particle.

In some embodiments, the one or more components of the nucleus can comprise Lamin, Emerin, Nesprin, Nurim, UNC-83, Klar, ZYG-12, Kmslp, UNC-84, Klaroid, SUN-1, Sadlp, LBR, MAN1, LAP1, LAP2, LINK, a nuclear pore complex, a portion thereof, or a combination thereof. In some embodiments, the nuclei-binding reagent comprises a nuclear envelope surface component-binding reagent, and the nuclei-binding reagent can be capable of specifically binding to one or more nuclear envelope surface components.

In some embodiments, the composition comprises an organelles-capture composition comprising an organelles-binding reagent, wherein the organelles-binding reagent is capable of specifically binding to one or more components of one or more organelles. The composition can comprise a reagent capable of specifically binding to the organelles-binding reagent. The organelles-binding reagent can be associated with a second epitope, and the reagent capable of specifically binding to the organelles-binding reagent can comprise a second epitope-binding reagent. The second epitope can comprise biotin, hapten, or a combination thereof. The hapten can comprise digoxigenin, 2,4-dinitrophenol, fluorescein, or a combination thereof. The reagent capable of specifically binding to the organelles-binding reagent can comprise an anti-hapten antibody. The reagent capable of specifically binding to the organelles-binding reagent can comprise avidin, streptavidin, neutravidin, or a combination thereof. The organelles-binding reagent can comprise a primary antibody capable of specifically binding to the one or more components of the one or more organelles of the plurality of cells, and the reagent capable of specifically binding to the organelles-binding reagent can comprise a secondary antibody capable of specifically binding to the primary antibody.

In some embodiments, the organelles-binding reagent is associated with an organelles-capture particle. The organelles-binding reagent can be immobilized, or partially immobilized, on the organelles-capture particle. The organelles-capture particle can comprise an organelles-capture bead. The organelles-capture particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The organelles-capture particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof.

In some embodiments, the organelles comprise mitochondria of the plurality of cells. The one or more components of the one or more organelles of the plurality of cells can comprise ABCD3, ESR2, NOS3, ALB, HIF1A, NR3C1, ATP5A1, HK1, PGR, CASQ1, HSPA1A, PHB, CLTC, HSPD1, PLN, COX4I1, IFM1, SOD1, CPS1, LGALS3, TP53, Cytochrome C Oxidase, MAPT, TP5B, ERN1, MT-CO1, VDAC1, or a combination thereof.

In some embodiments, the organelles-binding reagent comprises an organelle surface component-binding reagent, the one or more components of the one or more organelles can comprise one or more organelle surface components, and the organelles-binding reagent can be capable of specifically binding to the one or more organelle surface components.

In some embodiments, the nuclei-binding reagent can comprise a nuclei indexing oligonucleotide, and wherein the nuclei indexing oligonucleotide comprises a nuclei indexing sequence. The plurality of barcodes can be associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can comprise a barcoding bead. The barcoding particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The barcoding particle can comprise a disruptable hydrogel particle.

In some embodiments, each of the plurality of barcodes comprises a cell label sequence, a binding site for a universal primer, or any combination thereof, and the cell label sequences of at least two barcodes of the plurality of barcodes comprise an identical sequence.

The target-binding region can comprise a poly(dT) region. At least 100 molecular label sequences of the plurality of barcodes can comprise different sequences. At least 1000 molecular label sequences of the plurality of barcodes can comprise different sequences. At least 10000 molecular label sequences of the plurality of barcodes can comprise different sequences. The molecular label sequences of the plurality of barcodes can comprise random sequences. The target-binding region can comprise a gene-specific sequence, an oligo(dT) sequence, a random multimer, or any combination thereof.

DETAILED DESCRIPTION

Figure 1:
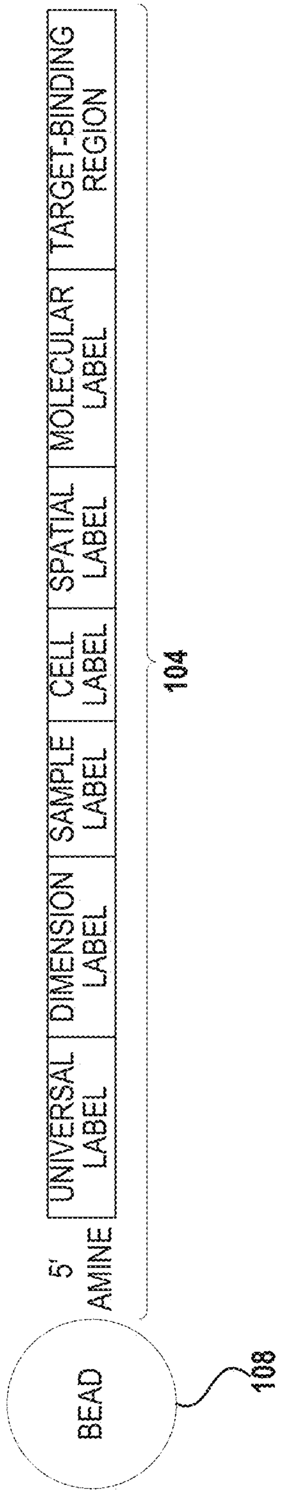
FIG. 1 illustrates a non-limiting exemplary barcode (e.g., a stochastic barcode).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Determining numbers of nucleic acids or targets, for example messenger ribonucleic acid (mRNA) molecules, is clinically important for identifying, for example, the genes that are expressed in a cell at different stages of development or under different environmental conditions. However, it can be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements.

Barcodes (e.g., stochastic barcodes) with unique molecular labels (MLs, also referred to as molecular indexes (MIs)) can be used to count the numbers of molecules. Barcodes with molecular labels that are unique for each cell label can be used to count the numbers of molecules in each cell. Non-limiting exemplary assays for barcoding include the Precise™ assay (Cellular Research, Inc. (Palo Alto, CA)), the Resolve™ assay (Cellular Research, Inc. (Palo Alto, CA)), or the Rhapsody™ assay (Becton, Dickinson and Company (Franklin Lakes, NJ)). However, these methods and techniques can introduce errors, if uncorrected, may result in overestimated cell counts.

The Rhapsody™ assay can utilize a non-depleting pool of barcodes (e.g., stochastic barcodes) with large number, for example 6561 to 65536, unique molecular labels on poly(T) oligonucleotides to hybridize to all poly(A)-mRNAs in a sample during the reverse transcription (RT) step. In addition to molecular labels, cell labels of the barcodes can be used to identify each single cell in each well of a microwell plate. A barcode can comprise a universal PCR priming site. During RT, target gene molecules react randomly with barcodes. Each target molecule can hybridize to a barcode (e.g., a stochastic barcode) resulting to generate barcoded complementary ribonucleotide acid (cDNA) molecules (e.g., stochastically barcoded cDNA molecules. After labeling, barcoded cDNA molecules from microwells of a microwell plate can be pooled into a single tube for PCR amplification and sequencing. Raw sequencing data can be analyzed to produce the numbers of barcodes with unique molecular labels.

Disclosed herein include embodiments of a method for determining the numbers of targets in a plurality of cells. In some embodiments, the method comprises: isolating a plurality of nuclei of a plurality of cells using a nuclei-isolation composition, wherein the nuclei-isolation composition comprises a nuclei-binding reagent, and wherein the nuclei-binding reagent is capable of specifically binding to one or more components of a nucleus; barcoding a plurality of targets in the plurality of nuclei using a plurality of barcodes to generate a plurality of barcoded targets, wherein each of the plurality of barcodes comprises a molecular label sequence and a target-binding region, and wherein the molecular label sequences of at least two barcodes of the plurality of barcodes comprise different sequences; obtaining sequencing data of the plurality of barcoded target targets; and estimating the number of each of the plurality of targets in the plurality of cells using the molecular label sequences of the plurality of barcodes in the sequencing data.

Disclosed herein includes embodiments of a barcoding composition. In some embodiments, the barcoding composition comprises: a nuclei-isolation composition comprising a nuclei-binding reagent, wherein the nuclei-binding reagent is capable of specifically binding to one or more components of a nucleus; and a plurality of barcodes, wherein each of the plurality of barcodes comprises a molecular label sequence and a target-binding region, and wherein the molecular label sequences of at least two barcodes of the plurality of barcodes comprise different sequences.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can be a physical association, direct or indirect. In some embodiments, two or more associated species are "tethered", "attached", or "immobilized" to one another or to a common solid or semisolid surface. An association may refer to covalent or non-covalent means for attaching labels to solid or semi-solid supports such as synthetic particles or beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence.

As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$—), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be a particle, such as a synthetic particle or a bead.

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used here, the term, "spatial label" can refer to a label which can be associated with a position in space.

As used herein, the term "stochastic barcode" can refer to a polynucleotide sequence comprising labels. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "gene-specific stochastic barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* LI.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Disclosed herein are systems and methods for identifying a signal cell label. In some embodiments, the method comprises: (a) stochastically barcoding a plurality of targets in a sample of cells using a plurality of stochastic barcodes to create a plurality of stochastically barcoded targets, wherein each of the plurality of stochastic barcodes comprises a cell label and a molecular label; (b) obtaining sequencing data of the plurality of stochastically barcoded targets; (c) determining the numbers of molecular labels with distinct sequences associated with each of the cell labels of the plurality of stochastic barcodes; (d) determining a rank of each of the cell labels of the plurality of stochastic barcodes based on the number of molecular labels with distinct sequences associated with each of the cell labels; (e) generating a cumulative sum plot based on the number of molecular labels with distinct sequences associated with each of the cell labels determined in (c) and the rank of each of the cell labels determined in (d); (f) generating a second derivative plot of the cumulative sum plot; (g) determining a minimum of the second derivative plot of the cumulative sum plot, wherein the minimum of the second derivative plot corresponds to a cell label threshold; and (h) identifying each of the cell labels as a signal cell label or a noise cell label based on the number of molecular labels with distinct sequences associated with each of the cell labels determined in (c) and the cell label threshold determined in (g).

Barcodes

Barcoding, such as stochastic barcoding, has been described in, for example, US20150299784, WO2015031691, and Fu et al, Proc Natl Acad Sci U.S.A. 2011 May 31; 108(22):9026-31 and Fan et al., Science (2015) 347(6222):1258367; the content of each of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be, for example, an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 108. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, 20, or more nucleotides.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequence (e.g., a molecular label)) can be separated by one or more spacers from another one or two of the remaining labels of the barcode. The spacer can be, for example, 1, 2, 3, 4, 5, 6, 7, 8, 9, 10, 11, 12, 13, 14, 15, 16, 17, 18, 19, 20, or more nucleotides in length. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of particles (e.g., synthetic particles such as beads). In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was stochastically barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10, or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a synthetic particle, such as a bead), but different for different solid supports (e.g., synthetic particles). In some embodiments, at least 60%, 70%, 80%, 85%, 90%, 95%, 97%, 99%, or 100% of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., synthetic particles). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example a coordinate can be fixed in reference to a substrate.

A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, a microsphere, a tube, a microcapsule, or a droplet). In some embodiments, multiple spatial labels are used together to encode one or more positions in space.

The spatial label can be identical for all barcodes attached to a given solid support (e.g., a synthetic particle such as a bead), but different for different solid supports (e.g., synthetic particles). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., synthetic particles such as a bead). A spatial label can be, or be about, 1, 2, 3, 4, 5, 10, 15, 20, 25, 30, 35, 40, 45, 50, or a number or a range between any two of these values, nucleotides in length. A spatial label can be at least, or at most, 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a synthetic particle such as a bead), but different for different solid supports (e.g., synthetic particles). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., synthetic particles). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a synthetic particle, such as a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or at most, $10^2$, $10^3$, $10^4$, $10^5$, $10^6$, $10^7$, $10^8$, or $10^9$, unique barcode sequences. The unique molecular label sequences can be attached to a given solid support (e.g., a synthetic particle).

A barcode can be, or be about, 1, 2, 3, 4, 5, 10, 15, 20, 25, 30, 35, 40, 45, 50, or a number or a range between any two of these values, nucleotides in length. A barcode can be at least, or at most, 1, 2, 3, 4, 5, 10, 15, 20, 25, 30, 35, 40, 45, 50, 100, 200, or 300 nucleotides in length.

Molecular Labels

A stochastic barcode can comprise one or more molecular labels. Molecular labels can include barcode sequences. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., a synthetic particle such as a bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. Stochastic barcodes with the unique molecular label sequences can be attached to a given solid support (e.g., a synthetic particle).

For stochastic barcoding using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A barcode can comprise one or more target-binding regions, such as capture probes. In some embodiments, a target-binding region can hybridize with a target of interest. In some embodiments, a target-binding region can comprise a nucleic acid sequence that hybridizes specifically to a target (e.g. target nucleic acid, such as a cellular nucleic acid to be analyzed). For example, a target-binding region can hybridize to a target nucleic acid at a specific gene sequence. In some embodiments, a target-binding region can comprise a nucleic acid sequence that can attach (e.g., hybridize) to a specific location of a specific target nucleic acid. In some embodiments, the target-binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target-binding region can comprise a non-specific target nucleic acid sequence. A non-specific target nucleic acid sequence can refer to a sequence that can bind to multiple target nucleic acids, independent of the specific sequence of the target nucleic acid. For example, target-binding region can comprise a random multimer sequence, or an oligo(dT) sequence that hybridizes to the poly(A) tails on mRNA molecules. A random multimer sequence can be, for example, a random dimer, trimer, quatramer, pentamer, hexamer, septamer, octamer, nonamer, decamer, or higher multimer sequence of any length. In some embodiments, the target-binding region is the same for all barcodes attached to a given synthetic particle (e.g., a bead). In some embodiments, the target-binding regions for the plurality of barcodes attached to a given synthetic particle can comprise two or more different target binding sequences. A target-binding region can be, or be about, 5, 10, 15, 20, 25, 30, 35, 40, 45, 50, or a number or a range between any two of these values, nucleotides in length. A target-binding region can be at most about 5, 10, 15, 20, 25, 30, 35, 40, 45, 50, or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

In some embodiments, a barcode does not include a target-binding region. In some embodiments, a barcode includes a region corresponding to a target-binding region with a sequence that has a low binding affinity (e.g., does not bind) to some, most, substantially all, or all of the mRNA molecules in a cell or cells of a sample. For example, a barcode can comprise a region that corresponds to a target-binding region can have a sequence that does not bind to mRNA molecules of interest. If the target-binding region of a first barcode comprises an oligo(dT) sequence that is capable of hybridizing to the poly(A) tail of an mRNA molecule, the corresponding region of a second barcode can include, for example, a sequence that is not similar, or substantially similar, to a poly(dT) sequence. If the target-binding region of a first barcode comprises a target-binding region with a sequence that is capable of hybridizing specifically to a particular gene sequence, the corresponding region of a second barcode can include, for example, a sequence that is not similar, or substantially similar, to the target-binding region.

Orientation Property

A barcode can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50, or more nucleotides in length. A linker label sequence can be at most about 5, 10, 15, 20, 25, 30, 35, 40, 45, 50, or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a particle or a synthetic particle. In some embodiments, some or all of the barcode sequence, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The synthetic particle can be, for example, a silica gel bead, a controlled pore glass bead, a magnetic bead, a Dynabead, a Sephadex/Sepharose bead, a cellulose bead, a polystyrene bead, or any combination thereof. The synthetic particle can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, a synthetic particle can be a polymeric particle, for example a deformable particle or a gel particle, functionalized with barcodes or stochastic barcodes (such as gel beads from 10× Genomics (San Francisco, CA)). In some implementation, a gel particle can comprise one or more polymer-based gels. Gel particles can be generated, for example, by encapsulating one or more polymeric precursors into droplets. Upon exposure of the polymeric precursors to an accelerator (e.g., tetramethylethylenediamine (TEMED)), a gel particle may be generated.

In some embodiments, the particle can be degradable. For example, the polymeric particle or bead can dissolve, melt, or degrade, for example, under a desired condition. The desired condition can include an environmental condition. The desired condition may result in the polymeric particle dissolving, melting, or degrading in a controlled manner. A gel particle may dissolve, melt, or degrade due to a chemical stimulus, a physical stimulus, a biological stimulus, a thermal stimulus, a magnetic stimulus, an electric stimulus, a light stimulus, or any combinations thereof.

Reagents, such as oligonucleotide barcodes, may be coupled/immobilized to the interior surface of a synthetic particle (e.g., the interior accessible via diffusion of an oligonucleotide barcode and/or materials used to generate an oligonucleotide barcode) and/or the outer surface of a gel particle or any other microcapsule described herein. The particle can be, for example, a gel bead. Association (e.g., coupling, or immobilization) may be via any form of chemical bonding (e.g., covalent bond, ionic bond) or physical phenomena (e.g., Van der Waals forces, dipole-dipole interactions, etc.). In some embodiments, association (e.g., coupling or immobilization) of a reagent to a particle or any other solid support (e.g., microcapsule) described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel particle via a disulfide bond, exposure of the disulfide bond to a reducing agent can cleave the disulfide bond and free the oligonucleotide barcode from the particle. The labile moiety may be included as part of a gel particle, bead, or microcapsule, as part of a chemical linker that links a reagent to a gel bead or microcapsule, and/or as part of a reagent. In some embodiments, at least one barcode of the plurality of barcodes can be immobilized on the particle, partially immobilized on the particle, enclosed in the particle, partially enclosed in the particle, or any combination thereof.

In some embodiments, a particle (for example a gel bead) can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the particles. Examples of these chemical changes may include, but are not limited to pH-mediated changes to the particle wall, disintegration of the particle wall via chemical cleavage of crosslink bonds, triggered depolymerization of the particle wall, and particle wall switching reactions. Bulk changes may also be used to trigger disruption of the particles.

Bulk or physical changes to the microcapsule or particles through various stimuli also offer many advantages in designing capsules to release reagents. Bulk or physical changes occur on a macroscopic scale, in which particle rupture is the result of mechano-physical forces induced by a stimulus. These processes may include, but are not limited to pressure induced rupture, particle wall melting, or changes in the porosity of the particle wall.

Biological stimuli may also be used to trigger disruption, dissolution, or degradation of particles. Generally, biological triggers resemble chemical triggers, but many examples use biomolecules, or molecules commonly found in living systems such as enzymes, peptides, saccharides, fatty acids, nucleic acids and the like. For example, particles may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the particles are released. In other cases, the proteases may be heat-activated. In another example, particles comprise a shell wall comprising cellulose. Addition of the hydrolytic enzyme chitosan serves as biologic trigger for cleavage of cellulosic bonds, depolymerization of the shell wall, and release of its inner contents.

The particles may also be induced to release their contents upon the application of a thermal stimulus. A change in temperature can cause a variety changes to the particles. A change in heat may cause melting of a particle such that the particle wall disintegrates. In other cases, the heat may increase the internal pressure of the inner components of the particle such that the particle ruptures or explodes. In still other cases, the heat may transform the particle into a shrunken dehydrated state. The heat may also act upon heat-sensitive polymers within the wall of a particle to cause disruption of the particle.

Inclusion of magnetic nanoparticles to the particle wall of microcapsules may allow triggered rupture of the particles as well as guide the particles in an array. A device of this disclosure may comprise magnetic particles for either purpose. In one example, incorporation of $Fe_3O_4$ nanoparticles into polyelectrolyte containing particles triggers rupture in the presence of an oscillating magnetic field stimulus.

A particle may also be disrupted, dissolved, or degraded as the result of electrical stimulation. Similar to magnetic particles described in the previous section, electrically sensitive particles can allow for both triggered rupture of the particles as well as other functions such as alignment in an electric field, electrical conductivity or redox reactions. In one example, particles containing electrically sensitive material are aligned in an electric field such that release of inner reagents can be controlled. In other examples, electrical fields may induce redox reactions within the particle wall itself that may increase porosity.

A light stimulus may also be used to disrupt the particles. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the particle wall. In yet another example, photo switchable materials such as azobenzene groups may be incorporated in the particle wall. Upon the application of UV or visible light, chemicals such as these undergo a reversible cis-to-trans isomerization upon absorption of photons. In this aspect, incorporation of photon switches result in a particle wall that may disintegrate or become more porous upon the application of a light trigger.

Figure 2:
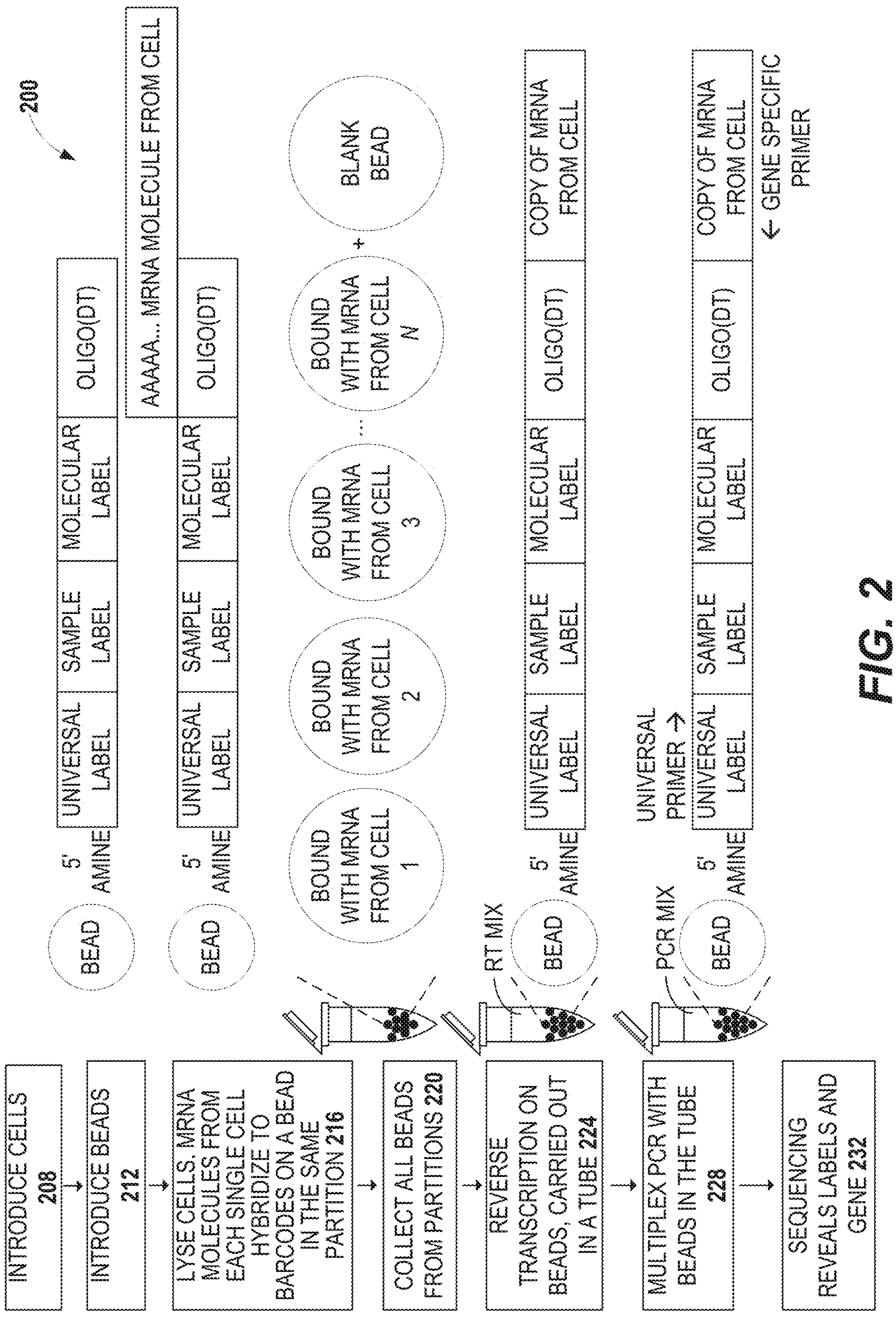
FIG. 2 shows a non-limiting exemplary workflow of barcoding and digital counting (e.g., stochastic barcoding and digital counting).

For example, in a non-limiting example of barcoding (e.g., stochastic barcoding) illustrated in FIG. 2, after introducing cells such as single cells onto a plurality of microwells of a microwell array at block 208, particles can be introduced onto the plurality of microwells of the microwell array at block 212. Each microwell can comprise one particle. The particles can comprise a plurality of barcodes. A barcode can comprise a 5' amine region attached to a particle. The barcode can comprise a universal label, a barcode sequence (e.g., a molecular label), a target-binding region, or any combination thereof.

The barcodes disclosed herein can be associated with (e.g., attached to) a solid support (e.g., a particle or a bead). The barcodes associated with a solid support can each comprise a barcode sequence selected from a group comprising at least 100 or 1000 barcode sequences with unique sequences. In some embodiments, different barcodes associated with a solid support can comprise barcode sequences of different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a particle, such as a bead). In some embodiments, stochastically barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The particles can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized" are used interchangeably, and can refer to covalent or non-covalent means for attaching barcodes to a solid support. Any of a variety of different solid supports can be used as solid supports for attaching pre-synthesized barcodes or for in situ solid-phase synthesis of barcodes.

In some embodiments, the solid support is a particle, for example a bead. The particle can comprise one or more types of solid, porous, or hollow sphere, ball, bearing, cylinder, or other similar configuration which a nucleic acid can be immobilized (e.g., covalently or non-covalently). The particle can be, for example, composed of plastic, ceramic, metal, polymeric material, or any combination thereof. A particle can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a partile can be non-spherical in shape.

The particles can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the particle (e.g., the particle to which the labels are attached) is a hydrogel bead. In some embodiments, the particle comprises hydrogel.

Some embodiments disclosed herein include one or more particles (for example beads). Each of the particles can comprise a plurality of oligonucleotides (e.g., barcodes). Each of the plurality of oligonucleotides can comprise a barcode sequence (e.g., a molecular label), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $\mathbf{10}^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiments, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $\mathbf{10}^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of a particle can vary. For example, the diameter of the particle can range from 0.1 micrometer to 50 micrometer. In some embodiments, the diameters of particles can be, or be about, 0.1, 0.5, 1, 2, 3, 4, 5, 6, 7, 8, 9, 10, 20, 30, 40, 50 micrometer, or a number or a range between any two of these values.

The diameter of the particle can be related to the diameter of the wells of the substrate. In some embodiments, the diameter of the particle can be, or be about, 10%, 20%, 30%, 40%, 50%, 60%, 70%, 80%, 90%, 100%, or a number or a range between any two of these values, longer or shorter than the diameter of the well. The diameter of the particle can be related to the diameter of a cell (e.g., a single cell entrapped by a well of the substrate). In some embodiments, the diameter of the particle can be at least, or at most, 10%, 20%, 30%, 40%, 50%, 60%, 70%, 80%, 90%, or 100% longer or shorter than the diameter of the well. The diameter of the particle can be related to the diameter of a cell (e.g., a single cell entrapped by a well of the substrate). In some embodiments, the diameter of the particle can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the particle can be at least, or at most, 10%, 20%, 30%, 40%, 50%, 60%, 70%, 80%, 90%, 100%, 150%, 200%, 250%, or 300% longer or shorter than the diameter of the cell.

A particle can be attached to and/or embedded in a substrate. A particle can be attached to and/or embedded in a gel, hydrogel, polymer and/or matrix. The spatial position of a particle within a substrate (e.g., gel, matrix, scaffold, or polymer) can be identified using the spatial label present on the barcode on the particle which can serve as a location address.

Examples of particles can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A particle can be associated with (e.g. impregnated with) quantum dots or fluorescent dyes to make it fluorescent in one fluorescence optical channel or multiple optical channels. A particle can be associated with iron oxide or chromium oxide to make it paramagnetic or ferromagnetic. Particles can be identifiable. For example, a particle can be imaged using a camera. A particle can have a detectable code associated with the particle. For example, a particle can comprise a barcode. A particle can change size, for example due to swelling in an organic or inorganic solution. A particle can be hydrophobic. A particle can be hydrophilic. A particle can be biocompatible.

A solid support (e.g., a particle) can be visualized. The solid support can comprise a visualizing tag (e.g., fluorescent dye). A solid support (e.g., a particle) can be etched with an identifier (e.g., a number). The identifier can be visualized through imaging the particles.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or particles (e.g., synthetic particles such as beads) in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be a biological molecule. For example a solid support can be, or can comprise, a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose barcodes (e.g., stochastic barcodes) of the disclosure to targets. For example, a biological molecule can comprise barcodes that are inaccessible due to folding of the biological molecule. Upon modification of the biological molecule (e.g., acetylation), the biological molecule can change conformation to expose the barcodes. The timing of the modification can provide another time dimension to the method of barcoding of the disclosure.

In some embodiments, the biological molecule comprising barcode reagents of the disclosure can be located in the cytoplasm of a cell. Upon activation, the biological molecule can move to the nucleus, whereupon barcoding can take place. In this way, modification of the biological molecule can encode additional space-time information for the targets identified by the barcodes.

Substrates and Microwell Array

As used herein, a substrate can refer to a type of solid support. A substrate can refer to a solid support that can comprise barcodes and stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a particle). A microwell can comprise combinatorial barcode reagents of the disclosure.

Synthesis of Barcodes on Solid Supports

A barcode (e.g., a stochastic barcode) can be synthesized on a solid support (e.g., a particle, such as a synthetic particle or a bead). Pre-synthesized barcodes (e.g., comprising the 5'amine that can link to the solid support) can be attached to solid supports (e.g., particles) through any of a variety of immobilization techniques involving functional group pairs on the solid support and the barcode. The barcode can comprise a functional group. The solid support (e.g., a particle) can comprise a functional group. The barcode functional group and the solid support functional group can comprise, for example, biotin, streptavidin, primary amine(s), carboxyl(s), hydroxyl(s), aldehyde(s), ketone(s), and any combination thereof. A barcode (e.g., a stochastic barcode) can be tethered to a solid support, for example, by coupling (e.g. using 1-Ethyl-3-(3-dimethylaminopropyl) carbodiimide) a 5' amino group on the barcode to the carboxyl group of the functionalized solid support. Residual non-coupled barcodes can be removed from the reaction mixture by performing multiple rinse steps. In some embodiments, the barcode and solid support are attached indirectly via linker molecules (e.g. short, functionalized hydrocarbon molecules or polyethylene oxide molecules) using similar attachment chemistries. The linkers can be cleavable linkers, e.g. acid-labile linkers or photo-cleavable linkers.

The barcodes (e.g., stochastic barcodes) can be synthesized on solid supports (e.g., particles) using any of a number of solid-phase oligonucleotide synthesis techniques, such as phosphodiester synthesis, phosphotriester synthesis, phosphite triester synthesis, and phosphoramidite synthesis. Single nucleotides can be coupled in step-wise fashion to the growing, tethered barcode. A short, pre-synthesized sequence (or block) of several oligonucleotides can be coupled to the growing, tethered barcode.

Barcodes (e.g., stochastic barcodes) can be synthesized by interspersing step-wise or block coupling reactions with one or more rounds of split-pool synthesis, in which the total pool of synthesis particles is divided into a number of individual smaller pools which are then each subjected to a different coupling reaction, followed by recombination and mixing of the individual pools to randomize the growing barcode sequence across the total pool of particles. Split-pool synthesis is an example of a combinatorial synthesis process in which a maximum number of chemical compounds are synthesized using a minimum number of chemical coupling steps. The potential diversity of the compound library thus created is determined by the number of unique building blocks (e.g. nucleotides) available for each coupling step, and the number of coupling steps used to create the library. For example, a split-pool synthesis comprising 10 rounds of coupling using 4 different nucleotides at each step will yield $4^{10}$=1,048,576 unique nucleotide sequences. In some embodiments, split-pool synthesis can be performed using enzymatic methods such as polymerase extension or ligation reactions rather than chemical coupling. For example, in each round of a split-pool polymerase extension reaction, the 3' ends of the barcodes tethered to particles in a given pool can be hybridized with the 5'ends of a set of semi-random primers, e.g. primers having a structure of 5'-$(M)_k$-$(X)_i$-$(N)_j$-3', where $(X)_i$ is a random sequence of nucleotides that is i nucleotides long (the set of primers comprising all possible combinations of $(X)_i$), $(N)_j$ is a specific nucleotide (or series of j nucleotides), and $(M)_k$ is a specific nucleotide (or series of k nucleotides), wherein a different deoxyribonucleotide triphosphate (dNTP) is added to each pool and incorporated into the tethered oligonucleotides by the polymerase.

Methods of Barcoding

The disclosure provides for methods for estimating the number of distinct targets in a sample. In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be crosslinked to the barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, TRITON™ X-100, TWEEN© 20, or NONIDET™ P-40 (NP-40)), an organic solvent (e.g. methanol or acetone), or digestive enzymes (e.g. proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about, or at most about, 0.01 M, 0.05 M, 0.1 M, 0.5 M, or 1 M or more or less Tris HCl. A lysis buffer can comprise about 0.01 M, 0.05 M, 0.1 M, 0.5 M, or 1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, TRITON™ X, TWEEN©, NONIDET™ P-40 (NP-40)). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1 mM, 5 mM, 10 mM, 15 mM, 20 mM, 25 mM, or 30 mM, or more. The concentration of a chelating agent in the lysis buffer can be at most about 1 mM, 5 mM, 10 mM, 15 mM, 20 mM, 25 mM, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1 mM, 5 mM, 10 mM, 15 mM, or 20 mM or more. The concentration of the reducing reagent in the lysis buffer can be at most about 1 mM, 5 mM, 10 mM, 15 mM, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, 20, or more minutes. A lysed cell can comprise at least about 100000, 200000, 300000, 400000, 500000, 600000, 700000, or more target nucleic acid molecules. A lysed cell can comprise at most about 100000, 200000, 300000, 400000, 500000, 600000, 700000, or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on particles. For example, single-stranded nucleotide fragments can hybridize to the target-binding regions of barcodes.

Attachment can further comprise ligation of a barcode's target recognition region and a portion of the target nucleic acid molecule. For example, the target-binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the particles to which the target-barcode molecules are attached.

The retrieval of solid support-based collections of attached target-barcode molecules can be implemented by use of magnetic particles and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Nucleic Acid Extension Reaction (e.g., Reverse Transcription)

The disclosure provides for a method to create a target-barcode conjugate using a nucleic acid extension reaction, such as reverse transcription (e.g., at block 224 of FIG. 2). The target-barcode conjugate can comprise the barcode and a complementary sequence of all or a portion of the target nucleic acid (i.e. a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cell label and/or barcode sequence (e.g., molecular label). The amplification reactions can comprise amplifying at least a portion of a sample tag, a cell label, a spatial label, a barcode (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75% 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled-amplicon (e.g., a stochastically labeled-amplicon). The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the particle (e.g., a bead) using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded fragments. The barcodes sequences of different barcodes (e.g., the molecular labels of different stochastic barcodes) can be different from one another. Generating an indexed library of the barcoded targets (e.g., stochastically barcoded targets) includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, barcode sequences (e.g., molecular labels), and sequences of nucleotide fragments of the one or more copies of the targets, for example at block 232 of FIG. 2.

Figure 3:
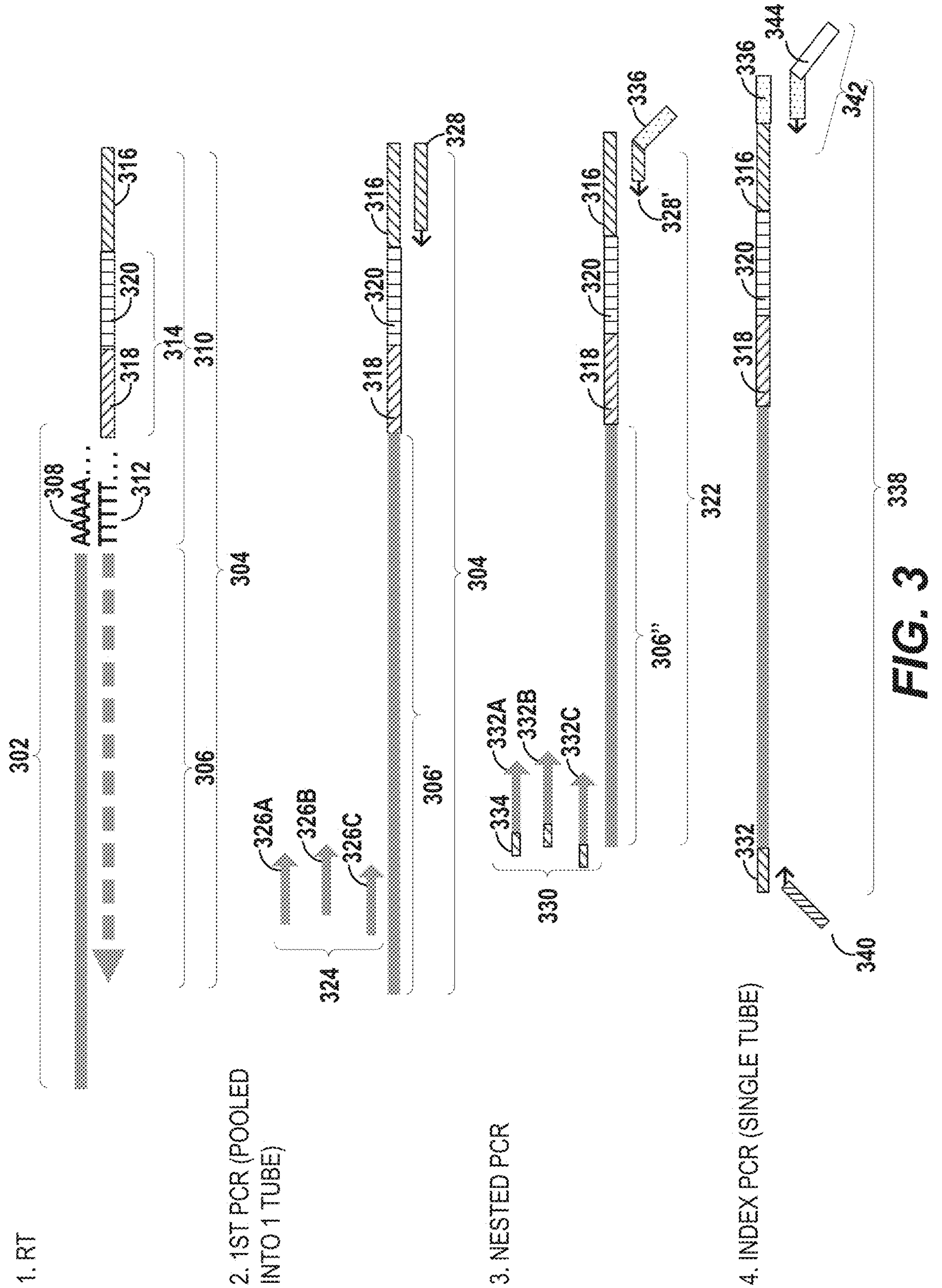
FIG. 3 is a schematic illustration showing a non-limiting exemplary process for generating an indexed library of the barcoded targets (e.g., stochastically barcoded targets) from a plurality of targets.

FIG. 3 is a schematic illustration showing a non-limiting exemplary process of generating an indexed library of the barcoded targets (e.g., stochastically barcoded targets), for example mRNAs. As shown in step 1, the reverse transcription process can encode each mRNA molecule with a unique barcode sequence (e.g., molecular label), a cell label, and a universal PCR site. For example, RNA molecules 302 can be reverse transcribed to produce labeled cDNA molecules 304, including a cDNA region 306, by the hybridization (e.g., stochastic hybridization) of a set of barcodes (e.g., stochastic barcodes) 310) to the poly(A) tail region 308 of the RNA molecules 302. Each of the barcodes 310 can comprise a target-binding region, for example a poly(dT) region 312, a barcode sequence or a molecular label 314, and a universal PCR region 316.

In some embodiments, the cell label can include 3 to 20 nucleotides. In some embodiments, the barcode sequence (e.g., molecular label) can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a 1st PCR primer pool and a 1st universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. For example, the nested PCR labeled amplicons 322 can be further amplified by nested PCR. The nested PCR can comprise multiplex PCR with nested PCR primers pool 330 of nested PCR primers 332*a-c* and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Nuclei Barcoding Method and Composition

Disclosed herein includes methods, compositions, and kits for performing both single nuclei capture and barcoding (e.g., in a single step). Single nuclei sequencing can be used for single cell transcriptome analysis (or other single cell omics or multiomics analysis, such as proteomics analysis to determine protein expression profiles of single cells) while minimizing (e.g., eliminating) the need of performing or preparing single cell suspensions. Preparing single cell suspensions can be technically challenging, for example, for certain sample preparations, such as frozen tissues. The method includes an isolation step of nuclei. For example, a nuclear envelope specific antibody, such as anti-LAMIN, can be used to separate nucleic from other subcellular components.

In some embodiments, these antibodies can be associated with (e.g., conjugated with) an epitope (such as a strong epitope, including biotin, digoxygenin, or fluorescein) or a molecular barcode that represents that particular antibody and/or both. The associated epitope (e.g., a conjugated epitope) can allow for a quick isolation step of nuclei without the use of an ultracentrifugation step. The associated barcode (e.g., a conjugated barcode) can be used to perform sample indexing, for example, when multiple samples are pooled together to perform a single downstream next generation sequencing (NGS) library preparation procedure. In some embodiments, sample indexing can include sample indexing on single nuclei. In some embodiments, sample indexing can include sample indexing on single nuclei and single cells.

In some embodiments, the antibody barcode can be, or can include, a nucleotide barcode. For example, a nucleotide barcode can be at least 10 base pairs in length. The nucleotide barcode can be, or can include, deoxyribonucleic acid (DNA), ribonucleic acid (RNA), locked nucleic acid (LNA), peptide nucleic acid (PNA), or other synthetic nucleotide compatible with reverse transcription or other DNA polymerization step. The nucleotide barcode can optionally include a 3' poly(dA) tail to mimic endogenous cellular mRNAs and to make the barcode compatible with downstream library preparation. The barcode sequence information can then be demultiplexed after sequencing along with each nucleus to determine which sample the nucleus originated from. Barcoded antibodies and their uses, such as sample indexing of cells using barcoded antibodies, have been described in U.S. Patent Application Publication No. 2018/0088112 and U.S. patent application Ser. No. 15/937,713; the content of each is incorporated by reference in its entirety.

Nuclei Barcoding Method

Figure 4A:
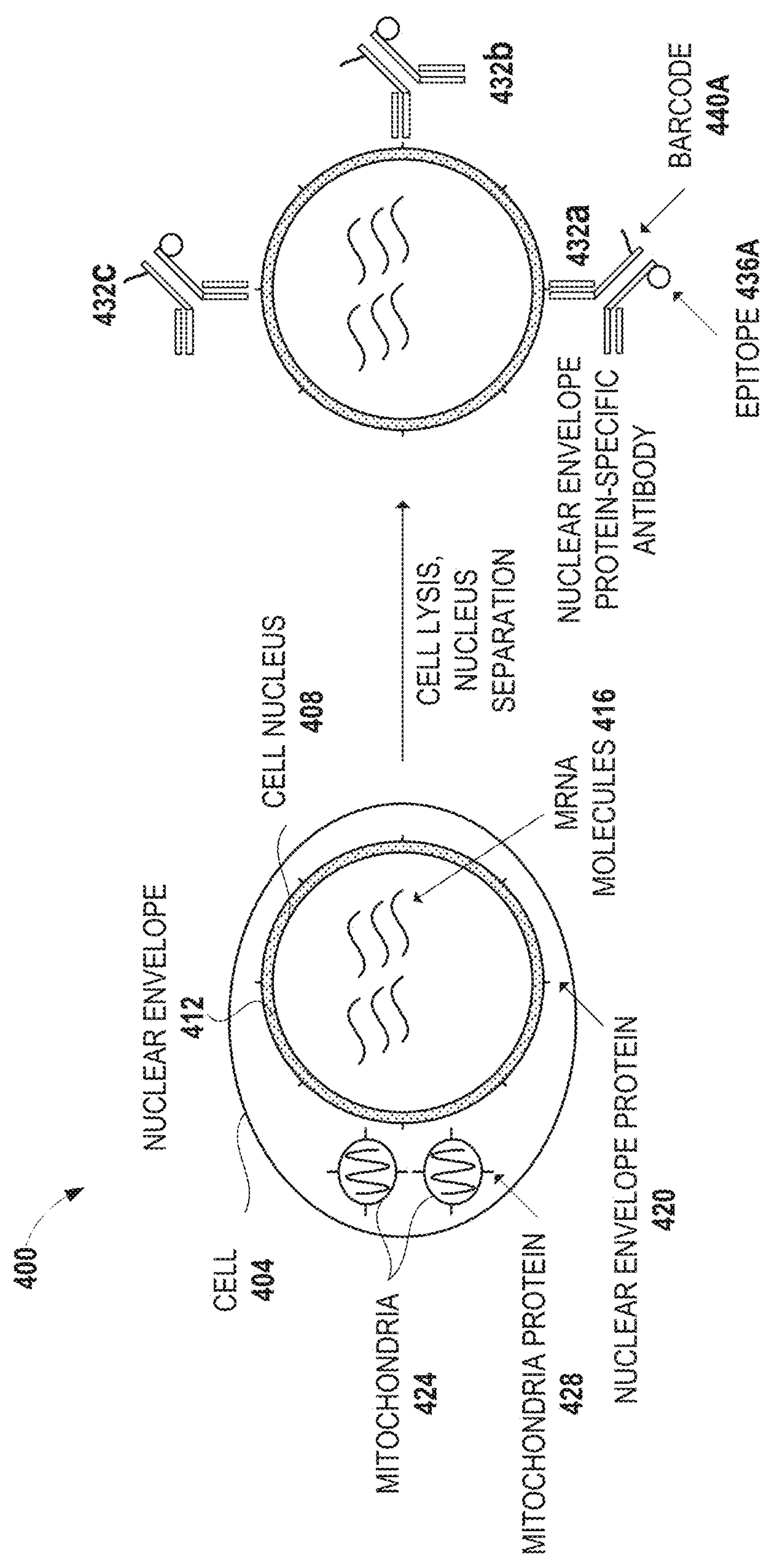
FIGS. 4A-4B show a non-limiting exemplary schematic illustration of a nuclei barcoding workflow (e.g., stochastic barcoding).
Figure 4B:
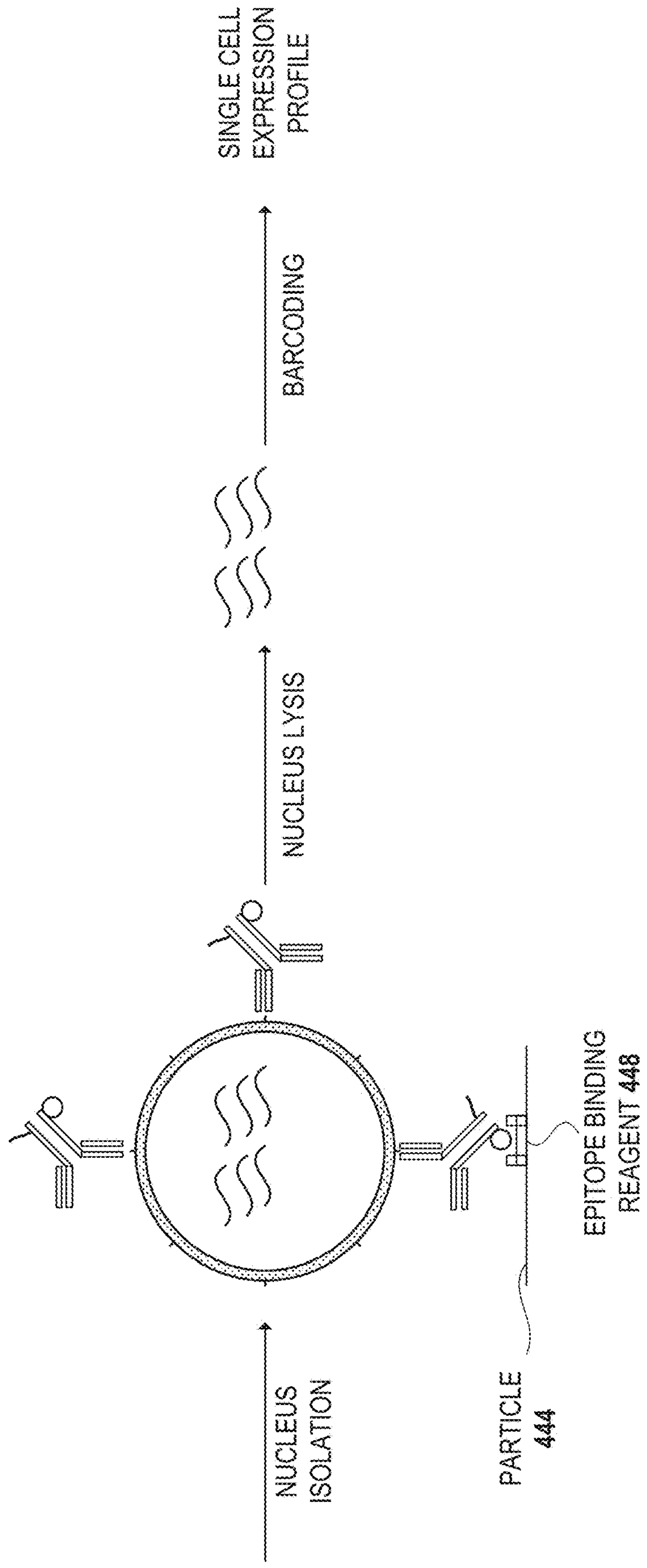

FIGS. 4A-4B show a non-limiting exemplary schematic illustration of a nuclei barcoding workflow (e.g., stochastic barcoding). Cell lysis can be performed using a homogenizer (e.g., a Dounce homogenizer), a detergent, or an enzymatic method. Nuclei can be captured by, for example, an antibody specific for a nuclear envelope protein (such as LAMIN) conjugated with an epitope (e.g., a strong epitope such as biotin, digoxigenin (DIG), and fluorescein) and optionally, a barcode oligonucleotide to label nuclei. Secondary antibody against the epitope can be used to pull nuclei down for purification (e.g., away from cytoplasmic fragments) followed by RNA/DNA capture using a single cell analysis assay (such as Rhapsody™ assay (Becton, Dickinson and Company (Franklin Lakes, NJ)).

Disclosed herein include embodiments of a method 400 for determining the numbers of targets in a plurality of cells (such as the cell 404 illustrated in FIGS. 4A-4B). The method 400 can include cell lysis, nucleus separation and isolation, nucleus lysis, and barcoding for single cell analysis (e.g., single cell transcriptome or proteome analysis)

In some embodiments, the method 400 comprises: isolating a plurality of nuclei of a plurality of cells using a nuclei-isolation composition. The plurality of nuclei isolated can include a nucleus 408 comprising a nuclear envelope 412 illustrated in FIGS. 4A-4B. The contents (e.g., mRNA contents or protein contents) of an isolated nucleus, such as mRNA molecules 416 of the nucleus 408, can be analyzed using a single cell method (such as Rhapsody™ assay (Becton, Dickinson and Company (Franklin Lakes, NJ)). The nuclei-isolation composition can comprise a nuclei-binding reagent. The nuclei-binding reagent can capable of specifically binding to one or more components of a nucleus (e.g., a nuclear envelope protein 420 on the nuclear envelope 412 of the cell nucleus 408 of the cell 404 illustrated in FIGS. 4A-4B).

The number of nuclei isolated can be different in different implementations. In some embodiments, the number of nuclei isolated can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, $10^7$, $10^8$, $10^9$, $10^{10}$, $10^{11}$, $10^{12}$, or a number or a range between any two of these values. In some embodiments, the number of nuclei isolated can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, $10^7$, $10^8$, $10^9$, $10^{10}$, $10^{11}$, or $10^{-12}$.

The number of nuclei-binding reagent(s) in the nuclei-isolation composition can be different in different implementations. In some embodiments, the number of the nuclei-binding reagent(s) in the nuclei-isolation composition can be, or can be about, 1,2, 3,4, 5,6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of the nuclei-binding reagent(s) in the nuclei-isolation composition can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The nuclei-binding reagents can bind to one or more components of the nucleus. In some embodiments, the number of nuclei-binding reagent(s) that bind to one component of the nucleus can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of nuclei-binding reagent(s) that bind to one component of the nucleus can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The number of the components of the nucleus that the nuclei-binding reagents in the nuclei-isolation composition can bind to can be different in different implementations. In some embodiments, the number of the components of the nucleus that the nuclei-binding reagents in the nuclei-isolation composition can bind to can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of the components of the nucleus that the nuclei-binding reagents in the nuclei-isolation composition can bind to can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The method 400 can include barcoding a plurality of targets (e.g., mRNA molecules 416 illustrated in FIGS. 4A-4B) in the plurality of nuclei using a plurality of barcodes to generate a plurality of barcoded targets. Each of the plurality of barcodes can comprise a molecular label sequence and a target-binding region, and the molecular label sequences of at least two barcodes of the plurality of barcodes can comprise different sequences. The method 400 can include obtaining sequencing data of the plurality of barcoded target targets. The method 400 can include estimating the number of each of the plurality of targets in the plurality of cells using the molecular label sequences of the plurality of barcodes in the sequencing data. In FIGS. 4A-4B, the cell 404 can include one or more mitochondria 424 with mitochondria protein 428.

In some embodiments, isolating the plurality of nuclei comprises: contacting the plurality of nuclei of the plurality of cells with the nuclei-isolation composition (e.g., a nuclear envelope protein-specific antibody 432*a*-432*c* illustrated in FIGS. 4A-4B) to generate nuclei bound to the nuclei-binding reagent. Isolating the plurality of nuclei can comprise: isolating the nuclei bound to the nuclei-binding reagent using a reagent capable of specifically binding to the nuclei-binding reagent (e.g., an epitope binding reagent 444 illustrated in FIGS. 4A-4B).

Components of a Nucleus and a Nuclei-Binding Reagent

In some embodiments, the nuclei-binding reagent is associated with a first epitope (e.g., the epitope 436 illustrated in FIGS. 4A-4B), and the reagent capable of specifically binding to the nuclei-binding reagent comprises a first epitope-binding reagent. The first epitope can comprise biotin, hapten, or a combination thereof. The hapten can comprise digoxigenin, 2,4-dinitrophenol, fluorescein, or a combination thereof. The reagent capable of specifically binding to the nuclei-binding reagent can comprise an anti-hapten antibody. The reagent capable of specifically binding to the nuclei-binding reagent can comprise avidin, streptavidin, neutravidin, or a combination thereof. In some embodiments, first epitope and/or first epitope-binding reagent can be an affinity moiety such as biotin, streptavidin, heparin, an aptamer, a click-chemistry moiety, digoxigenin, primary amine(s), carboxyl(s), hydroxyl(s), aldehyde(s), ketone(s), or any combination thereof. The first epitope and first epitope-binding reagent can be members of a binding pair, for example, biotin/streptavidin.

The number of different first epitopes associated with the nuclei-binding reagent can be different in different implementations. In some embodiments, the number of different first epitopes associated with the nuclei-binding reagent can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values. In some embodiments, the number of different first epitopes associated with the nuclei-binding reagent can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

The number of molecules of a first epitope associated with the nuclei-binding reagent can be different in different implementations. In some embodiments, the number of molecules of a first epitopes associated with the nuclei-binding reagent can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values. In some embodiments, the number of molecules of a first epitope associated with the nuclei-binding reagent can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, the nuclei-binding reagent comprises a primary antibody (e.g., a nuclear envelope protein-specific antibody 432*a*-432*c* illustrated in FIGS. 4A-4B) capable of specifically binding to the one or more components of the nucleus, and the reagent capable of specifically binding to the nuclei-binding reagent comprises a secondary antibody capable of specifically binding to the primary antibody.

In some embodiments, the nuclei-binding reagent comprises a nuclear envelope surface component-binding reagent (e.g., a nuclear envelope protein-specific antibody), and the nuclei-binding reagent can be capable of specifically binding to one or more nuclear envelope surface components.

In some embodiments, the nuclei-binding reagent comprises a carbohydrate-binding reagent. The carbohydrate-binding reagent can comprise a carbohydrate-binding protein. The carbohydrate-binding protein can comprise a lectin. The lectin can comprise a mannose binding lectin, a galactose binding lectin, an N-acetylgalactosamine binding lectin, an N-acetylglucosamine binding lectin, a N-acetylneuraminic acid binding lectin, a fucose binding lectin, or a combination thereof. The lectin can comprise Concanavalin A (ConA), Lentil lectin (LCH), Snowdrop lectin (GNA), *Ricinus communis* Agglutinin (RCA), Peanut agglutinin (PNA), Jacalin (AIL), Hairy vetch lectin (VVL), Wheat Germ Agglutinin (WGA), Elderberry lectin (SNA), *Maackia amurensis* leukoagglutinin (MAL), *Maackia amurensis* hemoagglutinin (MAH), *Ulex europaeus* agglutinin (UEA), *Aleuria aurantia* lectin (AAL), or a combination thereof. The lectin can be, or comprise, an agglutinin. The agglutinin can be, or comprise, Wheat Germ Agglutinin (WGA). The carbohydrate-binding protein can be from, or derived from, an animal, a bacterium, a virus, a fungus, or a combination thereof. The carbohydrate-binding protein can be from, or derived from, a plant. The plant can be *Canavalia ensiformis, Lens culinaris, Galanthus nivalis, Ricinus communis, Arachis hypogaea, Artocarpus integrifolia, Vicia villosa, Triticum vulgaris, Sambucus nigra, Maackia amurensis, Ulex europaeus, Aleuria aurantia*, or a combination thereof.

In some embodiments, the one or more components of the nucleus comprise a sugar, an oligosaccharide, a polysaccharides, a derivative thereof, or a combination thereof. The one or more components of the nucleus can comprise s a monosaccharide, a disaccharide, a polyol, a malto-oligosaccharide, a non-malto-oligosaccharide, a starch, a non-starch polysaccharide, a derivative thereof, or a combination thereof. The one or more components of the nucleus can comprise glucose, galactose, fructose, xylose, sucrose, lactose, maltose, trehalose, sorbitol, mannitol, maltodextrin, raffinose, stachyose, fructo-oligosaccharid, amylose, amylopectin, modified starch, glycogen, cellulose, hemicellulose, pectin, hydrocolloid, a derivative thereof, or a combination thereof. The one or more components of the nucleus can comprise a α-D-mannosyl residue, α-D-glucosyl residue, a branched α-mannosidic structure of high α-mannose type, a branched α-mannosidic structure of hybrid type and biantennary complex type N-Glycan, a fucosylated core region of bi- and triantennary complex type N-Glycan, a α 1-3 and a 1-6 linked high mannose structure, Galβ1-4GalNAcβ1-R, Galβ1-3GalNAcα1-Ser/Thr, (Sia)Galβ1-3GalNAcα1-Ser/Thr, GalNAcα-Ser/Thr, GlcNAcβ1-4GlcNAcβ1-4GlcNAc, Neu5Ac (sialic acid), Neu5Acα2-6Gal(NAc)-R, Neu5Ac/Gcα2,3Galβ1,4Glc(NAc), Neu5Ac/Gcα2,3Galβ1,3(Neu5Acα2,6)GalNac, Fucα1-2Gal-R, Fucα1-2Galβ1-4(Fucα1-3/4)Galβ1-4GlcNAc, R2-GlcNAcβ1-4(Fucα1-6)GlcNAc-R1, a derivative thereof, or a combination thereof. The one or more components of the nucleus can comprise a glycoprotein, a glycolipid, or a combination thereof.

In some embodiments, the one or more components of the nucleus comprise Lamin, Emerin, Nesprin, Nurim, UNC-83, Klar, ZYG-12, Kmslp, UNC-84, Klaroid, SUN-1, Sadlp, LBR, MAN1, LAP1, LAP2, LINK, a nuclear pore complex, a portion thereof, or a combination thereof. The number of the one or more components of the nucleus can be different in different implementations. In some embodiments, the number of the one or more components of the nucleus can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of the one or more components of the nucleus can be at least, or can be at most, 1,2, 3,4, 5,6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

Nucleus-Isolation Particle

In some embodiments, the nuclei-binding reagent is associated with a nucleus-isolation particle. The reagent capable of specifically binding to the nuclei-binding reagent can be associated with the nucleus-isolation particle (e.g., a particle 448 with a surface illustrated in FIGS. 4A-4B). The reagent capable of specifically binding to the nuclei-binding reagent can be immobilized, or partially immobilized, on the nucleus-isolation particle. For example, the reagent capable of specifically binding to the nuclei-binding reagent (such as the epitope binding reagent 444) can be reversibly, non-reversibly, covalently, non-covalently, or a combination thereof, associated with the nucleus-isolation particle. As another example, the reagent capable of specifically binding to the nuclei-binding reagent can embedded, partially embedded, non-embedded, enclosed, partially enclosed, non-enclosed, or a combination thereof, in the nucleus-isolation particle. In some embodiments, the first epitope binding reagent is be associated with (e.g., immobilized, partially immobilized, enclosed, partially enclosed) the nucleus-isolation particle via a cleavable linker. The cleavable linker can operably link the first epitope binding reagent to the nucleus isolation particle. The cleavable linker can comprise a chemically cleavable linkage, a photocleavable linkage, an acid labile linker, a heat sensitive linkage, an enzymatically cleavable linkage, or a combination thereof. There are provided, in some embodiments of the methods and compositions disclosed herein, null particles. In some embodiments, the null particles do not comprise a plurality of barcodes, a magnetic property, and/or a reagent capable of specifically binding to the nuclei binding reagent (e.g., a first epitope binding reagent). The null particles can resemble the nucleus isolation particles in all aspects other than the absence of a plurality of barcodes, a magnetic property, and/or a first epitope binding reagent. There is provided, in some embodiments of the methods and compositions disclosed herein, free first epitope. Free first epitope can comprise all or a portion of the first epitope. In some embodiments, the free first epitope can bind unbound first epitope binding reagent.

In some embodiments, the nucleus-isolation particle comprises a nucleus-isolation bead. The nucleus-isolation particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The nucleus-isolation particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The nucleus-isolation particle can be disruptable. The nucleus-isolation particle can comprise a nucleus-isolation disruptable hydrogel particle.

In some embodiments, isolating the nuclei bound to the nuclei-binding reagent can comprise: isolating the nucleus-isolation particle by magnetic removal, centrifugation, or any combination thereof. In some embodiments, the plurality of barcodes is associated with the nucleus-isolation particle. At least one barcode of the plurality of barcodes can be immobilized on the nucleus-isolation particle. At least one barcode of the plurality of barcodes can be partially immobilized on the nucleus-isolation particle. At least one barcode of the plurality of barcodes can be enclosed in the nucleus-isolation particle. At least one barcode of the plurality of barcodes can be partially enclosed in the nucleus-isolation particle. At least one barcode of the plurality of barcodes can be not enclosed in the nucleus-isolation particle. At least one barcode of the plurality of barcodes can be embedded in the nucleus-isolation particle. At least one barcode of the plurality of barcodes can be partially embedded in the nucleus-isolation particle. At least one barcode of the plurality of barcodes can be not embedded in the nucleus-isolation particle.

Nuclei Indexing Oligonucleotide

In some embodiments, the nuclei-binding reagent can comprise a nuclei indexing oligonucleotide (e.g., a barcode 440*a* associated with the nuclear envelope protein-specific antibody 432*a* illustrated in FIGS. 4A-4B). The nuclei indexing oligonucleotide can comprise a nuclei indexing sequence. The method 400 can comprise: barcoding the nuclei indexing oligonucleotides using the plurality of barcodes (e.g., for sample indexing of cell nuclei) to generate a plurality of barcoded nuclei indexing oligonucleotides; and obtaining sequencing data of the plurality of barcoded nuclei indexing oligonucleotides. Barcoding the nuclei indexing oligonucleotides can comprise: stochastically barcoding using the plurality of barcodes to generate the plurality of barcoded nuclei indexing oligonucleotides. Barcoding the nuclei indexing oligonucleotides using the plurality of barcodes can comprise: contacting the plurality of barcodes with the nuclei indexing oligonucleotides to generate barcodes hybridized to the nuclei indexing oligonucleotides; and extending the barcodes hybridized to the nuclei indexing oligonucleotides to generate the plurality of barcoded nuclei indexing oligonucleotides. Extending the barcodes can comprise: extending the barcodes using a DNA polymerase to generate the plurality of barcoded nuclei indexing oligonucleotides. Extending the barcodes can comprise: extending the barcodes using a reverse transcriptase to generate the plurality of barcoded nuclei indexing oligonucleotides.

The number of nuclei indexing oligonucleotide(s) associated with (e.g., attached to, conjugated to, etc.) the nuclei-binding reagent can be different in different implementations. In some embodiments, the number of nuclei indexing oligonucleotide(s) associated with the nuclei-binding reagent can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of nuclei indexing oligonucleotide(s) associated with the nuclei-binding reagent can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The nuclei indexing oligonucleotides associated with the nuclei-binding reagent can have identical sequences (or identical nuclei indexing sequences) or different sequences (or different nuclei indexing sequences). In some embodiments, the number of nuclei indexing oligonucleotides associated with the nuclei-binding reagent with an identical sequence (or an identical nuclei indexing sequence) can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of nuclei indexing oligonucleotides associated with the nuclei-binding reagent with an identical sequence (or an identical nuclei indexing sequence) can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000. In some embodiments, the number of nuclei indexing oligonucleotides associated with the nuclei-binding reagent with different sequences (or different nuclei indexing sequences) can be, or can be about, 1, 2, 3, 4, 5, 6,7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of nuclei indexing oligonucleotides associated with the nuclei-binding reagent with different sequences (or different nuclei indexing sequences) can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

In some embodiments, the method 400 can comprise: amplifying the plurality of barcoded nuclei indexing oligonucleotides to produce a plurality of barcoded nucleus indexing amplicons. Amplifying the plurality of barcoded nuclei indexing oligonucleotides can comprise: amplifying, using polymerase chain reaction (PCR), at least a portion of the molecular label sequence and at least a portion of the nuclei indexing oligonucleotide. Obtaining the sequencing data of the plurality of barcoded nuclei indexing oligonucleotides can comprise: obtaining sequencing data of the plurality of barcoded nucleus indexing amplicons. Obtaining the sequencing data of the plurality of barcoded nuclei indexing oligonucleotides can comprise: sequencing the at least a portion of the molecular label sequence and the at least a portion of the nuclei indexing oligonucleotide.

Barcoding Particle

In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can comprise a barcoding bead. The barcoding particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The barcoding particle can comprise a disruptable hydrogel particle.

Barcodes and Barcoding

In some embodiments, barcoding the plurality of targets using the plurality of barcodes to generate the plurality of barcoded targets comprises: contacting copies of the targets with target-binding regions of the barcodes; and reverse transcribing the plurality targets using the plurality of barcodes to generate the plurality of barcoded targets. The method can 400 comprise: prior to obtaining the sequencing data of the plurality of barcoded targets, amplifying the plurality of barcoded targets to generate a plurality of amplified barcoded targets. Amplifying the barcoded targets to generate the plurality of amplified barcoded targets can comprise: amplifying, using polymerase chain reaction (PCR), the barcoded targets to generate the plurality of amplified barcoded targets. The method 400 can comprise: amplifying the plurality of amplified barcoded targets to generate a plurality of barcoded targets amplicons. Amplifying the plurality of amplified barcoded targets can comprise: amplifying the molecular label sequence and the sequence of a target of the plurality of targets, or a portion thereof, to generate the plurality of barcoded targets amplicons. Amplifying the plurality of amplified barcoded targets can comprise: amplifying, using polymerase chain reaction (PCR), the plurality of amplified barcoded targets to generate the plurality of barcoded targets amplicons. Barcoding the plurality of targets of the cell using the plurality of barcodes to generate the plurality of barcoded targets can comprise: stochastically barcoding the plurality of targets of the cell using a plurality of stochastic barcodes to generate a plurality of stochastically barcoded targets.

In some embodiments, each of the plurality of barcodes comprises a cell label sequence, a binding site for a universal primer, or any combination thereof, and the cell label sequences of at least two barcodes of the plurality of barcodes comprise an identical sequence. The target-binding region can comprise a poly(dT) region. At least 100 molecular label sequences of the plurality of barcodes can comprise different sequences. At least 1000 molecular label sequences of the plurality of barcodes can comprise different sequences. At least 10000 molecular label sequences of the plurality of barcodes can comprise different sequences. The molecular label sequences of the plurality of barcodes can comprise random sequences. The target-binding region can comprise a gene-specific sequence, an oligo(dT) sequence, a random multimer, or any combination thereof.

Cell Lysis

In some embodiments, the method 400 comprises: prior to barcoding the plurality of targets in the plurality of nuclei using the plurality of barcodes to generate the plurality of barcoded targets, lysing the plurality of nuclei. In some embodiments, the method 400 comprises: prior to isolating the plurality of nuclei of the plurality of cells using the nuclei-isolation composition, lysing the plurality of cells without lysing nuclei of the plurality of cells.

Nuclei Barcoding Composition

Disclosed herein includes embodiments of a barcoding composition. In some embodiments, the barcoding composition comprises: a nuclei-isolation composition comprising a nuclei-binding reagent, wherein the nuclei-binding reagent is capable of specifically binding to one or more components of a nucleus; and a plurality of barcodes, wherein each of the plurality of barcodes comprises a molecular label sequence and a target-binding region, and wherein the molecular label sequences of at least two barcodes of the plurality of barcodes comprise different sequences. In some embodiments, the composition comprises: a reagent capable of specifically binding to the nuclei-binding reagent. The nuclei-binding reagent can be associated with a first epitope, and the reagent capable of specifically binding to the nuclei-binding reagent can comprise a first epitope-binding reagent. In some embodiments, the first epitope binding reagent is associated with (e.g., immobilized, partially immobilized, enclosed, partially enclosed) the nucleus-isolation particle via a cleavable linker. The cleavable linker can operably link the first epitope binding reagent to the nucleus isolation particle. The cleavable linker can comprise a chemically cleavable linkage, a photocleavable linkage, an acid labile linker, a heat sensitive linkage, an enzymatically cleavable linkage, or a combination thereof. In some embodiments, the nuclei-binding reagent comprises a primary antibody capable of specifically binding to the one or more components of the nucleus, and the reagent capable of specifically binding to the nuclei-binding reagent comprises a secondary antibody capable of specifically binding to the primary antibody. In some such embodiments, said secondary antibody is linked to the nucleus isolation particle via a cleavable linker. In some embodiments, the nuclei-binding reagent comprises a carbohydrate-binding reagent. The carbohydrate-binding reagent can comprise a carbohydrate-binding protein. In some embodiments, the nuclei-binding reagent is associated with a nucleus-isolation particle. In some embodiments, the plurality of barcodes is associated with the nucleus-isolation particle. In some embodiments, the nuclei-binding reagent can comprise a nuclei indexing oligonucleotide, and wherein the nuclei indexing oligonucleotide comprises a nuclei indexing sequence. The plurality of barcodes can be associated with a barcoding particle.

Organelles Removal Method and Composition

Also disclosed herein includes methods, compositions, and systems for performing organelles removal or isolation for single cell transcriptome analysis (or other single cell omics or multiomics analysis, such as proteomics analysis to determine protein expression profiles of single cells). In some embodiments, an antibody, such as an antibody associated with an epitope, can be used to perform an organelles removal step. For example, an antibody conjugated with one or more strong epitopes can be used for an organelles removal step. With an organelles removal step, cytoplasmic and/or nuclear RNA for NGS library preparation with fewer contaminants can be obtained. For example, purified or cleaner cytoplasmic and/or nuclear RNA for NGS library preparation can be obtained. An organelles removal step can be useful for single cell library preparations because organelle-specific RNAs, such as mitochondrial RNAs, can contribute to the sequencing reads (e.g., the majority of sequencing reads). In some embodiments, an organelles removal step includes removal of mitochondria with a mitochondria-specific antibody (or another mitochondria-specific binding reagent). For example, an organelles removal step can include removal of mitochondria with a mitochondria-specific antibody (or another mitochondria-specific binding reagent) in a single step while performing one or more downstream processes in a mitochondria-depleted pool of RNAs. The downstream processes can include cDNA synthesis for transcriptome analysis and a nucleic acid extension reaction for single-cell proteomics analysis. In some embodiments, mitochondrial contamination can be reduced (e.g., eliminated) for single cell analysis (e.g., whole transcriptome analysis or proteomics analysis).

In some embodiments, nuclei barcoding and isolation can occur in a single step. In some embodiments, mitochondrial content (e.g., RNA) depletion can occur at the beginning of library preparation. In some embodiments, nuclei barcoding and isolation and organelles removal can occur in a single step or close in time.

Figure 5A:
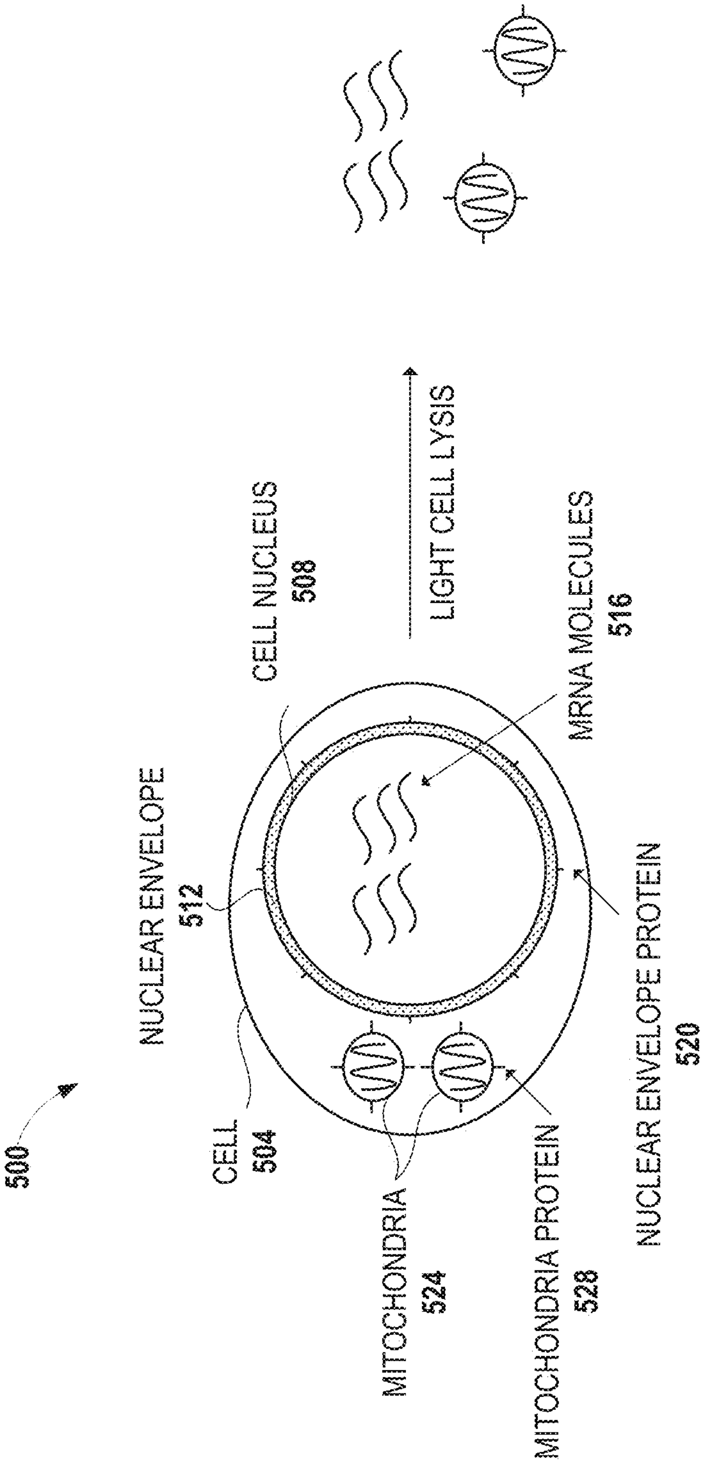
FIGS. 5A-5B show a non-limiting exemplary schematic illustration of a barcoding workflow (e.g., stochastic barcoding) with organelles (e.g., mitochondria) removal.
Figure 5B:
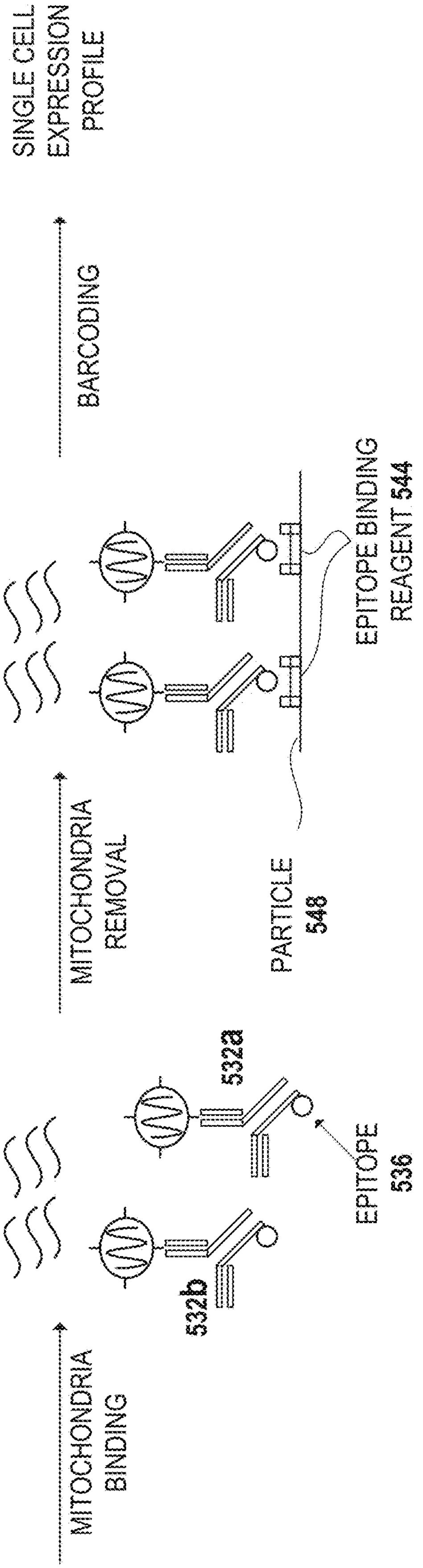

FIGS. 5A-5B show a non-limiting exemplary schematic illustration of a barcoding workflow (e.g., stochastic barcoding) with organelles (e.g., mitochondria) removal. The method 500 can include cell lysis (e.g., using a light lysis buffer to lyse a cell without lysing one or more organelles), organelles binding and removal (such as mitochondria binding and removal), followed by single cell analysis (e.g., single cell expression profile analysis). Selective removal of organelles such as mitochondria by, for example, an antibody associated with (e.g., conjugated with) an epitope (e.g., a strong epitope such as biotin, fluorescein, and DIG) may reduce (e.g., minimize or avoid) NGS library contamination. The organelles removal step can be part of a single cell workflow, such as the nuclei barcoding method 400 described with reference to FIGS. 4A-4B or the Rhapsody™ assay (Becton, Dickinson and Company (Franklin Lakes, NJ)).

In some embodiments, the method 500 comprises: prior to, or when, isolating the plurality of nuclei of the plurality of cells using the nuclei-isolation composition, permeating the plurality of cells (e.g., selectively permeabilizing and/or lysing the plasma membrane while keeping the membranes of one or more organelles intact); and depleting one or more organelles (e.g., mitochondria 524) of the plurality of cells using an organelles-capture composition comprising an organelles-binding reagent (e.g., an antibody 532*a* illustrated in FIGS. 5A-5B), wherein the organelles-binding reagent is capable of specifically binding to one or more components of the one or more organelles of the plurality of cells. Depleting the one or more organelles can comprise: contacting the one or more organelles of the plurality of cells with the organelles-capture composition to generate one or more organelles bound to the organelle component-binding reagent. Depleting the one or more organelles can comprise: depleting the one or more organelles bound to the organelles-binding reagent using a reagent capable of specifically binding to the organelles-binding reagent. The organelles-binding reagent can be associated with a second epitope (e.g., an epitope 536), and the reagent capable of specifically binding to the organelles-binding reagent (e.g., an epitope binding reagent 544) can comprise a second epitope-binding reagent.

The number of organelles-binding reagents in an organelles-capture composition can be different in different implementations. In some embodiments, the number of organelles-binding reagents in an organelles-capture composition can be, or can be about, 1,2, 3,4, 5,6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of organelles-binding reagents in an organelles-capture composition can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The number of organelles-binding reagent(s) in an organelles-capture composition that bind to an organelle can be different in different implementations. In some embodiments, the number of organelles-binding reagent(s) in an organelles-capture composition that bind to an organelle can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of organelles-binding reagent(s) in an organelles-capture composition that bind to an organelle can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The number organelles that the organelles-binding reagents in an organelles-capture composition can bind to can be different in different implementations. In some embodiments, the number organelles that the organelles-binding reagents in an organelles-capture composition can bind to can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number organelles that the organelles-binding reagents in an organelles-capture composition can bind to can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The number of different organelles removed or depleted can be different in different embodiments. In some embodiments, the number of different organelles removed or depleted can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of different organelles removed or depleted can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

The number of molecules of an organelle removed or depleted can be different in different embodiments. In some embodiments, the number of molecules of an organelle removed or depleted can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of molecules of an organelle removed or depleted can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000.

In some embodiments, the second epitope can comprise biotin, hapten, or a combination thereof. The hapten can comprise digoxigenin, 2,4-dinitrophenol, fluorescein, or a combination thereof. The reagent capable of specifically binding to the organelles-binding reagent can comprise an anti-hapten antibody. The reagent capable of specifically binding to the organelles-binding reagent can comprise avidin, streptavidin, neutravidin, or a combination thereof. In some embodiments, second epitope and/or second epitope-binding reagent can be an affinity moiety such as biotin, streptavidin, heparin, an aptamer, a click-chemistry moiety, digoxigenin, primary amine(s), carboxyl(s), hydroxyl(s), aldehyde(s), ketone(s), or any combination thereof. The second epitope and second epitope-binding reagent can be members of a binding pair, for example, biotin/streptavidin. The organelles-binding reagent can comprise a primary antibody capable of specifically binding to the one or more components of the one or more organelles of the plurality of cells, and the reagent capable of specifically binding to the organelles-binding reagent can comprise a secondary antibody capable of specifically binding to the primary antibody.

In some embodiments, the organelles-binding reagent can comprise an organelle surface component-binding reagent, the one or more components of the one or more organelles can comprise one or more organelle surface components, and the organelles-binding reagent can be capable of specifically binding to the one or more organelle surface components.

Organelles-Capture Particles

In some embodiments, the reagent capable of specifically binding to the organelles-binding reagent (e.g., second epitope binding reagent) is associated with an organelles-capture particle (e.g., a particle 548 with a surface illustrated in FIGS. 5A-5B). The reagent capable of specifically binding to the organelles-binding reagent can be immobilized, or partially immobilized, on the organelles-capture particle. For example, the reagent capable of specifically binding to the organelles-binding reagent can be reversibly, non-reversibly, covalently, non-covalently, or a combination thereof, associated with the organelles-capture particle e. As another example, the reagent capable of specifically binding to the organelles-binding reagent can embedded, partially embedded, non-embedded, enclosed, partially enclosed, non-enclosed, or a combination thereof, in the organelles-capture particle.

In some embodiments, the organelles-capture particle comprises an organelles-capture bead. The organelles-capture particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The organelles-capture particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof.

In some embodiments, depleting the organelles of the plurality of cells using the organelles-capture composition can comprise: depleting the one or more organelles-capture particles by magnetic removal, centrifugation, or any combination thereof. The organelles can comprise mitochondria of the plurality of cells. The one or more components of the one or more organelles of the plurality of cells can comprise: ABCD3, ESR2, NOS3, ALB, HIF1A, NR3C1, ATP5A1, HK1, PGR, CASQ1, HSPA1A, PHB, CLTC, HSPD1, PLN, COX4I1, IFM1, SOD1, CPS1, LGALS3, TP53, Cytochrome C Oxidase, MAPT, TP5B, ERN1, MT-CO1, VDAC1, or a combination thereof.

Organelles Removal Composition

In some embodiments, the composition comprises an organelles-capture composition comprising an organelles-binding reagent, wherein the organelles-binding reagent is capable of specifically binding to one or more components of one or more organelles. The composition can comprise a reagent capable of specifically binding to the organelles-binding reagent. The organelles-binding reagent can be associated with a second epitope, and the reagent capable of specifically binding to the organelles-binding reagent can comprise a second epitope-binding reagent. In some embodiments, the reagent capable of specifically binding to the organelles-binding reagent is associated with an organelles-capture particle. In some embodiments, the organelles-binding reagent comprises an organelle surface component-binding reagent, the one or more components of the one or more organelles can comprise one or more organelle surface components, and the organelles-binding reagent can be capable of specifically binding to the one or more organelle surface components.

Sequencing

In some embodiments, estimating the number of different barcoded targets (e.g., stochastically barcoded targets) can comprise determining the sequences of the labeled targets, the spatial label, the molecular label, the sample label, the cell label, or any product thereof (e.g. labeled-amplicons, or labeled-cDNA molecules). An amplified target can be subjected to sequencing. Determining the sequence of a barcoded target (e.g., a stochastically barcoded target) or any product thereof can comprise conducting a sequencing reaction to determine the sequence of at least a portion of a sample label, a spatial label, a cell label, a molecular label, at least a portion of the labeled target (e.g., stochastically labeled target), a complement thereof, a reverse complement thereof, or any combination thereof.

Determination of the sequence of a barcoded target or a stochastically barcoded target (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the barcoded target (e.g., stochastically barcoded target) or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the barcoded target or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can be utilized. In some embodiments, sequencing can comprise MiSeq sequencing. In some embodiments, sequencing can comprise HiSeq sequencing.

The labeled targets (e.g., stochastically labeled targets) can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the barcoded targets comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly(T) tail by capturing the mRNAs from the sample.

Determining the sequences of the spatial labels and the molecular labels of the plurality of the barcodes (e.g., stochastic barcodes) can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or a number or a range between any two of these values, of the plurality of barcodes. Determining the sequences of the labels of the plurality of barcodes, for example the sample labels, the spatial labels, and the molecular labels, can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or a number or a range between any two of these values, of the plurality of barcodes. Sequencing some or all of the plurality of barcodes can include generating sequences with read lengths of, of about, of at least, or of at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, of nucleotides or bases.

Sequencing can comprise sequencing at least, or at least about, 10, 20, 30, 40, 50, 60, 70, 80, 90, 100, or more nucleotides or base pairs of the barcoded targets. For example, sequencing can comprise generating sequencing data with sequences with read lengths of 50, 75, or 100, or more nucleotides by performing polymerase chain reaction (PCR) amplification on the plurality of barcoded targets. Sequencing can comprise sequencing at least, or at least about, 200, 300, 400, 500, 600, 700, 800, 900, 1,000, or more nucleotides or base pairs of the barcoded targets. Sequencing can comprise sequencing at least, or at least about, 1500, 2000, 3000, 4000, 5000, 6000, 7000, 8000, 9000, or 10000, or more nucleotides or base pairs of the barcoded targets.

Sequencing can comprise at least about 200, 300, 400, 500, 600, 700, 800, 900, 1,000, or more sequencing reads per run. In some embodiments, sequencing comprises sequencing at least, or at least about, 1500, 2000, 3000, 4000, 5000, 6000, 7000, 8000, 9000, or 10000, or more sequencing reads per run. Sequencing can comprise less than or equal to about 1,600,000,000 sequencing reads per run. Sequencing can comprise less than or equal to about 200,000,000 reads per run.

Samples

In some embodiments, the plurality of targets can be comprised in one or more samples. A sample can comprise one or more cells, or nucleic acids from one or more cells. A sample can be a single cell or nucleic acids from a single cell. The one or more cells can be of one or more cell types. At least one of the one or more cell types can be brain cell, heart cell, cancer cell, circulating tumor cell, organ cell, epithelial cell, metastatic cell, benign cell, primary cell, circulatory cell, or any combination thereof.

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus such as single-stranded (+ strand or "sense") DNA viruses (e.g. parvoviruses), or double-stranded RNA viruses (e.g. reoviruses). In some embodiments, the cells are bacteria. These can include either gram-positive or gram-negative bacteria. In some embodiments, the cells are fungi. In some embodiments, the cells are protozoans or other parasites.

As used herein, the term "cell" can refer to one or more cells. In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Methods of Removing Undesirable Nucleic Acid Species

Single cell analysis, such as single cell whole transcriptome analysis (WTA), can be hindered by the presence or high abundance of targets or target species not of interest (such as nucleic acid or nucleic acid species not of interest, also referred to herein as undesirable or unwanted nucleic acid or nucleic acid species). In many samples nucleic acids derived from non-nuclear organelles (e.g., mitochondrial mRNA and ribosomal RNA) can be present in high abundance and/or undesirable. For example, for a heterogeneous cDNA sample, PCR is usually performed in excess cycles to adequately amplify low expressers; in those scenarios, the native gene expression profile is usually skewed by the dominating high expresser PCR products. A method to correct for such bias in PCR product is Molecular Indexing;

however, high expressers such as mitochondrial mRNAs often dominate the sequencing run with little contribution to the experimental interpretation, rendering the sequencing cost for Molecular Index counting to be expensive. Previous efforts to increase the relative abundance of low abundance species in a nucleic acid sample have included library normalization methods. Some embodiments disclosed herein provide methods of removing undesirable nucleic acid species (e.g., nucleic acids derived from non-nuclear organelles, mtRNA, rRNA) from the plurality of nucleic acid molecules.

In some embodiments, the methods disclosed herein comprise providing a sample comprising a plurality of nucleic acid target molecules. The sample can, in some embodiments, comprise one or more undesirable nucleic acid species. It would be appreciated by one of skill in the art that the plurality of nucleic acid target molecules and/or the undesirable nucleic acid species can comprise a variety of nucleic acid target molecules. For example, the nucleic acid target molecules and/or the undesirable nucleic acid species can comprise DNA molecules, RNA molecules, genomic DNA molecules, cDNA molecules, mRNA molecules, rRNA molecules, mtDNA, siRNA molecules, or any combination thereof. The nucleic acid target molecule can be double-stranded or single-stranded. In some embodiments, the plurality of nucleic acid target molecules can comprise nucleic acids derived from one or more non-nuclear organelles. In some embodiments, the plurality of nucleic acid target molecules can comprise polyA RNA molecules. In some embodiments, the plurality of nucleic acid target molecules comprise at least 100, at least 1,000, at least 10,000, at least 20,000, at least 30,000, at least 40,000, at least 50,000, at least 100,000, at least 1,000,000, or more nucleic acid species.

The sample can, for example, comprise a plurality of nucleic acid target molecules, and one or more undesirable nucleic acid species (e.g., nucleic acids derived from non-nuclear organelles). The one or more undesirable nucleic acid species can be present in the sample in different amount. For example, the one or more undesirable nucleic acid species can amount to about, or at least about, 5%, 10%, 15%, 20%, 25%, 30%, 35%, 40%, 45%, 50%, 55%, 60%, 65%, 70%, 75%, 80%, 85%, 90%, 95%, 98%, 99%, or more, or 100%, or a range between two of these values, of the nucleic acid content of the sample. In some embodiments, the one or more undesirable nucleic acid species amounts to at least about 10% of the nucleic acid content of the sample. In some embodiments, the one or more undesirable nucleic acid species amounts to at least about 30% of the nucleic acid content of the sample. In some embodiments, the one or more undesirable nucleic acid species amounts to at least about 50% of the nucleic acid content of the sample. The undesirable nucleic acid species can be, or can comprise, various type(s) of nucleic acid molecules. For example, at least one of the one or more undesirable nucleic acid species can be ribosomal protein mRNA, mitochondrial mRNA, genomic DNA, intronic sequence, high abundance sequence, or a combination thereof. In some embodiments, the undesirable nucleic acid species is, or comprise, mRNA species. The mRNA species can be, for example, one or more of mRNA species of housekeeping genes, mRNA species of ribosomal genes, mRNA species of mitochondrial genes, mRNA species of high abundance genes, or any combination thereof. In some embodiments, the undesirable nucleic acid species is, or comprise, DNA species. The DNA species can be, for example, one or more of DNA species of housekeeping genes, DNA species of ribosomal genes, DNA species of mitochondrial genes, DNA species of high abundance genes, or any combination thereof. In some embodiments, the undesirable nucleic acid species is, or comprise, DNA species and RNA species.

In some embodiments, the nuclei isolation and/or organelle depletion methods described herein can significantly reduce the abundance of the one or more undesirable nucleic acid species (e.g., nucleic acids derived from non-nuclear organelles) as compared to the plurality of nucleic acid target molecules in the sample. In some embodiments, the methods and compositions disclosed herein can reduce the abundance of one or more undesirable nucleic acid species in a sample. For example, the methods and compositions disclosed herein can reduce the abundance of at least 1, at least 2, at least 3, at least 4, at least 5, at least 10, at least 20, at least 50, at least 100, at least 200, at least 500, at least 1,000, or more, undesirable nucleic acid species in the sample. In some embodiments, the methods and compositions disclosed herein can reduce the abundance by at least 10%, at least 20%, at least 30%, at least 40%, at least 50%, at least 60%, at least 70%, at least 80%, at least 90%, at least 95%, at least 99%, or 100% of each of the one or more undesirable nucleic acid species in the sample. In some embodiments, the abundance of the one or more undesirable nucleic acid species can be reduced by at least 10%, at least 20%, at least 30%, at least 40%, at least 55%, at least 50%, at least 65%, at least 60%, at least 65%, at least 70%, at least 75%, at least 80%, at least 85%, at least 90%, at least 95%, at least 99%, or more, or a range between any two of these values, in comparison to the abundance of at least one of the nucleic acid target molecules in the starting sample prior to organelle depletion and/or nuclei isolation as described herein.

It would be appreciated that in some embodiments, the methods and compositions disclosed herein may reduce the abundance of undesirable nucleic acid species without significantly reducing the number of different molecular label sequences associated with the other nucleic acid target molecules. For example, the methods and compositions disclosed herein can reduce the abundance of undesirable nucleic acid species while retaining at least at least 10%, at least 20%, at least 30%, at least 40%, at least 50%, at least 60%, at least 70%, at least 80%, at least 90%, at least 95%, or 100% of the different molecular label sequences associated with the other nucleic acid target molecules. In some embodiments, the methods and compositions disclosed herein can reduce the abundance of undesirable nucleic acid species by at least at least 10%, at least 20%, at least 30%, at least 40%, at least 50%, at least 60%, at least 70%, at least 80%, at least 90%, at least 95%, or at least 99% while retaining at least at least 10%, at least 20%, at least 30%, at least 40%, at least 50%, at least 60%, at least 70%, at least 80%, at least 90%, at least 95%, or 100% of the different molecular label sequences associated with the other nucleic acid target molecules. In some embodiments, reducing the abundance of undesirable nucleic acid species does not significantly reduce the number of different molecular label sequences associated with the other nucleic acid target molecules.

In some embodiments, after using the nuclei isolation and/or organelle depletion methods described herein, the sequencing reads for the undesirable nucleic acid species are less than 50%, less than 40%, less than 30%, less than 20%, less than 10%, less than 5%, or less, of the total sequencing reads. In some embodiments, the sequencing reads for the undesirable nucleic acid species are less than 40% of the total sequencing reads. In some embodiments, the sequencing reads for the undesirable nucleic acid species are less than 30% of the total sequencing reads. In some embodiments, the sequencing reads for the undesirable nucleic acid species are less than 20% of the total sequencing reads. In some embodiments, the sequencing reads for the undesirable nucleic acid species are less than 10% of the total sequencing reads. In some embodiments, after using the nuclei isolation and/or organelle depletion methods described herein, the sequencing reads for the undesirable nucleic acid species are reduced to less than 60%, less than 50%, less than 40%, less than 30%, less than 20%, less than 10%, less than 5% of the sequencing reads for the undesirable nucleic acid without using the nuclei isolation and/or organelle depletion methods described herein. In some embodiments, after using the nuclei isolation and/or organelle depletion methods described herein, the sequencing reads for the undesirable nucleic acid species are reduced to, or to about, 60%, 50%, 40%, 30%, 20%, 10%, 5%, 2%, 1%, 0.5%, or a range between any two of these values, of the sequencing reads for the undesirable nucleic acid without using the nuclei isolation and/or organelle depletion methods described herein.

In some embodiments, the methods and compositions disclosed herein can improve sequencing efficiency by decreasing the sequencing reads:molecular label ratio of an undesirable nucleic acid species and/or increasing the sequencing reads:molecular label ratio of a nucleic acid target molecule. For example, the ratio of sequencing reads to molecular label for an undesirable nucleic acid species can be less than 20, less than 15, less than 10, less than 9, less than 8, less than 7, less than 6, less than 5, less than 4, less than 3, less than 2, or less than 1. In some embodiments, the ratio of sequencing reads to molecular label for an undesirable nucleic acid species is 20, 15, 10, 9, 8, 7, 6, 5, 4, 3, 2, 1, or a range between any two of these values.

EXAMPLES

Some aspects of the embodiments discussed above are disclosed in further detail in the following examples, which are not in any way intended to limit the scope of the present disclosure.

Example 1

Nuclei Capture and Barcoding Workflow

This example demonstrates a workflow for nuclei capture and barcoding. FIGS. 6A-6F is a schematic illustration of a non-limiting exemplary workflow for nuclei isolation and single cell profiling. The workflow can comprise cell lysis (e.g., using a light lysis buffer to lyse the plasma membrane without lysing the nuclear membrane and/or one or more organelles). The workflow can include the selective depletion of one or more organelles (e.g., mitochondria). The workflow can include associating each nuclei with a nuclei indexing oligonucleotide comprising a nuclei indexing sequence (e.g., for sample indexing). The workflow can include isolating nuclei from one or more cellular components. The workflow can include partitioning individual nuclei to partitions and conducting nucleus lysis. The workflow can include barcoding (e.g., stochastic barcoding) of target nucleic acid molecules and/or nuclei indexing oligonucleotides for single cell analysis (e.g., Rhapsody™ assay (Becton, Dickinson and Company (Franklin Lakes, NJ)), ChromiumM Single Cell 3' Solution (10× Genomics (San Francisco, CA))).

Sample Composition

Sample 601 can comprise a plurality of cells 602. A sample for use in the method of the disclosure can one for which it is technically difficult or impossible to generate a single-cell suspension (e.g., frozen cells, fixed cells, tissue specimens, tumor specimens, epithelial tissues, formalin-fixed paraffin-embedded cells, and combinations thereof). A cell can comprise a plasma membrane 604 and a cell nucleus 606. The cell nucleus can comprise a nuclear envelope 608 and one or more nucleic acid target molecules 612. The nuclear envelope can comprise one or more nuclear envelope surface components 610, such as a nuclear envelope protein (e.g., a lamin). The nucleus can include one or more target nucleic acid molecules (e.g., messenger RNA (mRNA), microRNA (miRNA), long non-coding RNA (long ncRNA or lncRNA), Piwi-interacting RNA (piRNA)). The cell can comprise one or more organelles (e.g., ribosomes, mitochondria) as described herein, and the one or more organelles can comprise one or more organelle surface components. Mitochondria 616 can comprise an organelle surface component (e.g., mitochondrial surface component 618). The cell can also comprise extranuclear cellular components 614. Extranuclear cellular components can, for example, comprise undesired extranuclear cytoplasmic components (e.g., molecules that are unnecessary and/or detrimental to single cell expression profiling). Extranuclear cellular components can include cytoplasmic fragments. Extranuclear cellular components can include organelles. Extranuclear cellular components can include mitochondria. Extranuclear cellular components can include ribosomes. Extranuclear cellular components can include rough endoplasmic reticuli. Extranuclear cellular components can comprise one or more undesired nucleic acids (e.g., ribosomal RNA, mitochondrial DNA, mitochondrial RNA). Extranuclear cellular components can comprise one or more macromolecules that would interfere with the single cell expression analysis methods disclosed herein. Extranuclear cellular components 614 can, for example, comprise mitochondria, peroxisomes, cytosol, vesicles, lysosomes, plasma membranes, chloroplasts, inner mitochondrial matrices, inner mitochondrial membranes, intermembrane spaces, outer mitochondrial membranes, secretory vesicles, smooth endoplasmic reticuli, rough endoplasmic reticuli, golgi bodies, phagosomes, endosomes, exosomes, plasma membranes, microtubules, microfilaments, intermediate filaments, filopodia, ruffles, lamellipodia, sarcomeres, focal contacts, podosomes, ribosomes, microsomes, lipid rafts, cell walls, and combinations thereof.

Plasma Membrane Lysis

Figure 6A:
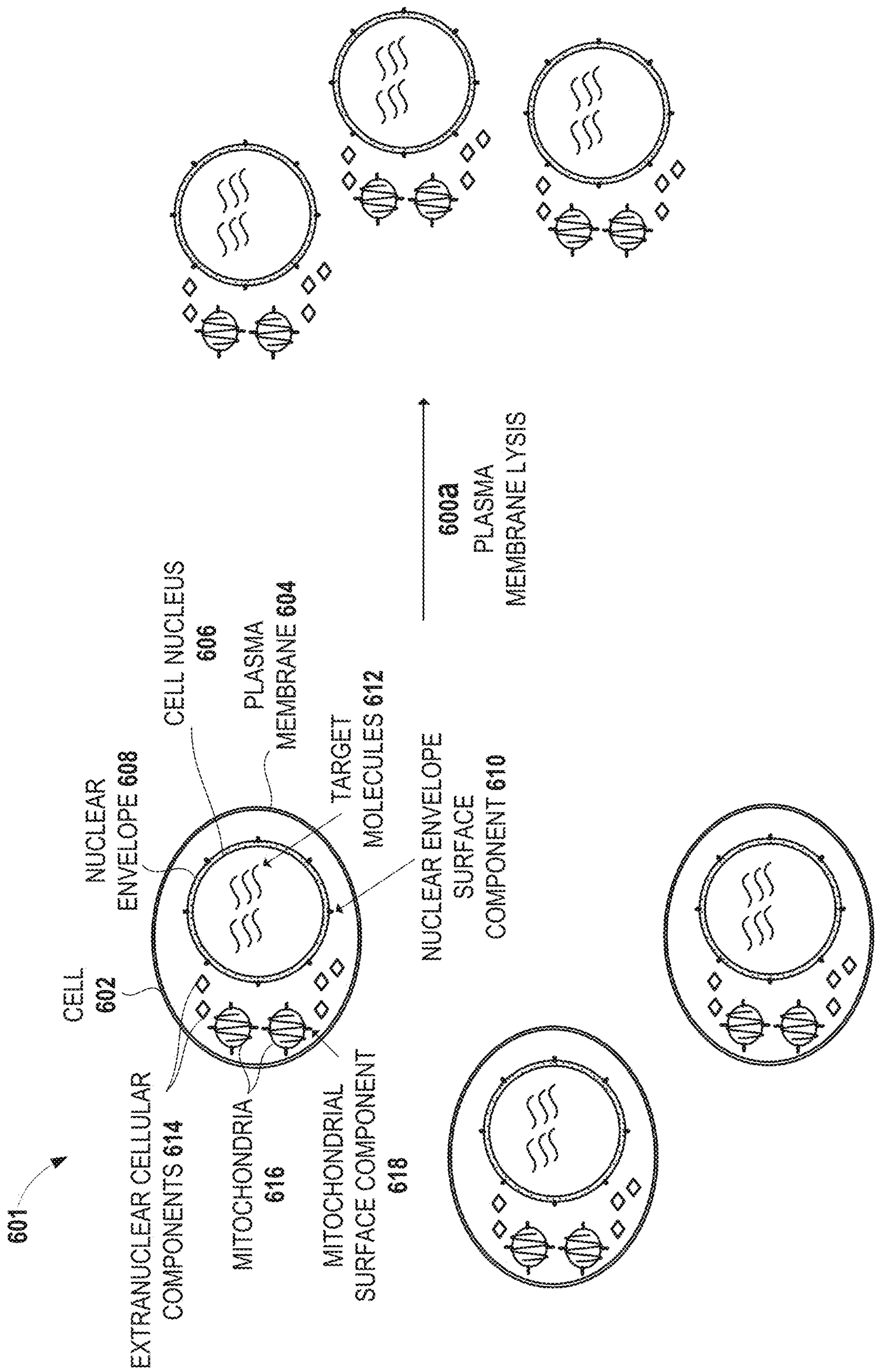
FIGS. 6A-6F show a non-limiting exemplary schematic illustration of a nuclei capture and barcoding workflow.

The workflow can comprise plasma membrane lysis (step 600*a*) of the population of cells 602 of sample 601. Plasma membrane lysis can generate a lysate comprising plurality of a population of nuclei, organelles, and extranuclear cellular components (e.g., ribosomes) as depicted in FIG. 6A. The method can comprise lysing the plurality of cells without lysing the nuclear envelope. The method can comprise lysing the plurality of cells without lysing organelle membranes. The method can comprise lysing the plurality of cells and lysing organelle membranes without lysing the nuclear envelope. Plasma membrane lysis can be performed using a homogenizer (e.g., a Dounce homogenizer), a detergent, or an enzymatic method.

Contacting with Organelle Surface Component Binding Reagent(s)

Figure 6B:
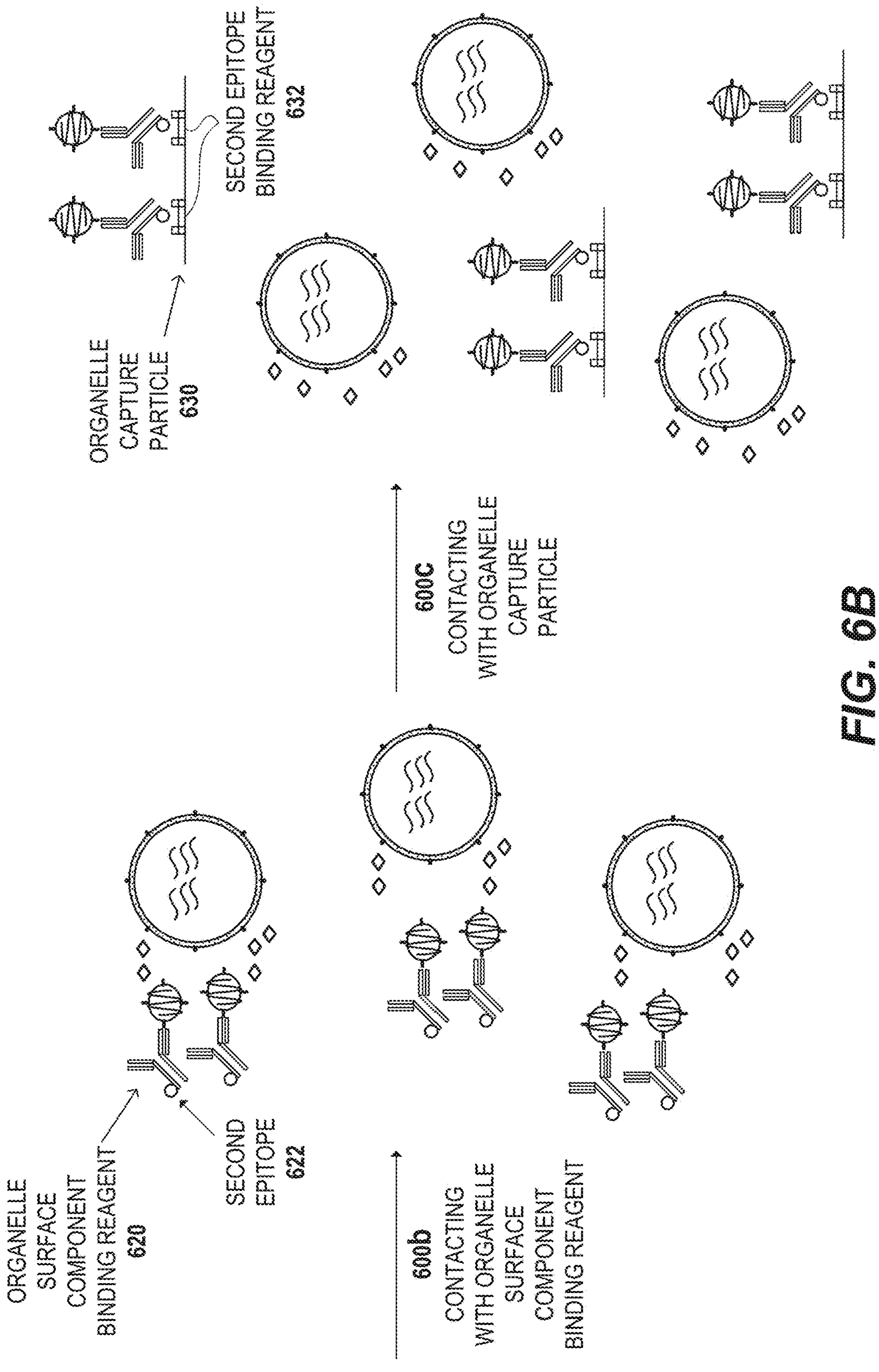

The workflow can comprise contacting the lysate with one or more organelle surface component binding reagents (step 600*b*). A second epitope 622 can be associated (e.g., immobilized, partially immobilized, enclosed, partially enclosed) with the organelle surface component binding reagent 620 (e.g., organelles-binding reagent). The second epitope 622 can comprise a strong epitope (e.g, biotin, fluorescein, and/or DIG) as described herein. The organelle surface component binding reagent 620 can be capable of specifically binding to one or more components of one or more organelles (e.g., mitochondria) such as, for example mitochondrial surface component 618 (as depicted in FIG. 6B). Contacting the one or more organelles of the plurality of cells with the organelle surface component binding reagent can generate one or more organelles bound to the organelle component-binding reagent. The organelle surface component binding reagent 620 can comprise a mitochondria-specific antibody (or another mitochondria-specific binding reagent).

Contacting with Organelle Capture Particles

The workflow can comprise contacting the lysate with one or more organelle capture particles (step 600*c*). The organelle capture particle 630 can comprise a reagent capable of specifically binding to the organelles-binding reagent (e.g., a second epitope binding reagent 632 as depicted in FIG. 6B) as described herein. The second epitope binding reagent 632 can be associated (e.g., immobilized, partially immobilized, enclosed, partially enclosed) with the organelle capture particle 630. In some embodiments, the organelle surface component binding reagent 620 does not comprise a second epitope. In some such embodiments, the organelle surface component binding reagent can comprise a primary antibody capable of specifically binding to one or more components of one or more organelles (e.g., mitochondria) and the reagent capable of specifically binding to the organelles-binding reagent comprises a secondary antibody capable of specifically binding to the primary antibody. Step 600*c* can generate one or more organelles bound to the organelle capture particles via the organelle surface component binding reagent.

Removal of Organelle Capture Particles

The workflow can comprise removal of organelle capture particles (step 600*d*). Removal of the organelle capture particles can occur by magnetic removal, centrifugation, filtration, or any combination thereof. Step 600*d* can generate a lysate depleted of one or more organelles.

Contacting with Nuclei BindingReagent(s)

Figure 6C:
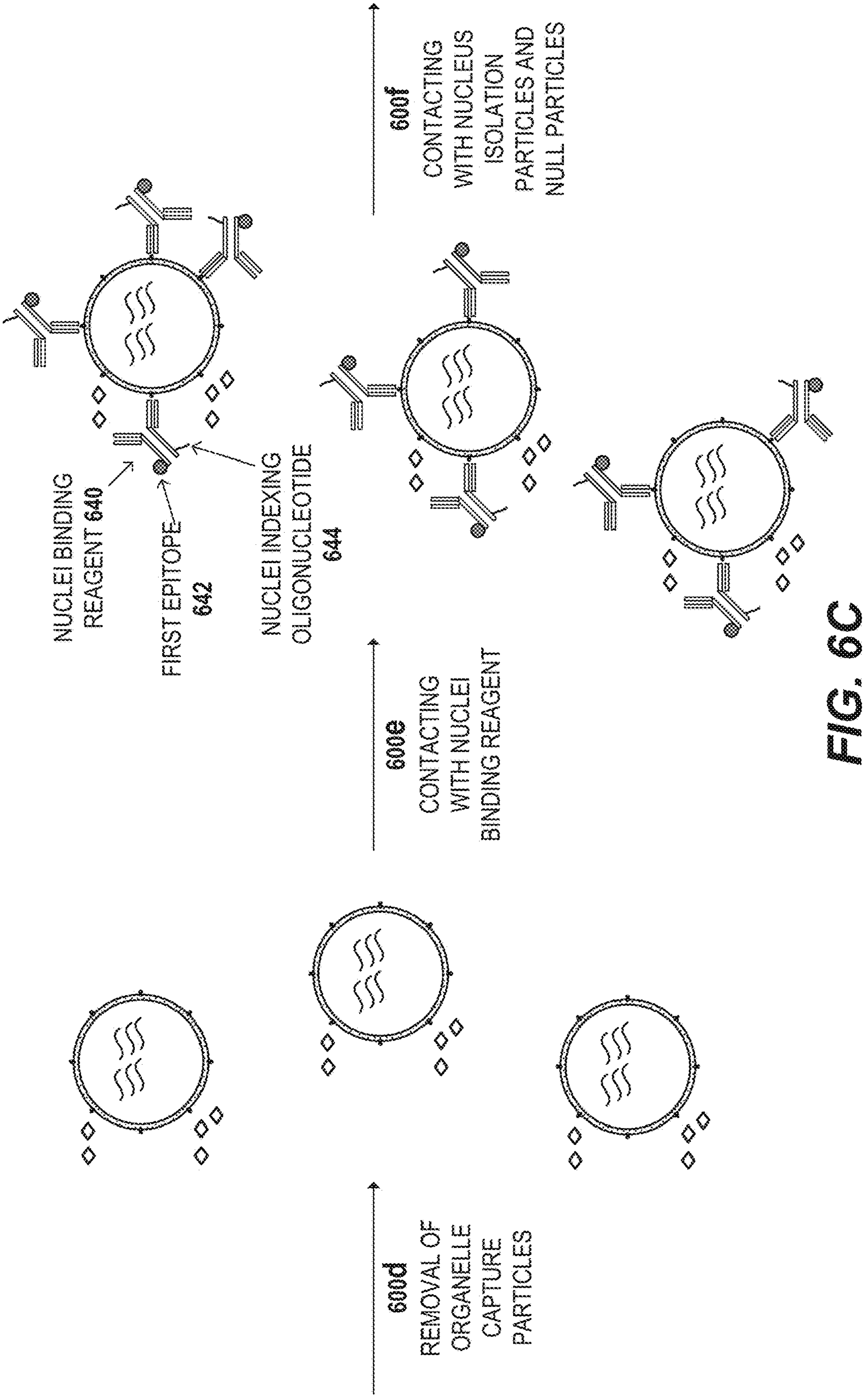

The workflow can comprise contacting the lysate with one or more nuclei binding reagents (step 600*e*). Nuclei binding reagent 640 can comprise a first epitope 642. The first epitope 642 can, for example, comprise a strong epitope (e.g., biotin, fluorescein, and/or DIG) as described herein. The nuclei binding reagent 640 can be capable of specifically binding to one or more components of the nuclei (e.g., nuclear envelope proteins) such as, for example nuclear envelope surface components 610 (as depicted in FIG. 6C). In some embodiments, the nuclei-binding reagent comprises a carbohydrate-binding reagent (e.g., a carbohydrate-binding protein, a lectin). Contacting the nuclei with the nuclei binding reagent can generate nuclei bound to the nuclei-binding reagent. The nuclei binding reagent 640 can comprise nuclei indexing oligonucleotide 644. The nuclei indexing oligonucleotide 644 can comprise a nuclei indexing sequence (e.g., for sample indexing). The nuclei indexing oligonucleotide 644 can remain associated with the nuclei throughout the entire workflow. In some embodiments, the workflow can comprise pooling nuclei from different samples once nuclei are bound by a nuclei binding reagent comprising a nuclei indexing oligonucleotide.

Contacting with Nucleus Isolation Particles and Null Particles

Figure 6D:
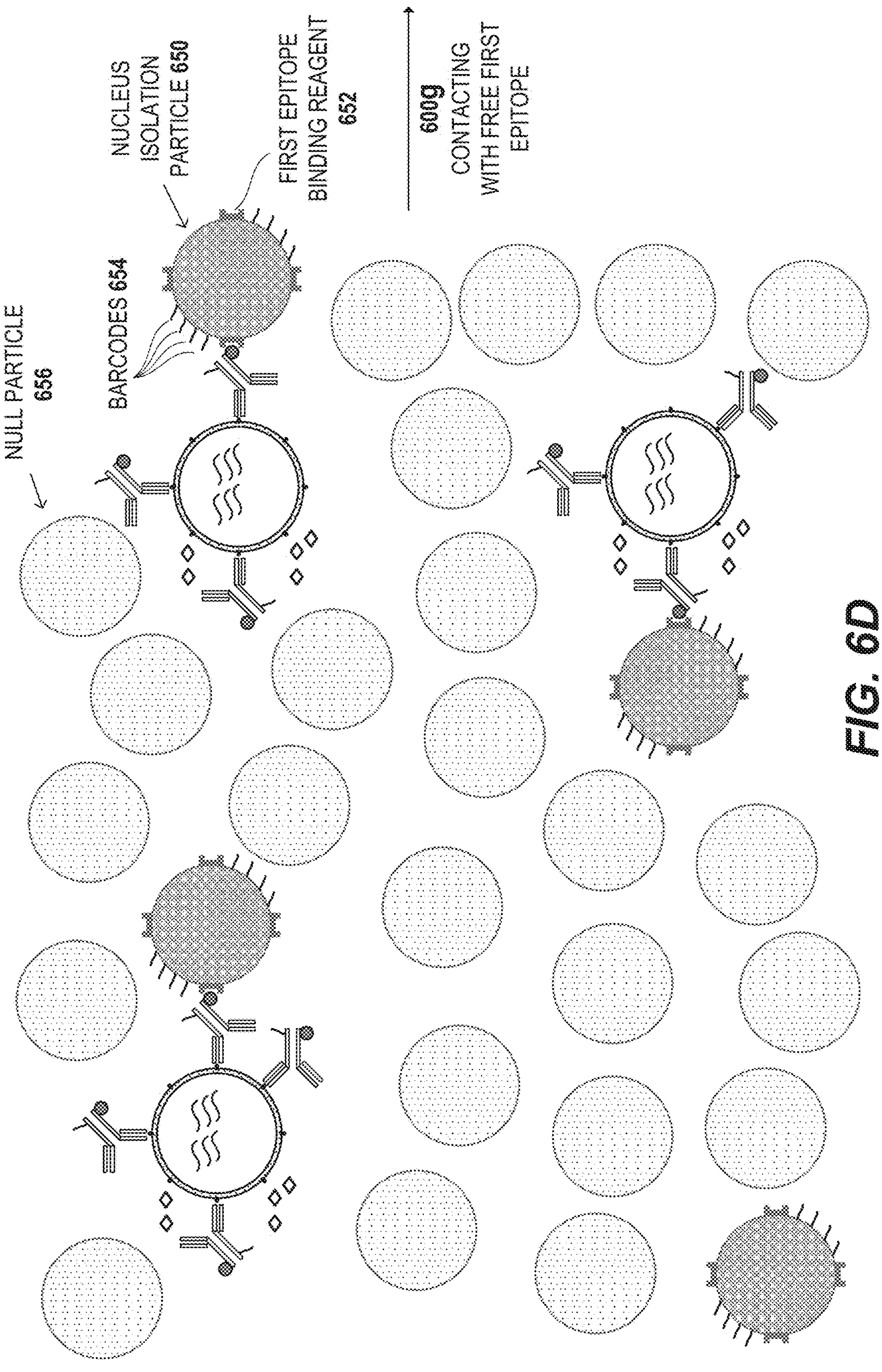

The workflow can comprise contacting the lysate with nucleus isolation particles and null particles (step 600*f*). The nucleus isolation particle 650 can comprise a reagent capable of specifically binding to the nuclei binding reagent (e.g., a first epitope binding reagent 652 as depicted in FIG. 6D) as described herein. The first epitope binding reagent 652 can be associated with (e.g., immobilized, partially immobilized, enclosed, partially enclosed) the nucleus-isolation particle. The nuclei-binding reagent can comprise a primary antibody capable of specifically binding to the one or more components of the nucleus, and the reagent capable of specifically binding to the nuclei binding reagent can comprise a secondary antibody capable of specifically binding to the primary antibody. A plurality of barcodes 654 can be associated (e.g., immobilized, partially immobilized, enclosed, partially enclosed) with the nucleus-isolation particle.

As depicted in FIG. 6D, step 600*f* can generate nuclei bound to nucleus isolation particles via the reagent capable of specifically binding to the nuclei binding reagent. In some embodiments, a population of nuclei within a sample can be separated from extranuclear cellular components according to the methods provided herein. In some embodiments, a population of nuclei within a sample can be individually separated from each other (e.g., isolated) according to the methods provided herein. Some embodiments of the compositions and methods disclosed herein can be optionally used to reduce or eliminate the clumping of nucleus isolation particles. Some embodiments of the methods and compositions provided herein can be used to, for example, (1) reduce or eliminate the binding of an individual nucleus isolation particle to two or more nuclei and/or (2) reduce or eliminate the binding of an individual nuclei to multiple nucleus isolation particles.

In some embodiments, the percentage of nucleus isolation particles bound to a single nuclei or no nuclei after contacting can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of nucleus isolation particles bound to a single nuclei or no nuclei after contacting can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the percentage of nuclei bound to a single nucleus isolation particle after contacting can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of nuclei bound to a single nucleus isolation particle after contacting can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9% 10%, 11%, 2%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the binding single nuclei to nucleus isolation particles can follow a Poisson distribution. In some embodiments, the binding single nuclei to nucleus isolation particles can follow a non-Poisson distribution. The probability that two distinct nuclei of a sample can be bound to the same nucleus isolation particle can be, or be at least, $10^{-6}$, $10^{-5}$, $10^{-4}$, $10^{-3}$, $10^{-2}$, or $10^{-1}$ or more. The probability that two distinct nuclei of a sample can be bound to the same nucleus isolation particle can be at most $10^{-6}$, $10^{-5}$, $10^{-4}$, $10^{-3}$, $10^{-2}$, or $10^{-1}$ or more. The probability that a single nuclei can be simultaneously bound to two or more distinct nucleus isolation particles can be, or be at least, $10^{-6}$, $10^{-5}$, $10^{-4}$, $10^{-3}$, $10^{-2}$, or $10^{-1}$ or more. The probability that a single nuclei can be simultaneously bound to two or more distinct nucleus isolation particles can be at most $10^{-6}$, $10^{-5}$, $10^{-4}$, $10^{-3}$, $10^{-2}$, or $10^{-1}$ or more.

In some embodiments the workflow comprises contacting the lysate with nucleus isolation particles 650 and null particles 656. In some embodiments, the null particles 656 do not comprise a plurality of barcodes, a magnetic property, and/or a reagent capable of specifically binding to the nuclei binding reagent (e.g., a first epitope binding reagent). The null particles can resemble the nucleus isolation particles in all aspects other than the absence of a plurality of barcodes, a magnetic property, and/or a reagent capable of specifically binding to the nuclei binding reagent (e.g., a first epitope binding reagent). In some embodiments, the lysate is contacted with null particles prior to contacting with nucleus isolation particles. In some embodiments, the lysate is contacted with null particles and nucleus isolation particles simultaneously. Contacting with null particles can (1) reduce or eliminate the binding of an individual nucleus isolation particle to two or more nuclei and/or (2) reduce or eliminate the binding of an individual nuclei to multiple nucleus isolation particles.

In some embodiments, the ratio of the nucleus isolation particles to null particles ranges from 1:100 to 100:1. In some embodiments, the ratio of the nucleus isolation particles to null particles is at most 10:1. In some embodiments, the ratio of the nucleus isolation particles to null particles is at most 100:1. In some embodiments, the ratio of the nucleus isolation particles to null particles is at most 1:1000. In some embodiments, the ratio of the nucleus isolation particles to null particles is at least 1:10. In some embodiments, the ratio of the nucleus isolation particles to null particles is at least 1:100. In some embodiments, the ratio of the nucleus isolation particles to null particles is at least 1:1000.

In some embodiments, the ratio of the nucleus isolation particles to null particles can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio of the nucleus isolation particles to null particles can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

Some embodiments of the methods and compositions provided herein employ flow cytometry to (1) reduce or eliminate the binding of an individual nucleus isolation particle to two or more nuclei and/or (2) reduce or eliminate the binding of an individual nuclei to multiple nucleus isolation particles. For example, a series of droplets each comprising a single nuclei and a series of droplets each comprising a single nuclei can be merged to create a series of droplets each comprising a single nuclei and a single nucleus isolation particle. Following the binding of the single nuclei to the single nucleus isolation particle within a droplet, each droplet of the series of droplets can be merged with another series of droplets comprising free first epitope as described herein. After saturation of the first epitope binding sites on the nucleus isolation particle, the plurality of droplets can be pooled and subjected to the downstream methods of the disclosure.

Contacting with Free First Epitope

Figure 6E:
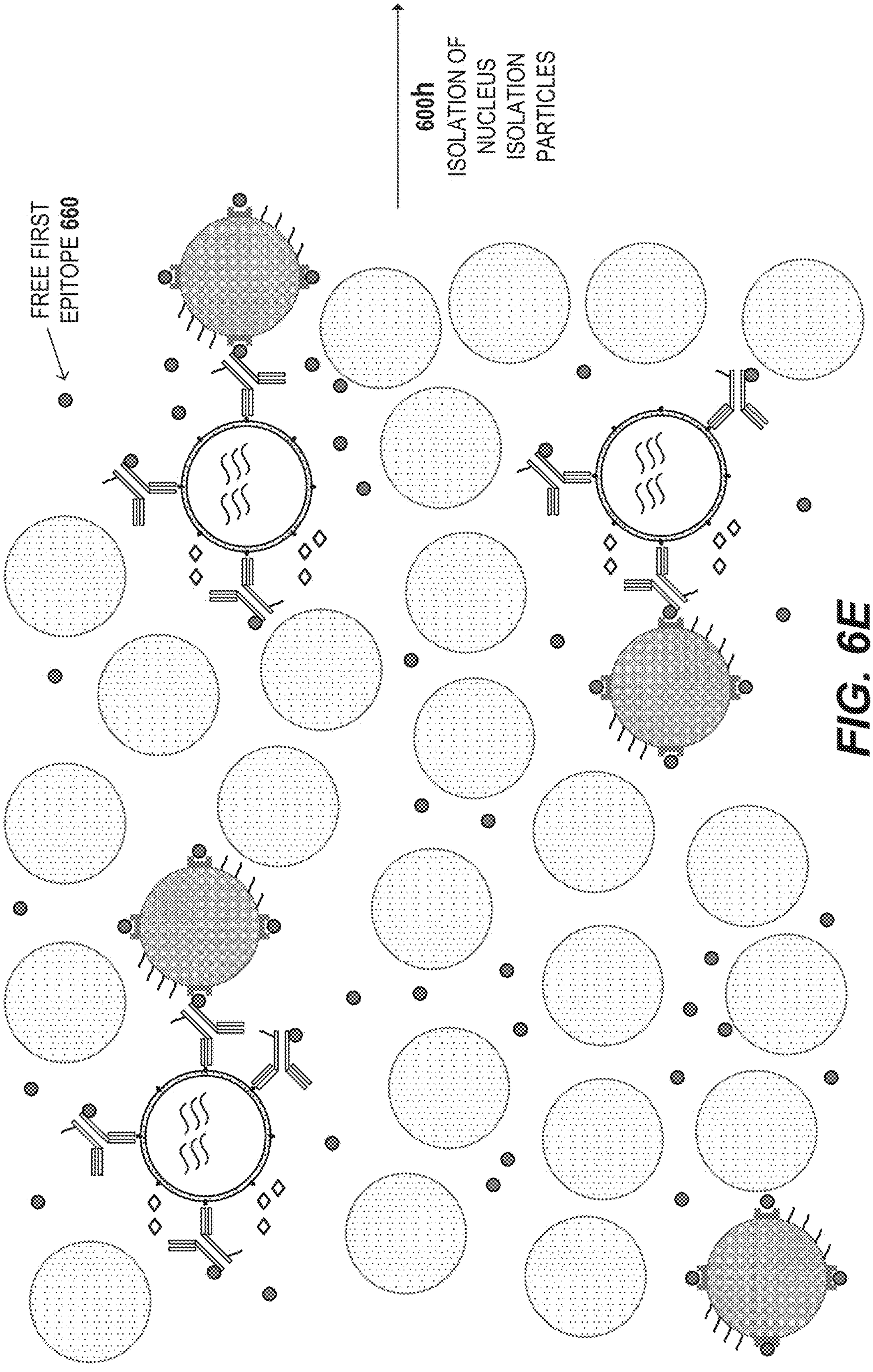
Figure 6F:
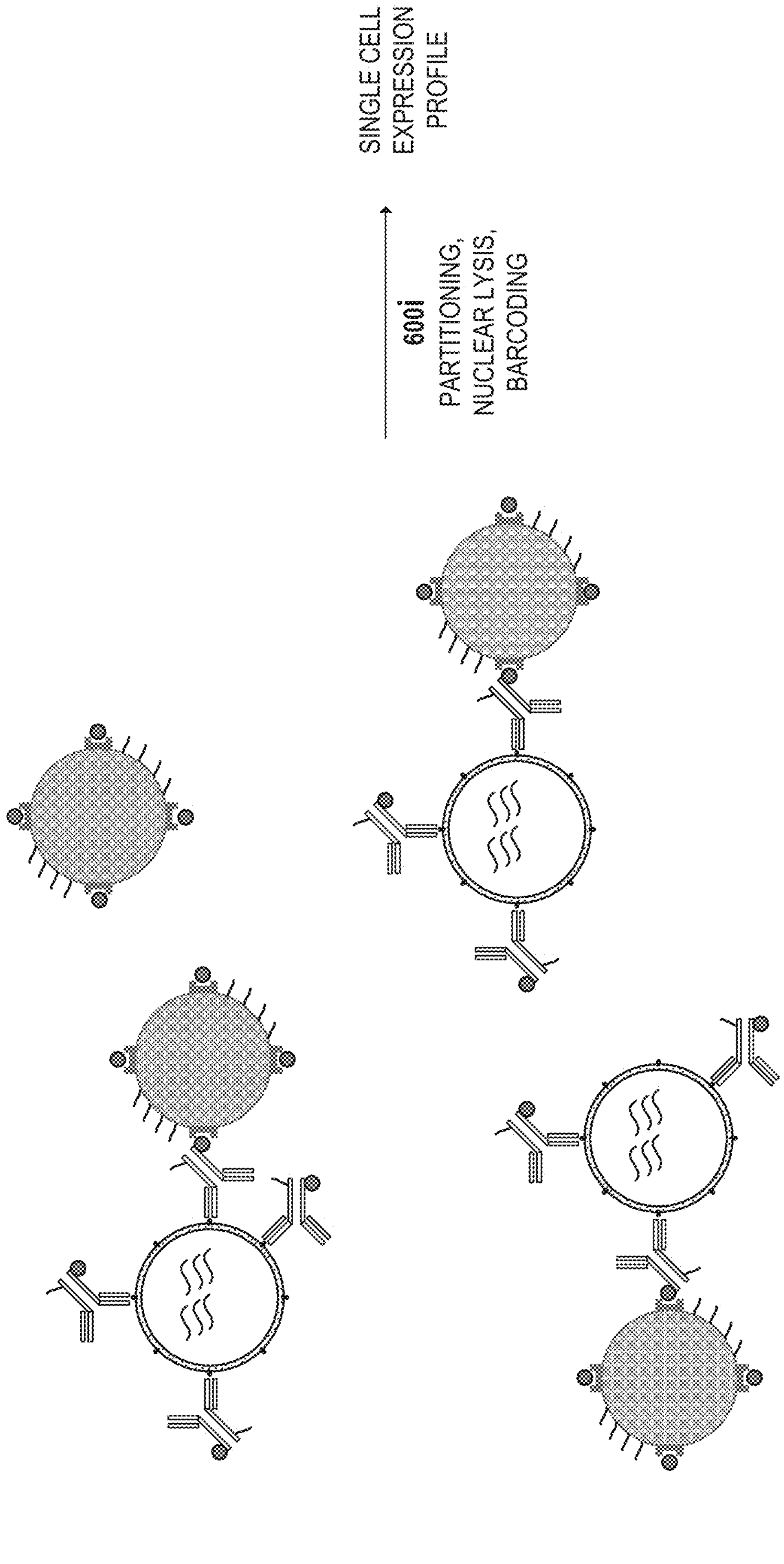

The workflow can comprise contacting the lysate with free first epitope (step 600*g*). The free first epitope 660 can comprise all or a portion of the first epitope 642. The free first epitope can bind unbound first epitope binding reagent (e.g., a first epitope binding reagent 652 as depicted in FIG. 6E) associated with nucleus isolation particles. Following step 600*g* most or all of the binding sites of the nuclei binding reagent can be saturated (e.g., either bound by a free first epitope or a first epitope of a nuclei binding reagent)

thereby reducing or preventing any additional binding of nucleus isolation particles to nuclei. Contacting with free first epitope can prevent clumping of nucleus isolation particles when separated from null particles downstream in the workflow.

In some embodiments, the ratio of free first epitope to nucleus isolation particles can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio of free first epitope to nucleus isolation particles can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the percentage of nucleus isolation particles comprising one or more unbound first epitope binding reagents after contacting with free first epitope can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of nucleus isolation particles comprising one or more unbound first epitope binding reagents after contacting with free first epitope can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Isolation of Nucleus Isolation Particles

The workflow can comprise isolation of nucleus isolation particles (step 600*h*). Isolation of nucleus isolation particles (and the nuclei bound thereto) can comprise isolating the nucleus-isolation particle by magnetic removal, filtration, centrifugation, or any combination thereof. Step 600*h* can generate a plurality of isolated nucleus isolation particles (each bound to one or zero nuclei) depleted of organelles and/or extranuclear cellular components.

Partitioning Nuclear Lysis, and Barcoding

The workflow can comprise partitioning, nuclear lysis, and barcoding (step 600*i*). The plurality of nuclei and the nucleus isolation particles bound thereto can partitioned to a plurality of partitions. In some embodiments, the plurality of nuclei are separated from the nucleus isolation particles prior to partitioning of said nuclei to a plurality of partitions. A partition can be a microwell, droplet, or emulsion. A partition of the plurality of partitions can comprise a single nuclei from the plurality of nuclei and its associated nucleus isolation particle. A partition of the plurality of partitions can comprise a single nuclei from the plurality of nuclei and a barcoding particle. A partition of the plurality of partitions can comprise a single nuclei from the plurality of nuclei, its associated nucleus isolation particle, and a barcoding particle. In some embodiments, the microwell dimensions (e.g., microwell depth) are chosen to optimize nuclei and nucleus isolation particle trapping efficiency while also providing efficient exchange of assay buffers and other reagents contained within the wells. Once partitioned, nuclei can be lysed according to the methods provided herein. Barcoding can comprise using the plurality of barcodes of a nucleus isolation particle and/or a barcoding particle to generate a plurality of barcoded nuclei indexing oligonucleotides and/or barcoded targets according to the methods provided herein. The products of Step 600*i* (e.g., barcoded nuclei indexing oligonucleotides and/or barcoded targets) can undergo the downstream methods provided herein to generate a single cell expression profile.

In some embodiments, one or more steps of the workflow comprise centrifugation. In some embodiments, one or more steps of the workflow do not comprise centrifugation. In some embodiments none of the steps of the workflow comprise centrifugation. In some embodiments, the workflow does not comprise one or more of step 600*a*, step 600*b*, step 600*c*, step 600*d*, step 600*e*, step 600*f*, step 600*g*, step 600*h*, and/or step 600*i*. For example, in some embodiments, the method does not comprise contacting with organelle surface component binding reagent (step 600*b*), contacting with organelle capture particles (step 600*c*), and/or removal of organelle capture particles (step 600*d*). Optionally, step 600*a* comprises lysing the plurality of cells and lysing organelle membranes without lysing the nuclear envelope, and therefore step 600*b*, step 600*c*, and/or step 600*d* are not conducted. In some embodiments, organelle contamination and/or extranuclear cellular component contamination (e.g., mitochondrial contamination) can be reduced (e.g., eliminated) for single cell analysis (e.g., whole transcriptome analysis or proteomics analysis) without conducting step 600*b*, step 600*c*, and/or step 600*d* of the workflow. In some embodiments, one or more of step 600*a*, step 600*b*, step 600*c*, step 600*d*, step 600*e*, step 600*f*, step 600*g*, step 600*h*, and/or step 600*i* of the workflow are performed simultaneously. For example, contacting with organelle surface component binding reagent (step 600*b*) and contacting with organelle capture particles (step 600c) can occur at the same time. In some such embodiments, the organelle surface component binding reagent is associated with an organelle capture particle. The organelle surface component binding reagent can be immobilized, or partially immobilized, on the organelle capture particle. For example, the organelle surface component binding reagent can be reversibly, non-reversibly, covalently, non-covalently, or a combination thereof, associated with the organelle capture particle. As another example, the organelle surface component binding reagent can embedded, partially embedded, non-embedded, enclosed, partially enclosed, non-enclosed, or a combination thereof, in the organelle capture particle.

In some embodiments, the nuclei binding reagent does not comprise a first epitope. In some such embodiments, the nuclei binding reagent can comprise a primary antibody capable of specifically binding to one or more components of the nuclei (e.g., nuclear envelope proteins) and the nucleus isolation particles are associated with a secondary antibody capable of specifically binding to the primary antibody. In some such embodiments, free primary antibody (instead of free first epitope) can be contacted with the lysate prior to isolation of the nucleus isolation particles.

Example 2

Nuclei Capture and Barcoding Workflow

Figure 7A:
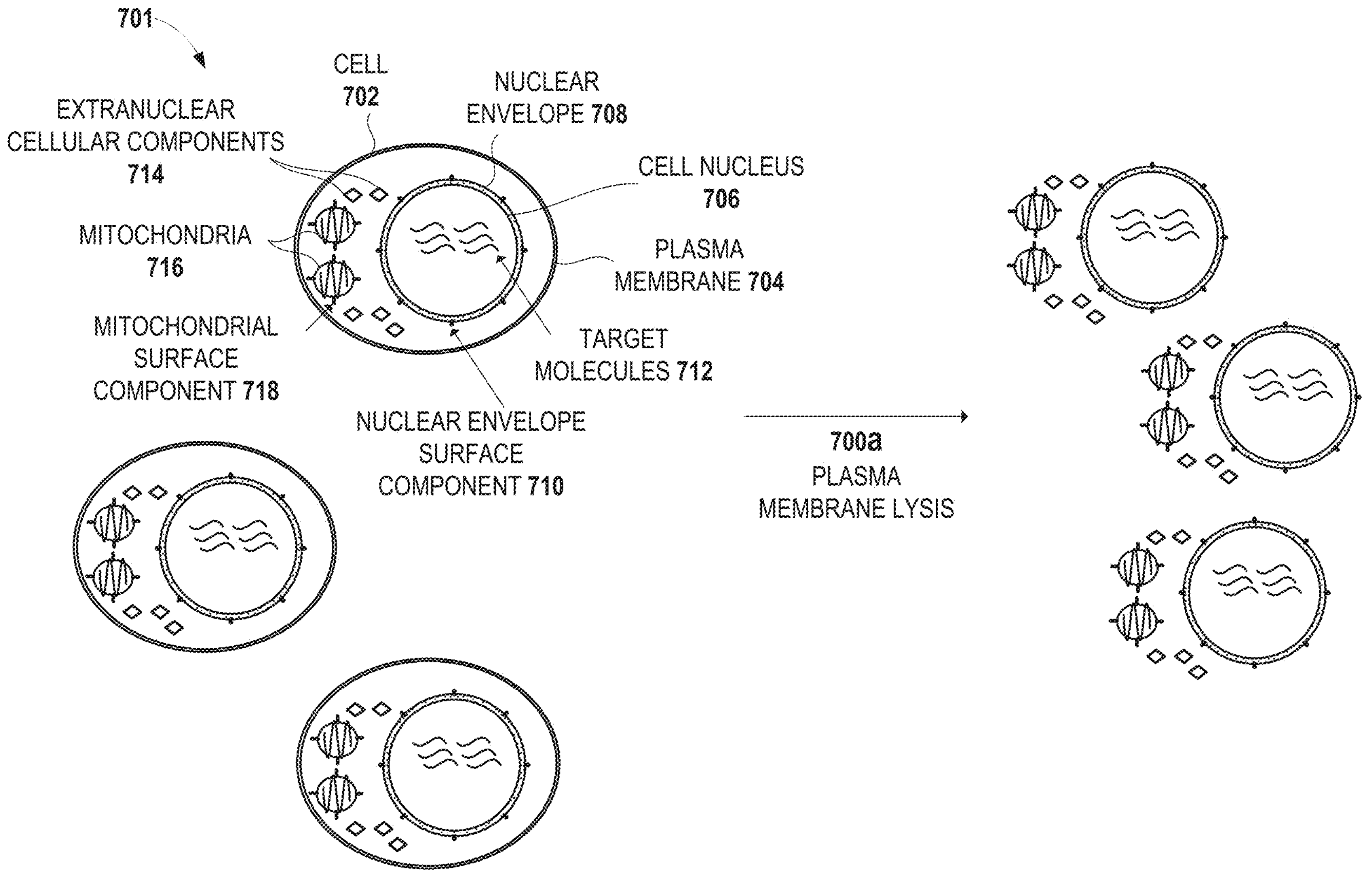
FIGS. 7A-7C show a non-limiting exemplary schematic illustration of a nuclei capture and barcoding workflow.
Figure 7B:
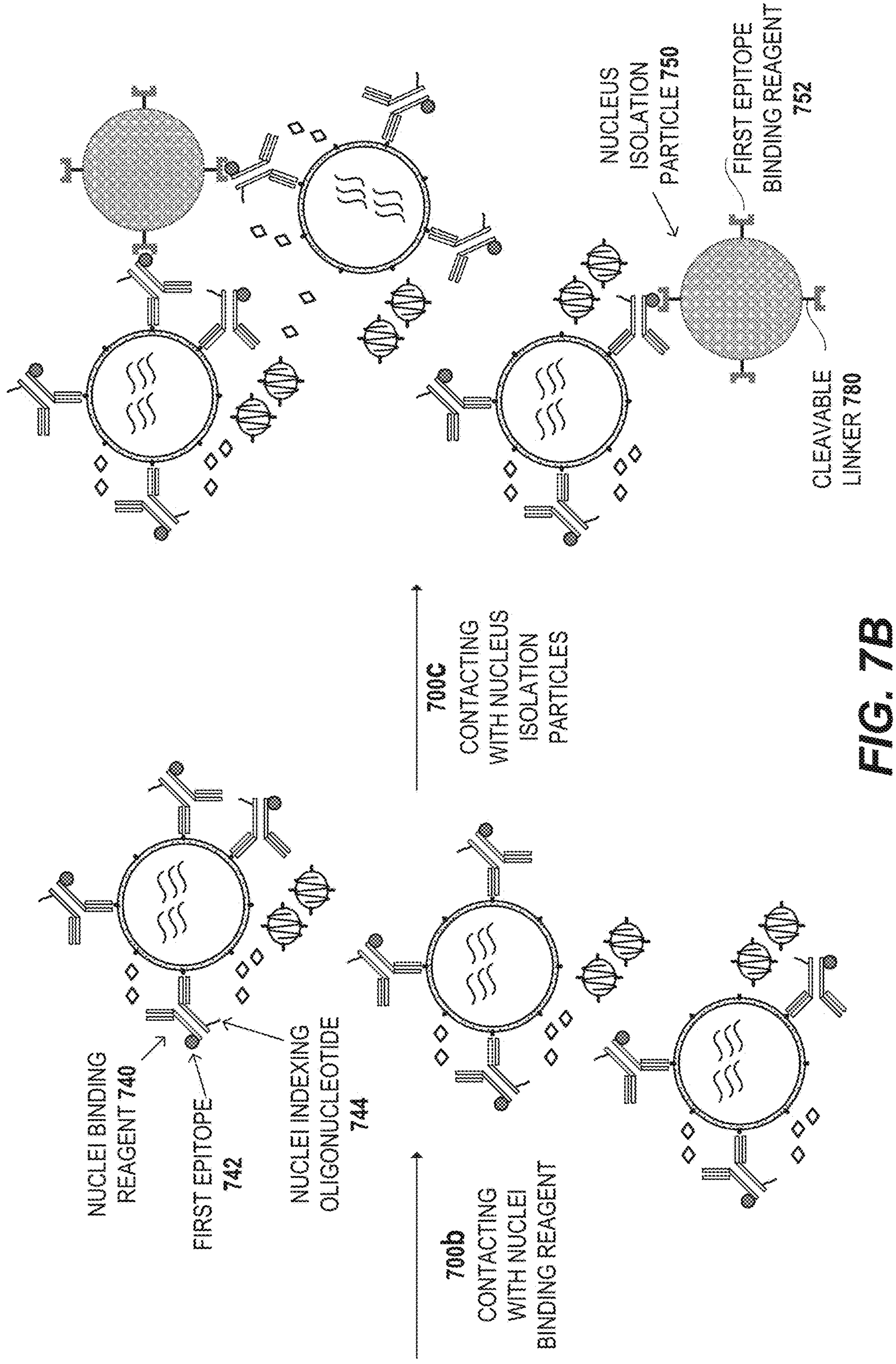
Figure 7C:
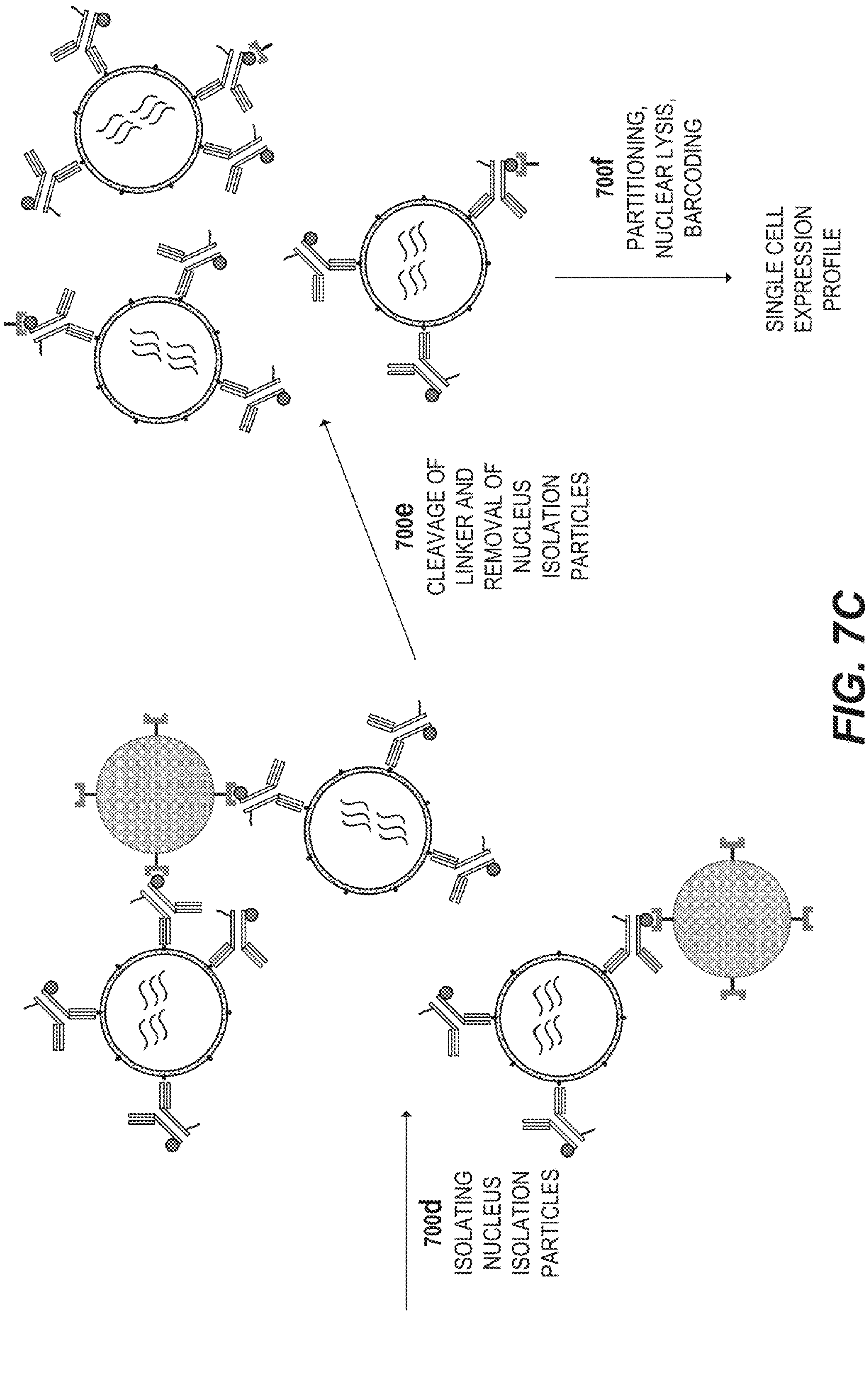

This example demonstrates a workflow for nuclei capture and barcoding. FIGS. 7A-7C is a schematic illustration of a non-limiting exemplary workflow for nuclei isolation and single cell profiling. The workflow can comprise cell lysis (e.g., using a light lysis buffer to lyse the plasma membrane without lysing the nuclear membrane and/or one or more organelles). The workflow can include associating each nuclei with a nuclei indexing oligonucleotide comprising a nuclei indexing sequence (e.g., for sample indexing). The workflow can include isolating nuclei from one or more cellular components and/or organelles. The workflow can include partitioning individual nuclei to partitions and conducting nucleus lysis. The workflow can include barcoding (e.g., stochastic barcoding) of target nucleic acid molecules and/or nuclei indexing oligonucleotides for single cell analysis (e.g., Rhapsody™ assay (Becton, Dickinson and Company (Franklin Lakes, NJ)), Chromium™ Single Cell 3' Solution (10× Genomics (San Francisco, CA))).

Sample Composition

Sample 701 can comprise a plurality of cells 702. A sample for use in the method of the disclosure can one for which it is technically difficult or impossible to generate a single-cell suspension (frozen cells, fixed cells, tissue specimens, tumor specimens, epithelial tissues, formalin-fixed paraffin-embedded cells, and combinations thereof). A cell can comprise a plasma membrane 704 and a cell nucleus 706. The cell nucleus can comprise a nuclear envelope 708 and one or more nucleic acid target molecules 712. The nuclear envelope can comprise one or more nuclear envelope surface components 710, such as a nuclear envelope protein (e.g., a lamin). The nucleus can include one or more target nucleic acid molecules (e.g., messenger RNA (mRNA), microRNA (miRNA), long non-coding RNA (long ncRNA or lncRNA), Piwi-interacting RNA (piRNA)). The cell can comprise one or more organelles (e.g., ribosomes, mitochondria) as described herein, and the one or more organelles can comprise one or more organelle surface components. Mitochondria 716 can comprise an organelle surface component (e.g., mitochondrial surface component 718). The cell can also comprise extranuclear cellular components 714. Extranuclear cellular components can comprise undesired extranuclear cytoplasmic components (e.g., molecules that are unnecessary and/or detrimental to single cell expression profiling). Extranuclear cellular components can include cytoplasmic fragments. Extranuclear cellular components can include organelles. Extranuclear cellular components can include mitochondria. Extranuclear cellular components can include ribosomes. Extranuclear cellular components can include rough endoplasmic reticuli. Extranuclear cellular components can comprise one or more undesired nucleic acids (e.g., ribosomal RNA, mitochondrial DNA, mitochondrial RNA). Extranuclear cellular components can comprise one or more macromolecules that would interfere with the single cell expression analysis methods disclosed herein. Extranuclear cellular components 714 can comprise mitochondria, peroxisomes, cytosol, vesicles, lysosomes, plasma membranes, chloroplasts, inner mitochondrial matrices, inner mitochondrial membranes, intermembrane spaces, outer mitochondrial membranes, secretory vesicles, smooth endoplasmic reticuli, rough endoplasmic reticuli, golgi bodies, phagosomes, endosomes, exosomes, plasma membranes, microtubules, microfilaments, intermediate filaments, filopodia, ruffles, lamellipodia, sarcomeres, focal contacts, podosomes, ribosomes, microsomes, lipid rafts, cell walls, and combinations thereof.

Plasma Membrane Lysis

The workflow can comprise plasma membrane lysis (step 700a) of the population of cells 702 of sample 701. Plasma membrane lysis can generate a lysate comprising plurality of a population of nuclei, organelles, and extranuclear cellular components (e.g., ribosomes) as depicted in FIG. 7A. The method can comprise lysing the plurality of cells without lysing the nuclear envelope. The method can comprise lysing the plurality of cells without lysing organelle membranes. The method can comprise lysing the plurality of cells and lysing organelle membranes without lysing the nuclear envelope. Plasma membrane lysis can be performed using a homogenizer (e.g., a Dounce homogenizer), a detergent, or an enzymatic method. In some embodiments the workflow comprises contacting the lysate with organelle surface component binding reagent, contacting the lysate with organelle capture particles, and/or removal of said organelle capture particles (e.g., step 600b, step 600c, and/or step 600d of Example 1) prior to performing step 700b.

Contacting with Nuclei Binding Reagent(s)

The workflow can comprise contacting the lysate with one or more nuclei binding reagents (step 700b). Nuclei binding reagent 740 can comprise a first epitope 742. The first epitope 742 can comprise a strong epitope (e.g, biotin, fluorescein, and/or DIG) as described herein. The nuclei binding reagent 740 can be capable of specifically binding to one or more components of the nuclei (e.g., nuclear envelope proteins) such as, for example nuclear envelope surface components 710 (as depicted in FIG. 7B). In some embodiments, the nuclei-binding reagent comprises a carbohydrate-binding reagent (e.g., a carbohydrate-binding protein, a lectin). Contacting the nuclei with the nuclei binding reagent can generate nuclei bound to the nuclei-binding reagent. The nuclei binding reagent 740 can comprise nuclei indexing oligonucleotide 744. The nuclei indexing oligonucleotide 744 can comprise a nuclei indexing sequence (e.g., for sample indexing). The nuclei indexing oligonucleotide 744 can remain associated with the nuclei throughout the entire workflow. In some embodiments, the workflow can comprise pooling nuclei from different samples once nuclei are bound by a nuclei binding reagent comprising a nuclei indexing oligonucleotide.

Contacting with Nucleus Isolation Particles

The workflow can comprise contacting the lysate with one or more nucleus isolation particles (step 700*c*). The nucleus isolation particle 750 can comprise a reagent capable of specifically binding to the nuclei binding reagent (e.g., a first epitope binding reagent 752 as depicted in FIG. 7B) as described herein. The first epitope binding reagent 752 can be associated with (e.g., immobilized, partially immobilized, enclosed, partially enclosed) the nucleus-isolation particle via a cleavable linker 780. The cleavable linker 780 can operably link the first epitope binding reagent 752 to the nucleus isolation particle 750. The cleavable linker can comprise a chemically cleavable linkage, a photocleavable linkage, an acid labile linker, a heat sensitive linkage, an enzymatically cleavable linkage, or a combination thereof. The nuclei-binding reagent can comprise a primary antibody capable of specifically binding to the one or more components of the nucleus, and the reagent capable of specifically binding to the nuclei binding reagent can comprise a secondary antibody capable of specifically binding to the primary antibody, wherein said secondary antibody is linked to the nucleus isolation particle via a cleavable linker. As depicted in FIG. 7B, step 700*c* can generate nuclei bound to nucleus isolation particles via the reagent capable of specifically binding to the nuclei binding reagent.

Isolation of Nucleus Isolation Particles

The workflow can comprise isolation of nucleus isolation particles (step 700*d*). Isolation of nucleus isolation particles (and the nuclei bound thereto) can comprise isolating the nucleus-isolation particle by magnetic removal, filtration, centrifugation, or any combination thereof. Step 700*d* can generate a plurality of isolated nucleus isolation particles (and nuclei bound thereto) depleted of organelles and/or extranuclear cellular components.

Cleavage of Linker and Removal of Nucleus Isolation Particles

The workflow can comprise cleavage of the cleavable linker (thereby effectuating separation of the nuclei from the nucleus isolation particles) and removal of nucleus isolation particles (step 700*e*). The plurality of isolated nucleus isolation particles (and nuclei bound thereto) can be exposed to conditions necessary to effectuate cleavage of the cleavable linker. Such conditions may include electrostatic environment (e.g., high pH, low pH), temperature (e.g., heat cleavable), a select wavelength of light (e.g., photocleavable), a chemical compound (e.g., chemically cleavable), an enzyme (e.g., enzyme cleavable). Upon cleavage of the cleavable linker, nuclei can be no longer associated with the nucleus isolation particles. Removal of the nucleus isolation particles from the nuclei can occur by magnetic removal, centrifugation, filtration, or any combination thereof, thereby generating a population of purified nuclei.

Partitioning Nuclear Lysis, and Barcoding

The workflow can comprise partitioning, nuclear lysis, and barcoding (step 700*f*). The plurality of nuclei can partitioned to a plurality of partitions. A partition can be a microwell, droplet, or emulsion. A partition of the plurality of partitions can comprise a single nuclei from the plurality of nuclei. A partition of the plurality of partitions can comprise a single nuclei from the plurality of nuclei and a barcoding particle. In some embodiments, the microwell dimensions (e.g., microwell depth) are chosen to optimize nuclei and barcoding particle trapping efficiency while also providing efficient exchange of assay buffers and other reagents contained within the wells.

In some embodiments, an emulsion, microwell, or well contains only one nuclei. In some embodiments, from 1 to 2,000,000 emulsions, microwells, or wells each contain only one nuclei. In some embodiments, the method comprises distributing at most one nuclei into each emulsion, microwell, or well. In some embodiments, a single solid support and a single nuclei are distributed to an emulsion, microwell, or well. In some embodiments, from 1 to 2,000,000 emulsions, microwells, or wells each have distributed thereto one nuclei and one solid support. In some embodiments, the method comprises distributing at most one solid support per emulsion, microwell, or well. In some embodiments, the method comprises distributing one solid support and one nuclei to each of from 1 to 2,000,000 microwells, emulsions, or wells. In some embodiments, nuclei distribution is random or non-random. In some embodiments, nuclei distribution is stochastic. In some embodiments, a nuclei is distributed by a cell sorter. In some embodiments, a nuclei is distributed by contacting one or more wells, microwells, or emulsions with a dilute solution of nuclei diluted so that at most one nuclei is distributed to the one or more wells, microwells, or emulsions.

In some instances, nuclei from a population of nuclei can be separated (e.g., isolated) into wells of a substrate of the disclosure. For example, the population of nuclei can be diluted prior to separating. The population of nuclei can be diluted such that at least 1%, 5%, 10%, 15%, 20%, 25%, 30%, 35%, 40%, 45%, 50%, 55%, 60%, 65%, 70%, 75%, 80%, 85%, 90%, 95% or 100%, of wells of the substrate receive a single nuclei. The population of nuclei can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100%, of wells of the substrate receive a single nuclei. The population of nuclei can be diluted such that the number of nuclei in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. The population of nuclei can be diluted such that the number of nuclei in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. In some instances, the population of nuclei is diluted such that the number of nuclei is about 10% of the number of wells in the substrate.

Distribution of single nuclei into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one nuclei. There can be at least a 0.1%, 0.5%, 1%, 2%, 3%, 4%, 5%, 6%, 7%, 8%, 9%, or 10%, or more probability that a well of the substrate has more than one nuclei. Distribution of single nuclei into wells of the substrate can be random. Distribution of single nuclei into wells of the substrate can be non-random. The nuclei can be separated such that a well of the substrate receives only one nuclei.

Once partitioned, nuclei can be lysed according to the methods provided herein. Barcoding can comprise using the plurality of barcodes of the barcoding particle to generate a plurality of barcoded nuclei indexing oligonucleotides and/or barcoded targets according to the methods provided herein. The products of Step 700*f* (e.g., barcoded nuclei indexing oligonucleotides and/or barcoded targets) can undergo the downstream methods provided herein to generate a single cell expression profile.

In some embodiments, one or more steps of the workflow comprise centrifugation. In some embodiments, one or more steps of the workflow do not comprise centrifugation. In some embodiments none of the steps of the workflow comprise centrifugation. In some embodiments, the workflow does not comprise one or more of step 700*a*, step 700*b*, step 700*c*, step 700*d*, step 700*e*, and/or step 700*f*. For example, the nuclei binding reagent can be associated with (e.g., immobilized, partially immobilized, enclosed, partially enclosed) a nucleus-isolation particle via a cleavable linker. In some embodiments, one or more of step step 700*a*, step 700*b*, step 700*c*, step 700*d*, step 700*e*, and/or step 700*f* of the workflow are performed simultaneously. For example, contacting with nuclei binding reagent (step 700*b*) and contacting with nucleus isolation particles (step 700*c*) can occur at the same time.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for determining the copy number of a nucleic acid target in a plurality of cells, comprising:

isolating a plurality of nuclei of a plurality of cells using a nuclei-isolation composition, wherein the plurality of cells are mammalian cells, wherein the mammalian cells are human cells, wherein the nuclei-isolation composition comprises a nuclei-binding reagent, and wherein the nuclei-binding reagent is a monoclonal IgG antibody capable of binding a nuclear pore complex;

barcoding copies of a nucleic acid target in the plurality of nuclei using the plurality of barcodes to generate a plurality of barcoded nucleic acid molecules, wherein each of the plurality of barcodes comprises a molecular label sequence and an oligo(dT) target-binding region, wherein the molecular label sequence is 5 to 20 nucleotides in length, and wherein the oligo(dT) target-binding region is 5 to 30 nucleotides in length, and wherein at least 1000 molecular label sequences of the plurality of barcodes comprise different sequences;

obtaining sequencing data of the plurality of barcoded nucleic acid molecules, wherein obtaining sequencing data comprises sequencing at least a portion of the molecular label sequence and at least a portion of the nucleic acid target; and estimating the copy number of the nucleic acid target in the plurality of cells using the molecular label sequences of the plurality of barcodes in the sequencing data.

2. The method of claim 1, wherein isolating the plurality of nuclei comprises:

contacting the plurality of nuclei of the plurality of cells with the nuclei-isolation composition to generate nuclei bound to the nuclei-binding reagent; and isolating the nuclei bound to the nuclei-binding reagent using a reagent capable of specifically binding to the nuclei-binding reagent.

3. The method of claim 2, wherein the reagent capable of specifically binding to the nuclei-binding reagent is attached to a nucleus-isolation particle; and wherein isolating the nuclei bound to the nuclei-binding reagent comprises isolating the nucleus-isolation particle by magnetic removal, centrifugation, or any combination thereof.

4. The method of claim 3, wherein the plurality of barcodes is attached to the nucleus-isolation particle.

5. The method of any one of claim 1, wherein the plurality of cells comprise a tissue sample, frozen cells, fixed cells, formalin-fixed paraffin-embedded cells, a tumor sample, an epithelial tissue sample, or any combination thereof.

6. The method of claim 1, wherein said nuclei-binding reagent comprises a nuclei indexing oligonucleotide, wherein the nuclei indexing oligonucleotide comprises deoxyribonucleic acid (DNA), and wherein the nuclei indexing oligonucleotide comprises a nuclei indexing sequence.

7. The method of claim 6, wherein the method comprises:

barcoding the nuclei indexing oligonucleotides using a plurality of barcodes to generate a plurality of barcoded nuclei indexing oligonucleotides; and obtaining sequencing data of the plurality of barcoded nuclei indexing oligonucleotides.

8. The method of claim 1, wherein the monoclonal IgG antibody is conjugated with digoxygenin.

* * * * *